United States Patent
Grillo et al.

(10) Patent No.: US 12,344,607 B2
(45) Date of Patent: Jul. 1, 2025

(54) SUBSTITUTED 5,6,7,8-TETRAHYDROPYRIDO[2,3-d] PYRIMIDINE-2,4-DIONES FOR TREATING CARDIAC DISEASES

(71) Applicant: MYOKARDIA, INC., Brisbane, CA (US)

(72) Inventors: Mark Grillo, South San Francisco, CA (US); Brian Kane, San Mateo, CA (US); Johan Oslob, Sunnyvale, CA (US); Min Zhong, Palo Alto, CA (US); Fabienne Thompson, Paris (FR)

(73) Assignee: MyoKardia, Inc., Brisbane, CA (US)

( * ) Notice: Subject to any disclaimer, the term of this patent is extended or adjusted under 35 U.S.C. 154(b) by 23 days.

(21) Appl. No.: 18/228,911

(22) Filed: Aug. 1, 2023

(65) Prior Publication Data
US 2024/0025894 A1   Jan. 25, 2024

Related U.S. Application Data

(63) Continuation of application No. 18/153,534, filed on Jan. 12, 2023, now abandoned, which is a continuation of application No. 17/854,398, filed on Jun. 30, 2022, now abandoned, which is a continuation of application No. 17/554,353, filed on Dec. 17, 2021, now abandoned, which is a continuation of application No. 17/319,139, filed on May 13, 2021, now abandoned, which is a continuation of application No. 16/665,897, filed on Oct. 28, 2019, now Pat. No. 11,034,693.

(60) Provisional application No. 62/752,278, filed on Oct. 29, 2018.

(51) Int. Cl.
A61K 31/519     (2006.01)
C07D 471/04    (2006.01)

(52) U.S. Cl.
CPC .................. C07D 471/04 (2013.01)

(58) Field of Classification Search
CPC .......................... A61K 31/519; C07D 471/04
USPC ........................................ 514/258.1; 544/279
See application file for complete search history.

(56) References Cited

U.S. PATENT DOCUMENTS 6,335,341 B1   1/2002   Johnson et al.
6,653,306 B1   11/2003  Alexander et al.
2016/0176868 A1   6/2016   Oslob et al.

FOREIGN PATENT DOCUMENTS

EP      3873904 A1   9/2021
WO   2014205223 A1   12/2014

OTHER PUBLICATIONS

Written Opinion of International Searching Authority for PCT/US2019/058297 dated May 7, 2020.
Anderson, RL, et al., "Deciphering the super relaxed state of human β-cardiac myosin and the mode of action of mavacamten from myosin molecules to muscle fibers", Proc Natl Acad Sci U S A. Aug. 28, 2018;115(35):E8143-E8152.
Anderson, RL, et al., "Hypertrophic Cardiomyopathy Mutations Destabilize the Super-Relaxed State of Myosin", Feb. 2017Biophysical Journal 112(3):258a-259a.
Anto, A., et al., "MYH7 R403Q Mutation in Pigs: Altered Myofilament Dynamics, Hyper-Contractility, and Impaired Function In Vivo", Journal of Molecular and Cellular Cardiology, Nov. 1, 2018, p. 2-11, vol. 124, p. 107.
Bolleddula, J, et al., "Biotransformation and bioactivation reactions of alicyclic amines in drug molecules", Drug Metab Rev. Aug. 2014;46(3):379-419.
Del Rio, C., "Abstract of the 2017 A-CURE Symposium", Journal of Cardiovascular Translational Research 11.1 (Feb. 2018): 59.
Del Rio, C., et al., "Abstract 20593: In vivo Cardiac Effects of Mavacamten (MYK-461): Evidence for Negative Inotropy and Improved Compliance", Circulation. 2017; 136:A20593.
Del Rio, C., et al., "Abstract 20770: A Novel Mini-Pig Genetic Model of Hypertrophic Cardiomyopathy: Altered Myofilament Dynamics, Hyper-Contractility, and Impaired Systolic/Diastolic Functional Reserve in vivo", Circulation. 2017; 136:A20770.

(Continued)

*Primary Examiner* — Douglas M Willis
(74) *Attorney, Agent, or Firm* — Honigman LLP; Andrew Chipouras; Jonathan P. O'Brien

(57) ABSTRACT

The present disclosure provides novel tetrahydropyran (THP)-substituted bicyclic pyrimidinedione compounds, including (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione (shown below), that are useful for the treatment of hypertrophic cardiomyopathy (HCM), conditions associated with left ventricular hypertrophy, conditions associated with diastolic dysfunction, and/or symptoms associated thereof. The synthesis and characterization of the compounds is described, as well as methods for treating HCM and other forms of heart disease.

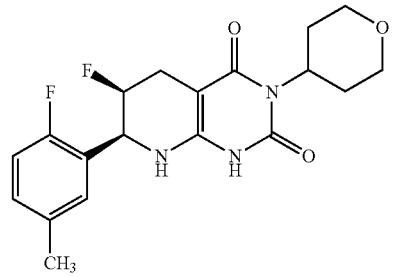

15 Claims, 6 Drawing Sheets

(56) References Cited

OTHER PUBLICATIONS

Del Rio, C.L, et al., "Abstract 14585: Chronic Treatment With a Mavacamten-Like Myosin-Modulator (MYK-581) Blunts Disease Progression in a Mini-Pig Genetic Model of Non-Obstructed Hypertrophic Cardiomyopathy: In Vivo Evidence for Improved Relaxation and Functional Reserve", Circulation, 2019; 140:A14585.
Del Rio, C.L, et al., "Simultaneous integration of telemetered left-ventricular pressure and echocardiography in rats: Minimally-invasive serial pressure-volume relationships in the setting of normal and impaired diastolic function", J Pharmacol Toxicol Methods, Sep.-Oct. 2019;99:106595.
Dick, R., et al., "Abstracts from the 10th International ISSX Meeting", Drug Metabolism Reviews, suppl. 1 45 (Jan. 2014): 201.
Driscoll, JP, "Role of Glucuronidation and P450 Oxidation in the Bioactivation of Bromfenac", Chem Res Toxicol, Apr. 16, 2018;31(4):223-230.
Geist, B,et al., "Telemetered left-ventricular pressure in Yucatan mini-pigs: Chronic evaluation in a novel genetic model of non-obstructed hypertrophic cardiomyopathy", J Pharmacol Toxicol Methods, Sep.-Oct. 2019; 99:106595.
Ghermazien, H., et al., "Cardiac Selective Modulator of Human Myosin for the Treatment of Genetic Hypertrophic Cardiomyopathy", Biophysical Journal, 2014, vol. 106(2), pp. 729a-730a.
Green, EM, et al., "A small-molecule inhibitor of sarcomere contractility suppresses hypertrophic cardiomyopathy in mice", Science. Feb. 5, 2016;351(6273):617-21.
Green, EM, et al., "Abstract 14467: A Minipig Genetic Model of Hypertrophic Cardiomyopathy", Circulation. 2016;134:A14467.
Green, EM, et al., "Abstract 14661: A Novel Mini-Pig Genetic Model of Hypertrophic Cardiomyopathy (HCM) Exhibits Reduced Myocardial Capillary Density, Impaired Myocardial Flow Reserve, and Chronic Injury", Circulation, 2018;138:A14661.
Grillo, MP, "Detecting reactive drug metabolites for reducing the potential for drug toxicity ", Expert Opinion Drug Metabolism & Toxicology 11.8 (Aug. 2015): 1281-1302.
Grillo, MP, et al., "In vitro and in vivo pharmacokinetic characterization of mavacamten, a first-in-class small molecule allosteric modulator of beta cardiac myosin", Xenobiotica. Jun. 2019;49(6), pp. 718-733.
Heitner, S. et al., "Abstract 17141: mavacamten improves left ventricular relaxation and compliance in obstructive hypertrophic cardiomyopathy through direct myosin modulation", Circulation, 2018; 138:A17141-A17141.
Heitner, SB, et al., "Abstract 13962: Precision Pharmacological Treatment for Obstructive Hypertrophic Cardiomyopathy With Mavacamten: One-Year Results From PIONEER-OLE", Circulation, 2019; 140:A13962.
Heitner, SB, et al., "Abstract 17067: MAVERICK-HCM: Phase 2 Randomized, Multi-Center, Double-Blind, Placebo-Controlled Concentration-Guided Study to Evaluate Mavacamten (MYK-461) in Adults With Symptomatic Non-Obstructive Hypertrophic Cardiomyopathy", Circulation, 2018;138:A17067.
Heitner, SB, et al., "Mavacamten Treatment for Obstructive Hypertrophic Cardiomyopathy: A Clinical Trial", Ann Intern Med., Jun. 4, 2019; 170(11), pp. 741-748.
Henze, M., et al. "Abstract 905: Length Dependent Activation in Porcine Cardiac Myofilaments is Modulated by Mavacamten", Circulation Research. 2019;125:A905.
Homburger, JR, et al., "Multidimensional structure-function relationships in human β-cardiac myosin from population-scale genetic variation" Proceedings of the National Academy of Sciences Jun. 2016, 113 (24) 6701-6706.
Jacoby, D., et al., "Reduction in Left Ventricular Outflow Tract Gradient With Mavacamten (MYK-461) in Symptomatic Obstructive Hypertrophic Cardiomyopathy Patients (Pioneer-HCM)", J Am Coll Cardiol. Mar. 2018, 71 (11_Supplement) A644.

Kawas, RF, et al., "A small-molecule modulator of cardiac myosin acts on multiple stages of the myosin chemomechanical cycle", J Biol Chem. Oct. 6, 2017; 292(40):16571-16577.
Lee, SP, et al., "Incident Atrial Fibrillation Is Associated With MYH7 Sarcomeric Gene Variation in Hypertrophic Cardiomyopathy", Circ Heart Fail, Sep. 2018;11(9):e005191.
Markova, S., et al., "Chemical Inhibition or Genetic Disruption of Soluble Epoxide Hydrolase Does Not Protect From Acute Kidney Injury in a Mouse Renal Ischemia Reperfusion Model", Drug Metabolism Reviews 47.Suppl. 1, Sp. Iss. SI (Nov. 20, 2015): 135.
Maron, M., et al., "Abstract 16842: Obstructive Hypertrophic Cardiomyopathy: Initial Single Ascending Dose Data in Healthy Volunteers and Patients", Circulation. 2016; 134:A16842.
Mentias, A, et al., "Late Gadolinium Enhancement in Patients With Hypertrophic Cardiomyopathy and Preserved Systolic Function", J Am Coll Cardiol. Aug. 21, 2018;72(8):857-870.
Oslob, J., "Discovery of sarcomere modulator mavacamten", Abstracts of Papers American Chemical Society 256 (Aug. 19, 2018): 258.
Ribeiro, AJS, et al., "Considerations for an In Vitro, Cell-Based Testing Platform for Detection of Drug-Induced Inotropic Effects in Early Drug Development. Part 2: Designing and Fabricating Microsystems for Assaying Cardiac Contractility With Physiological Relevance Using Human iPSC-Cardiomyocytes", Front Pharmacol. Aug. 29, 2019;10:934, 19 pages.
Rodriguez, H., "Modulation of the Cardiac Sarcomere by a Small Molecule Agent MYK0000461: A Potential Therapeutic for the Treatment of Genetic Hypertrophic Cardiomyopathies", Biophysical Journal, Jan. 2014, 106(2):562a.
Sa, N., et al., "Abstract 340: Myosin Regulatory Light Chain: A Major Player in Defining the 'Off' State of Cardiac Myosin", Circulation Research. 2019;125:A340.
Sa, N., et al., "Abstract 572: Role Of Human Cardiac RLC In Modulating The Super-relaxed State Of Myosin: A Cardiomyopathy Perspective", Circulation Research, 2018;123:A572.
Salberg, L., "Hypertrophic Cardiomyopathy: A Heart Burden and Challenging Diagnosis", Value in Health, May 1, 2016, vol. 19, ISSUE 3, PA52.
Shi, J, et al., "Predicting Human Pharmacokinetics: Physiologically Based Pharmacokinetic Modeling and In Silico ADME Prediction in Early Drug Discovery", Eur J Drug Metab Pharmacokinet, Feb. 2019; 44(1), pp. 135-137.
Stern, Joshua A. et al., "A Small Molecule Inhibitor of Sarcomere Contractility Acutely Relieves Left Ventricular Outflow Tract Obstruction in Feline Hypertrophic Cardiomyopathy," PLoS One (published online Dec. 14, 2016; 10.1371/journal.phone.0168407); 11(12):e0168407; 11 pages. XP055514347.
Sun, S., et al., "Abstract 14837: Pro-Compliant Effects of Mavacamten Are Preserved in the Setting of β-adrenergic Receptor Blockade: In vivo and ex vivo Evidence", Circulation, 2019; 140:A14837.
Tomasic, IB, et al., "2-Deoxy-ATP Enhances Multiple Kinetic Parameters to Improve Cardiac Function", Biophysical Journal, Feb. 16, 2016, vol. 110, Issue 3, Supplement 1, 202A.
Tompkins, JDV, et al., "Abstract 14251: Peak Oxygen Consumption is an Independent Predictor of Survival and Outcomes in Obstructive and Non-Obstructive Hypertrophic Cardiomyopathy (HCM) Patients: Results From the International Sarcomeric Human Cardiomyopathies Registry (SHaRe)", Circulation, 2018;138:A14251.
Truong, QA, "A four-tier classification system of pulmonary artery metrics on computed tomography for the diagnosis and prognosis of pulmonary hypertension", J Cardiovasc Comput Tomogr, Jan.-Feb. 2018;12(1):60-66.
Zha, W, "Transporter-mediated natural product-drug interactions for the treatment of cardiovascular diseases", J Food Drug Anal, Apr. 2018;26(2S):S32-S44.
Zha, W, et al., "Effect of Pregnancy on Paroxetine-Induced Adiposity and Glucose Intolerance in Mice", J Pharmacol Exp Ther., Oct. 2019;371(1), pp. 113-120.
Zhong, M, et al., "Discovery of novel potent HCV NS5B polymerase non-nucleoside inhibitors bearing a fused benzofuran scaffold", Bioorg Med Chem Lett. Mar. 1, 2018;28(5):963-968.
Iacopo, O., et al., "Explorer-HCM: Phase 3 randomized, multi-center, double-blind, placebo-controlled study to evaluate mavacamten (MYK461) in adults with symptomatic obstructive hypertrophic cardiomyopathy", Circulation, suppl. Supplement 1 138 (Nov. 2018).

| Visible | Icon | Color | Index | Name | Parent | Caption (display) | Scan | Angle | d Value |
|---|---|---|---|---|---|---|---|---|---|
| Yes | | | 1 | Peak #1 | Peak List #1 | 8.182 ° | | 8.182 ° | 14.28459 Å |
| Yes | | | 2 | Peak #2 | Peak List #1 | 9.977 ° | | 9.977 ° | 8.85268 Å |
| Yes | | | 3 | Peak #3 | Peak List #1 | 11.316 ° | | 11.316 ° | 7.81306 Å |
| Yes | | | 4 | Peak #4 | Peak List #1 | 12.390 ° | | 12.390 ° | 7.13801 Å |
| Yes | | | 5 | Peak #5 | Peak List #1 | 13.266 ° | | 13.266 ° | 6.66877 Å |
| Yes | | | 6 | Peak #6 | Peak List #1 | 14.479 ° | | 14.479 ° | 6.11270 Å |
| Yes | | | 7 | Peak #7 | Peak List #1 | 16.129 ° | | 16.129 ° | 5.49086 Å |
| Yes | | | 8 | Peak #8 | Peak List #1 | 16.476 ° | | 16.476 ° | 5.37646 Å |
| Yes | | | 9 | Peak #9 | Peak List #1 | 17.340 ° | | 17.340 ° | 5.10987 Å |
| Yes | | | 10 | Peak #10 | Peak List #1 | 18.082 ° | | 18.082 ° | 4.90186 Å |
| Yes | | | 11 | Peak #11 | Peak List #1 | 19.298 ° | | 19.298 ° | 4.59585 Å |
| Yes | | | 12 | Peak #12 | Peak List #1 | 20.387 ° | | 20.387 ° | 4.35271 Å |
| Yes | | | 13 | Peak #13 | Peak List #1 | 21.177 ° | | 21.177 ° | 4.19194 Å |
| Yes | | | 14 | Peak #14 | Peak List #1 | 22.503 ° | | 22.503 ° | 3.94787 Å |
| Yes | | | 15 | Peak #15 | Peak List #1 | 23.222 ° | | 23.222 ° | 3.82728 Å |
| Yes | | | 16 | Peak #16 | Peak List #1 | 25.529 ° | | 25.529 ° | 3.48640 Å |
| Yes | | | 17 | Peak #17 | Peak List #1 | 26.436 ° | | 26.436 ° | 3.36881 Å |
| Yes | | | 18 | Peak #18 | Peak List #1 | 28.241 ° | | 28.241 ° | 3.15741 Å |
| Yes | | | 19 | Peak #19 | Peak List #1 | 28.883 ° | | 28.883 ° | 3.08868 Å |
| Yes | | | 20 | Peak #20 | Peak List #1 | 29.478 ° | | 29.478 ° | 3.02767 Å |
| Yes | | | 21 | Peak #21 | Peak List #1 | 30.333 ° | | 30.333 ° | 2.94429 Å |
| Yes | | | 22 | Peak #22 | Peak List #1 | 31.511 ° | | 31.511 ° | 2.83683 Å |
| Yes | | | 23 | Peak #23 | Peak List #1 | 32.885 ° | | 32.885 ° | 2.72141 Å |
| Yes | | | 24 | Peak #24 | Peak List #1 | 34.268 ° | | 34.268 ° | 2.61470 Å |
| Yes | | | 25 | Peak #25 | Peak List #1 | 35.545 ° | | 35.545 ° | 2.52357 Å |
| Yes | | | 26 | Peak #26 | Peak List #1 | 36.967 ° | | 36.967 ° | 2.42970 Å |
| Yes | | | 27 | Peak #27 | Peak List #1 | 38.769 ° | | 38.769 ° | 2.32082 Å |

FIG. 1B

| Net Intensity | Gross Intensity | Rel. Intensity | h,k,l | Match |
|---|---|---|---|---|
| 89.9 | 308 | 0.2 % | n.a. | No |
| 144 | 546 | 0.3 % | n.a. | No |
| 5416 | 5887 | 12.9 % | n.a. | No |
| 2081 | 2575 | 5.0 % | n.a. | No |
| 2437 | 2896 | 5.8 % | n.a. | No |
| 150 | 562 | 0.4 % | n.a. | No |
| 2914 | 3435 | 6.9 % | n.a. | No |
| 7113 | 7670 | 16.9 % | n.a. | No |
| 1721 | 2345 | 4.1 % | n.a. | No |
| 383 | 1062 | 0.9 % | n.a. | No |
| 42016 | 42767 | 100.0 % | n.a. | No |
| 4035 | 4799 | 9.6 % | n.a. | No |
| 336 | 1077 | 0.8 % | n.a. | No |
| 760 | 1438 | 1.8 % | n.a. | No |
| 1262 | 1889 | 3.0 % | n.a. | No |
| 808 | 1325 | 1.9 % | n.a. | No |
| 1381 | 1894 | 3.3 % | n.a. | No |
| 1733 | 2285 | 4.1 % | n.a. | No |
| 1156 | 1743 | 2.8 % | n.a. | No |
| 4614 | 5219 | 11.0 % | n.a. | No |
| 377 | 982 | 0.9 % | n.a. | No |
| 601 | 1194 | 1.4 % | n.a. | No |
| 630 | 1158 | 1.5 % | n.a. | No |
| 445 | 905 | 1.1 % | n.a. | No |
| 658 | 1088 | 1.6 % | n.a. | No |
| 73.5 | 457 | 0.2 % | n.a. | No |
| 990 | 1393 | 2.4 % | n.a. | No |

FIG. 1C

SUBSTITUTED 5,6,7,8-TETRAHYDROPYRIDO[2,3-d] PYRIMIDINE-2,4-DIONES FOR TREATING CARDIAC DISEASES

CROSS-REFERENCES TO RELATED APPLICATIONS

This application is a continuation of U.S. patent application Ser. No. 18/153,534, filed on Jan. 12, 2023, which is a continuation of U.S. patent application Ser. No. 17/854,398, filed on Jun. 30, 2022, which is a continuation of U.S. patent application Ser. No. 17/554,353, filed on Dec. 17, 2021, which is a continuation of U.S. patent application Ser. No. 17/319,139, filed on May 13, 2021, which is a continuation of U.S. patent application Ser. No. 16/665,897, filed on Oct. 28, 2019, which claims the benefit of priority under 35 U.S.C. § 119 (e) of U.S. Provisional Application, U.S. Ser. No. 62/752,278, filed Oct. 29, 2018, entitled "Tetrahydropyran (THP)-Substituted Bicyclic-Pyrimidinedione Compounds." The entire contents of each of these applications are incorporated herein by reference.

BACKGROUND OF THE INVENTION

Genetic (heritable) hypertrophic cardiomyopathy (HCM) comprises a group of highly penetrant, monogenic, autosomal dominant myocardial diseases. HCM is caused by one or more of over 1,000 known point mutations in any one of the structural protein genes contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, once other heritable (e.g., lysosomal storage diseases), metabolic, or infiltrative causes have been excluded.

Sarcomere gene mutations that cause HCM are highly penetrant, but there is wide variability in clinical severity and clinical course. Some genotypes are associated with a more malignant course, but there is considerable variability between and even within families carrying the same mutation. Sex differences have also been noted, with male patients generally more severely affected than female patients. While many patients with HCM report minimal or no symptoms for extended periods of time, HCM is a progressive disease with a significant cumulative burden of morbidity. Symptoms of effort intolerance predominate, and can be exacerbated by exercise and other maneuvers that increase heart rate and/or decrease preload. As with many other disorders, symptoms tend to worsen with age. By far the most prevalent clinical burden for patients with HCM is exertional dyspnea, which limits their activities of daily living and can be debilitating.

Patients with HCM are often symptomatic in the absence of documented hemodynamic abnormalities like left ventricular outflow tract obstruction (with or without mitral regurgitation). Patients' symptoms of exertional dyspnea can rapidly worsen with the onset of atrial fibrillation, a common complication of HCM that can precipitate acute pulmonary edema and increases the risk of systemic arterial thromboembolic disease, including stroke. Other adverse events associated with HCM include intolerance of hypovolemia or hypervolemia, and syncope. Concomitant coronary artery disease may confer a higher risk of acute coronary syndromes than in patients without HCM. Sudden cardiac death (SCD) in patients with HCM is both uncommon and difficult to predict but is a leading cause of non-traumatic death in young adults. For survivors of SCD, ICD placement is standard practice, and in other HCM patients risk profiling, while imprecise, is used to identify those for whom ICD placement for primary prevention is deemed prudent.

Medical therapy for HCM is limited to the treatment of symptoms and does not address the fundamental, underlying cause of disease—disruptions in normal sarcomere function. Currently available therapies are variably effective in alleviating symptoms but typically show decreased efficacy with increasing disease duration. Patients are thus empirically managed with beta-blockers, non-dihydropyridine calcium channel blockers, and/or disopyramide. None of these agents carry labeled indications for treating HCM, and essentially no rigorous clinical trial evidence is available to guide their use. Compounding this unfortunate situation is the fact that no new medical therapies for HCM have been identified for many years. For patients with hemodynamically significant outflow tract obstruction (resting gradient >30 mmHg), in appropriately selected patients surgical myectomy or alcohol septal ablation is usually required to alleviate the hemodynamic obstruction. The present disclosure provides new therapeutic agents and methods that remedy the long-felt need for improved treatment of HCM and related cardiac disorders and/or diseases.

SUMMARY OF THE INVENTION

In one aspect, provided is a compound having formula (I):

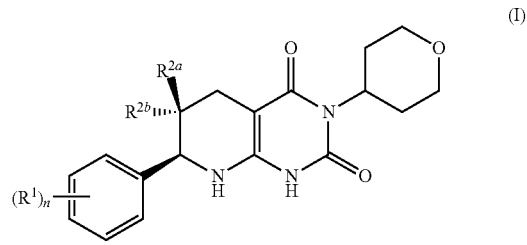

or a pharmaceutically acceptable salt thereof, wherein
the subscript n is 1 or 2;
each $R^1$ is a member selected from the group consisting of fluoro, chloro, $C_1$-$C_4$ alkyl, $C_1$-$C_4$ haloalkyl, $C_1$-$C_4$ alkoxy, $C_1$-$C_4$ haloalkoxy, and $C_2$-$C_4$ alkynyl; wherein at least one $R^1$ is fluoro; and one of $R^{2a}$ and $R^{2b}$ is fluoro and the other of $R^{2a}$ and $R^{2b}$ is H.

In one aspect, provided is a compound having formula (I):

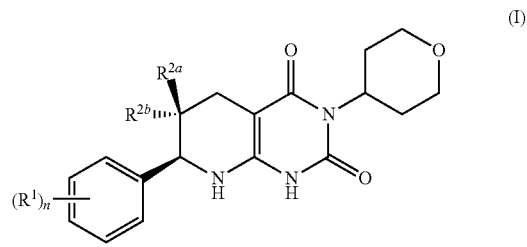

or a pharmaceutically acceptable salt thereof, wherein
the subscript n is 1 or 2;
each $R^1$ is a member selected from the group consisting of fluoro, chloro, optionally substituted $C_1$-$C_4$ alkyl, optionally substituted $C_1$-$C_4$ haloalkyl, optionally substituted C$_1$-C$_4$ alkoxy, optionally substituted C$_1$-C$_4$ haloalkoxy, and optionally substituted C$_2$-C$_4$ alkynyl; wherein at least one R$^1$ is fluoro; and one of R$^{2a}$ and R$^{2b}$ is fluoro and the other of R$^{2a}$ and R$^{2b}$ is H.

In another aspect, provided is Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione ("Form 1 polymorph"). In another aspect, the Form 1 polymorph is characterized by at least one of:

a. a powder X-ray diffraction pattern having two or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees;

b. a DSC thermogram showing endotherms at about 226.05° C., at about 302.47° C., and at about 310.13° C.; or c. an X-ray crystal structure substantially the same as in FIG. 4.

In another aspect, the disclosure provides a pharmaceutical composition comprising a compound of formula (I) or a pharmaceutically acceptable salt thereof as described herein and optionally a pharmaceutically acceptable excipient.

In some aspects, the present disclosure provides a method of treating a cardiac disease or disorder in a subject in need thereof, comprising administering to the subject an effective amount of a compound described herein. In certain aspects, diastolic dysfunction is a feature of and/or associated with the cardiac disease or disorder. For instance, the cardiac disease or disorder may be cardiomyopathy (e.g., hypertrophic cardiomyopathy), heart failure (e.g., heart failure with preserved ejection fraction, heart failure with midrange ejection fraction), valvular disease (e.g., valvular aortic stenosis), congenital heart disease (e.g., Tetralogy of Fallot), left ventricular hypertrophy, angina pectoris (e.g., refractory angina pectoris), or Chagas disease.

In certain aspects, the present disclosure provides methods of treating a cardiac disease or disorder, comprising administering to a subject in need thereof an effective amount of a compound as described herein, or a pharmaceutically acceptable salt thereof, pharmaceutical composition as described herein, or polymorph as described herein, wherein the cardiac disease or disorder is selected from the group consisting of diastolic dysfunction, hypertrophic cardiomyopathy, nHCM, oHCM, heart failure, HFpEF, HFmREF, valvular disease, Aortic Stenosis, left ventricular hypertrophy, restrictive cardiomyopathy, inflammatory cardiomyopathy, Loeffler endocarditis, endomyocardial fibrosis, infiltrative cardiomyopathy, hemochromatosis, Fabry disease, glycogen storage disease, congenital heart disease, Tetralogy of Fallot, left ventricular hypertrophy, angina pectoris, refractory angina pectoris, and Chagas disease. In certain aspects, the cardiac disease or disorder is selected from the group consisting of nHCM, oHCM, HFpEF, HFmREF, Aortic Stenosis, Loeffler endocarditis, endomyocardial fibrosis, infiltrative cardiomyopathy, hemochromatosis, Fabry disease, glycogen storage disease, Tetralogy of Fallot, angina pectoris, refractory angina pectoris, and Chagas disease.

In some aspects, the present disclosure provides methods of treating a cardiac disease or disorder, comprising administering to a subject in need thereof an effective amount of a compound as described herein, or a pharmaceutically acceptable salt thereof, pharmaceutical composition as described herein, or polymorph as described herein, wherein the compound, or pharmaceutically acceptable salt thereof, polymorph, or pharmaceutical composition is administered as a monotherapy.

In some aspects, the present disclosure provides methods of treating a cardiac disease or disorder, comprising administering to a subject in need thereof an effective amount of a compound as described herein, or a pharmaceutically acceptable salt thereof, pharmaceutical composition as described herein, or polymorph as described herein, wherein the compound, or pharmaceutically acceptable salt thereof, polymorph, or pharmaceutical composition is administered as a combination therapy, wherein an additional therapeutic agent administered. In certain aspects, the additional therapeutic agent is selected from the group consisting of beta adrenergic blocking agent (beta-blocker), renin-angiotensin-aldosterone system (RAAS) inhibitor (e.g., an angiotensin converting enzyme (ACE) inhibitor, an angiotensin receptor antagonist, such as an angiotensin II receptor blocker), an angiotensin receptor neprilysin inhibitor (ARNI) (e.g., sacubitril/valsartan), a mineralocorticoid receptor antagonist (MRA) (e.g., an aldosterone inhibitor such as a potassium-sparing diuretic such as eplerenone, spironolactone, or canrenone), a cholesterol lowering drug (e.g., a statin), a neutral endopeptidase inhibitor (NEPi), a positive inotropic agent (e.g., digoxin, pimobendane, a beta adrenergic receptor agonist such as dobutamine, a phosphodiesterase (PDE)-3 inhibitor such as milrinone, or a calcium-sensitizing agent such as levosimendan), potassium, magnesium, a proprotein convertase subtilisin kexin-type 9 (PCSK9) inhibitor, a vasodilator (e.g., a calcium channel blocker, phosphodiesterase inhibitor, endothelin receptor antagonist, renin inhibitor, or smooth muscle myosin modulator), a diuretic (e.g., furosemide), an arrhythmia medication, an anticoagulant (e.g., warfarin), an antithrombotic agent, an antiplatelet agent, a sodium-glucose cotransporter 2 inhibitor (SGLT2) (e.g., empaglifozin, dapagliflozin, sotagliflozin) or any combination thereof. In some aspects, the additional therapeutic is an angiotensin II receptor blocker (ARB) which is selected from the group consisting of A-81988, A-81282, BIBR-363, BIBS39, BIBS-222, BMS-180560, BMS-184698, candesartan, candesartan cilexetil, CGP-38560A, CGP-48369, CGP-49870, CGP-63170, CI-996, CV-11194, DA-2079, DE-3489, DMP-811, DuP-167, DuP-532, E-4177, elisartan, EMD-66397, EMD-73495, eprosartan, EXP-063, EXP-929, EXP-3174, EXP-6155, EXP-6803, EXP-7711, EXP-9270, FK-739, GA-0056, HN-65021, HR-720, ICI-D6888, ICI-D7155, ICI-D8731, irbesartan, isoteoline, KRI-1177, KT3-671, KW-3433, losartan, LR-B/057, L-158809, L-158978, L-159282, L-159874, L-161177, L-162154, L-163017, L-159689, L-162234, L-162441, L-163007, LR-B/081, LR B087, LY-285434, LY-302289, LY-315995, LY-235656, LY-301875, ME-3221, olmesartan, PD-150304, PD-123177, PD-123319, RG-13647, RWJ-38970, RWJ-46458, saralasin acetate, S-8307, S-8308, SC-52458, saprisartan, saralasin, sarmesin, SL-91.0102, tasosartan, telmisartan, UP-269-6, U-96849, U-97018, UP-275-22, WAY-126227, WK-1492.2K, YM-31472, WK-1360, X-6803, valsartan, XH-148, XR-510, YM-358, ZD-6888, ZD-7155, ZD-8731, and zolasartan. In some aspects, the additional therapeutic is an ARNI which is selected from the group consisting of sacubitril, valsartan, or a combination of sacubitril and valsartan (sacubitril/valsartan). In some aspects, the additional therapeutic is a SGLT2 which is selected from the group consisting of empaglifozin, dapagliflozin, and sotagliflozin. In some aspects, the additional therapeutic agent improves cardiovascular conditions in the subject. In certain aspects, the additional therapeutic agent is selected from the group consisting of a beta blocker, a diuretic, an angiotensin-converting enzyme (ACE) inhibitor, a calcium channel blocker, an angiotensin II receptor blocker, a mineralocorticoid receptor antagonist, an ARNI, a RAAS inhibitor, an arrhythmia medication, and a SGLT2 inhibitor.

In another aspect, the disclosure provides a method of preventing or treating a disease or disorder in which diastolic dysfunction is present or is an important feature, including, but not limited to, hypertrophic cardiomyopathy (HCM), or a cardiac disorder having a pathophysiological feature of HCM, or a symptom thereof. The method includes administering to a subject in need thereof an effective amount of a compound of formula (I) or pharmaceutically acceptable salt thereof. In yet another aspect, the disease is selected from the group consisting of obstructive HCM, non-obstructive HCM, heart failure with preserved ejection fraction (HFpEF) (including, but not limited to, diabetic HFpEF) and hypertension. The disease may be acute, chronic and/or stable. In yet another aspect, the disease is selected from the group consisting of Class I HCM, Class II nHCM, Class III nHCM, Class II oHCM and Class III oHCM.

In another aspect, the disclosure provides a method of preventing or treating a disease or disorder selected from the group consisting of heart failure with preserved ejection fraction, ischemic heart disease, angina pectoris, and restrictive cardiomyopathy, comprising administering to a subject in need thereof an effective amount of a compound of formula (I), or a pharmaceutically acceptable salt thereof.

In another aspect, the disclosure provides a method of preventing or treating a disease or disorder in which left ventricular hypertrophy due to volume or pressure overload is a feature of the disease, said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy, comprising administering to a subject in need thereof an effective amount of a compound of formula (I), or a pharmaceutically acceptable salt thereof.

In another aspect, the disclosure provides a method of preventing or treating hypertrophic cardiomyopathy (HCM) or a cardiac disorder having a pathophysiological feature associated with HCM, or symptoms thereof, comprising administering to a subject in need thereof an effective amount of a compound of formula (I), or a pharmaceutically acceptable salt thereof, combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The HCM may be obstructive HCM (oHCM) or non-obstructive HCM (nHCM).

In another aspect, provided is a pharmaceutical composition comprising Form 1 polymorph, and a pharmaceutically acceptable excipient.

In another aspect, provided is a method of treating hypertrophic cardiomyopathy (HCM), or a cardiac disorder having a pathophysiological feature of HCM, comprising administering to a subject in need thereof an effective amount of Form 1 polymorph, or a pharmaceutical composition comprising Form 1 polymorph.

In another aspect, provided is a method of treating a disease or disorder characterized by left ventricular hypertrophy due to volume or pressure overload, said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy, comprising administering to a subject in need thereof an effective amount of Form 1 polymorph, or a pharmaceutical composition comprising Form 1 polymorph.

In another aspect, provided is a method of treating hypertrophic cardiomyopathy (HCM), or a cardiac disorder having a pathophysiological feature associated with HCM, comprising administering to a subject in need thereof an effective amount of Form 1 polymorph, or a pharmaceutical composition comprising Form 1 polymorph, combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The disclosure is intended to include all isotopically labeled analogs of the compounds of formula (I). Isotopes include those atoms having the same atomic number but different mass. For example, isotopes of hydrogen include $^2$H(D) and $^3$H(T) and isotopes of carbon include $^{13}$C and $^{14}$C. Isotopically labeled compounds of formula (I) can be prepared according to methods commonly known in the art. Such compounds have various uses as, but not limit to, standards and reagents in determining biological/pharmacological activities. For those stable isotopically labeled compounds of formula (I), they can also favorably modulate biological, pharmacological, or pharmacokinetic properties.

BRIEF DESCRIPTION OF THE DRAWINGS

FIGS. 1A to 1C show X-ray Powder Diffraction (XRPD) data for Form 1 polymorph of the compound of Example 1-3 (also referred to as compound 3).

DETAILED DESCRIPTION OF THE INVENTION

Figure 1A:
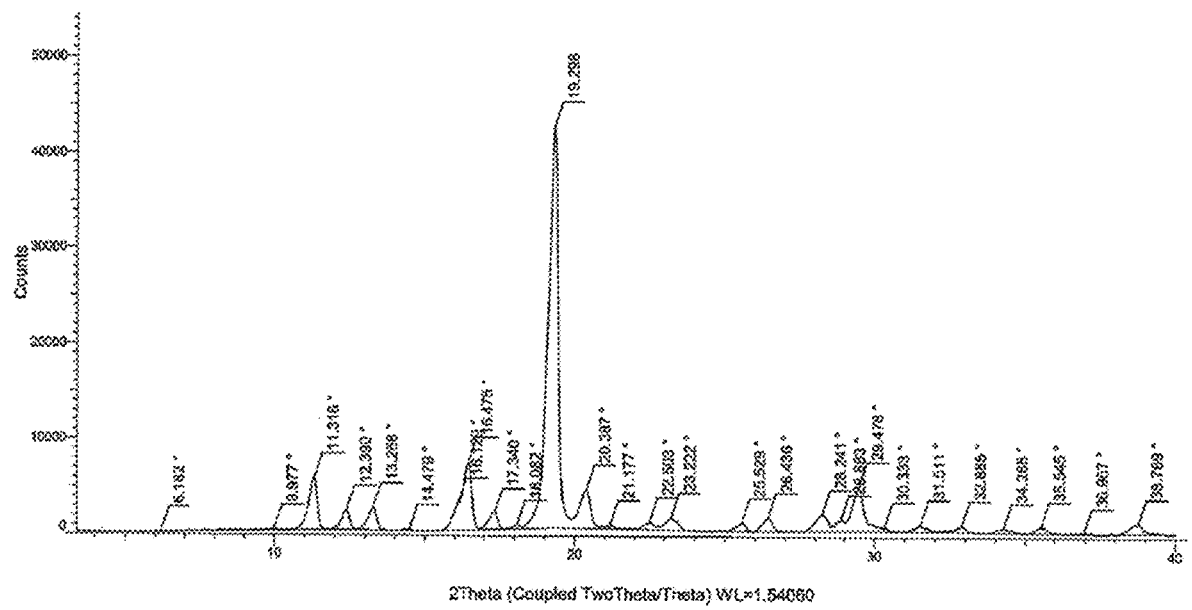
Figure 2:
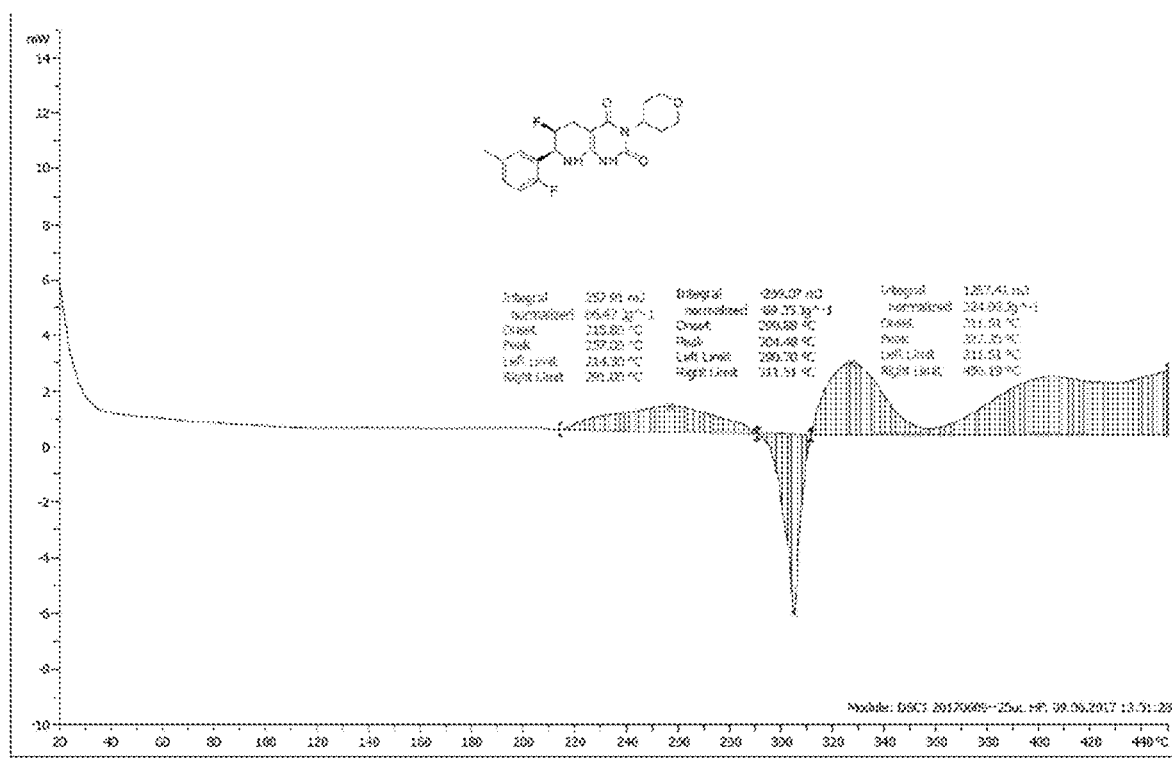
FIG. 2 shows Dynamic Scanning calorimetry (DSC) plot for Form 1 polymorph of the compound of Example 1-3 (also referred to as compound 3).
Figure 3:
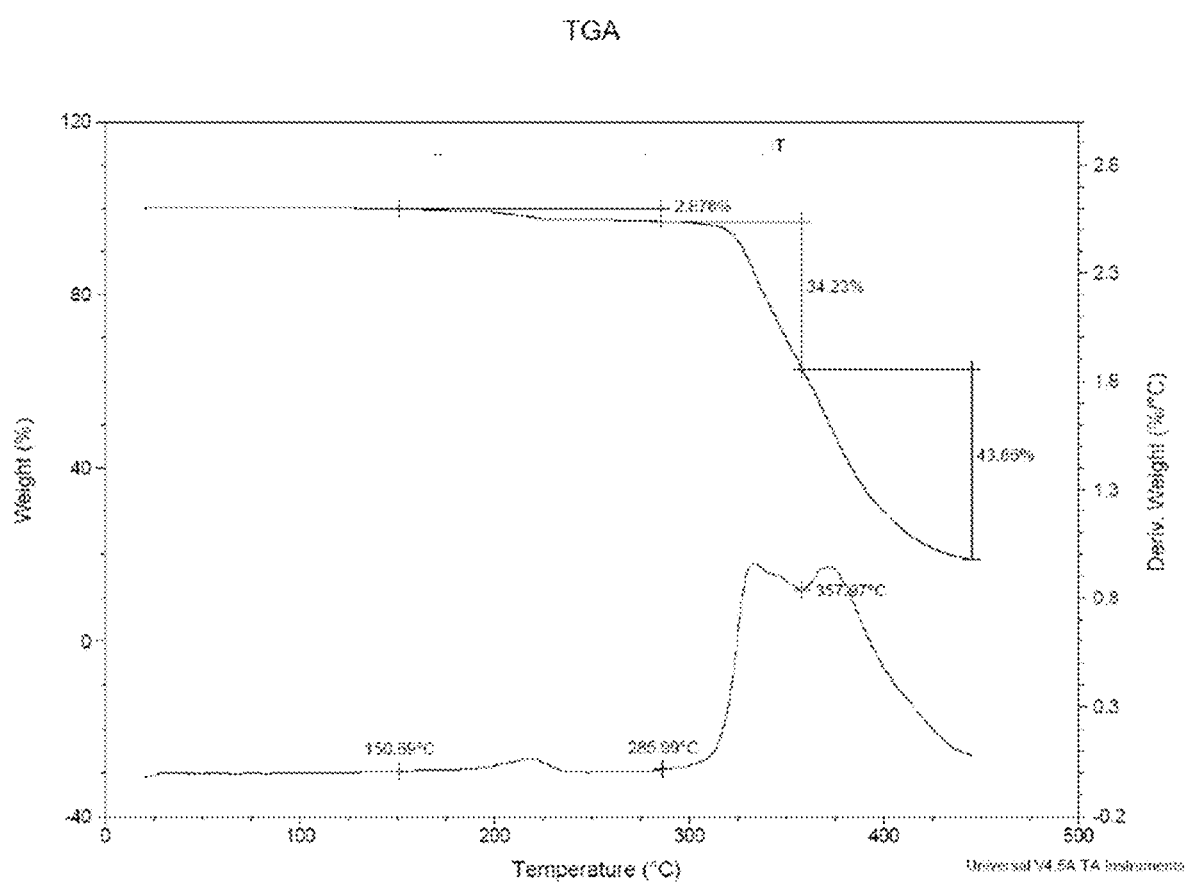
FIG. 3 shows Thermo Gravimetric Analysis (TGA) for Form 1 polymorph of the compound of Example 1-3 (also referred to as compound 3).

A series of tetrahydropyran (THP)-substituted bicyclic pyrimidinedione compounds has been found to reduce excess contractility in hypercontractile states and/or promote cardiac relaxation in hearts with diastolic dysfunction. Without being bound by theory, it is believed that these compounds stabilize the conformation of beta cardiac myosin post-ATP hydrolysis but prior to strongly binding the actin filament and releasing phosphate, thus reducing the proportion of myosin molecules that are available to participate in the "powerstroke" portion of the muscle contraction cycle. As such, the compounds can improve cardiac elasticity, reduce dynamic and/or static left ventricular outflow obstruction, improve diastolic left ventricular relaxation, reduce left ventricular diastolic (filling) pressures, reduce functional mitral regurgitation, and/or reduce left atrial and pulmonary capillary wedge pressures in patients with HCM helping overcome the debilitating exertional dyspnea and/or symptoms referable to left ventricular outflow obstruction (presyncope or syncope) that often accompanies the disease. Preferred compounds of the disclosure have been optimally designed to have a relatively short half-life in humans. For instance, certain compounds of the disclosure are projected to have a half-life of less than 7 days (e.g., less than 5 days, less than 4 days) in humans. The compounds, described herein, have been designed to have a reduced occurrence of reactive metabolites upon testing, reduced dependence on polymorphic CYP enyzmes (such as CYP 2C19) and/or no or reduced risk of CYP induction (such as CYP3A4 induction). Some other benefits of compounds of the disclosure relate to selectivity of inhibition of cardiac myosin as compared to skeletal myosin and/or desirable time-course of effect intensity in response to administration of a drug dose. Furthermore, compounds of the disclosure have beneficial solubility, for example at pH 7.4 a micromolar solubility of over 50, such as over 70. In some cases, the compounds of the disclosure have a micromolar solubility of over 80, such as over 90. The compounds can also be used to treat other cardiac disorders.

The term "about" as used herein is used to describe a range (e.g., of temperatures, of mass, of weight) and is given its ordinary meaning in the art, typically referring to the error associated with an instrument to collect a measurement or reading. In general, the term "about" when referring to temperature provides a deviation of ±0-2° C.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{2-3}$, $C_{2-4}$ and $C_3$-4. For example, $C_{1-4}$ alkyl includes, but is not limited to, methyl, ethyl, propyl, isopropyl, butyl, isobutyl, sec-butyl and tert-butyl. In some instances, alkyl groups are optionally substituted. In some instances, alkyl groups are unsubstituted. In some aspects, alkyl groups are substituted. Alkyl group substituents include, but are not limited to, any of the substituents described herein, that result in the formation of a stable moiety. In certain aspects, the substituent may be one or more hydroxy group. In some such cases, the alkyl group may also be referred to as a hydroxyalkyl group. As used herein, the term "hydroxyalkyl" refers to an alkyl group as provided above, wherein at least one hydrogen atom of the hydrocarbon portion is replaced by a hydroxy group (—OH). Accordingly, "hydroxyalkyl" refers to, for example, hydroxymethyl, 2-hydroxyethyl and 2-hydroxypropyl.

As used herein, the term "alkynyl" refers to an alkyl group that contains one or more triple bonds in the straight or branched aliphatic radical. The one or more carbon-carbon triple bonds can be internal (such as in 2-butynyl) or terminal (such as in 1-butynyl). Examples of alkynyl groups include, without limitation, ethynyl, 1-propynyl, 2-propynyl, 1-butynyl, 2-butynyl, and the like. Alkynyl groups may be substituted or unsubstituted.

As used herein, the term "cycloalkyl" refers to a saturated or partially unsaturated, monocyclic ring containing from 3 or 4 ring atoms, or the number of atoms indicated. Saturated monocyclic cycloalkyl rings include, for example, cyclopropyl or cyclobutyl. Cycloalkyl groups can also be partially unsaturated, having one or more double bonds in the ring. Representative cycloalkyl groups that are partially unsaturated include cyclobutene. Unless otherwise stated, cycloalkyl groups are unsubstituted.

As used herein, the term "alkoxy" refers to an alkyl group having an oxygen atom that connects the alkyl group to the point of attachment: i.e., alkyl-O—. As for the alkyl portions, alkoxy groups can have any suitable number of carbon atoms, such as $C_{1-2}$ or $C_{1-4}$. Alkoxy groups include, for example, methoxy, ethoxy, propoxy, iso-propoxy, butoxy, 2-butoxy, iso-butoxy, sec-butoxy, tert-butoxy, etc. Alkoxy groups may be optionally substituted (unsubstituted or substituted).

As used herein, the terms "halo" and "halogen" refer to fluorine, chlorine, bromine and iodine.

As used herein, the terms "haloalkyl" and "haloalkoxy" refers to the alkyl and alkoxy groups as provided above, wherein at least one hydrogen atom of the hydrocarbon portion is replaced by a halogen atom. Additionally, the terms can also refer to a per-halogenated form of alkyl and alkoxy. Accordingly, "haloalkyl" refers to, for example, fluoromethyl, difluoromethyl, trifluoromethyl, 2,2,2-trifluoroethyl, and chloromethyl. Similarly, "haloalkoxy" refers to, for example, difluoromethoxy, trifluoromethoxy, 2,2,2-trifluoroethoxy, and chloromethoxy.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_3$-6, $C_3$-5, $C_3$-4, $C_4$-6, $C_4$-5, and $C_5$-6 alkyl.

It will be appreciated that the above groups and/or compounds, as described herein, may be optionally substituted with any number of substituents or functional moieties. That is, any of the above groups may be optionally substituted. As used herein the term "optionally substituted" is contemplated to include unsubstituted variants and/or substituted variants (i.e., "optionally substituted" may be used interchangeably with "substituted or unsubstituted"). As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this disclosure, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Furthermore, this disclosure is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, nitrido, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

As used herein, the term "pharmaceutically acceptable" refers to to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A pharmaceutically acceptable substance may be compatible with a compound of formula (I), as well as with any other ingredients with which the compound is formulated.

As used herein, the term "salt" refers to an acid or base salt of a compound of formula (I). Pharmaceutically acceptable salts can be derived, for example, from mineral acids (e.g., hydrochloric acid, hydrobromic acid, phosphoric acid, and the like), organic acids (e.g., acetic acid, propionic acid, glutamic acid, citric acid and the like), and quaternary ammonium ions. It is understood that the pharmaceutically acceptable salts are non-toxic.

Certain aspects of the present compounds may contain one or more basic functional groups and, thus, are capable of forming pharmaceutically-acceptable salts with pharmaceutically-acceptable acids. In such cases, the pharmaceutically-acceptable salts may be relatively non-toxic, inorganic and organic acid addition salts of compounds of the present disclosure. These salts can be prepared in situ in the administration vehicle or the dosage form manufacturing process, or by separately reacting a purified compound of the disclosure in its free base form with a suitable organic or inorganic acid, and isolating the salt thus formed during subsequent purification. Non-limiting examples of salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," *J. Pharm. Sci.* 1977, 66, 1-19)

The pharmaceutically acceptable salts of the compounds, described herein, include the nontoxic salts or quaternary ammonium salts of the compounds, e.g., from non-toxic organic or inorganic acids. For example, such nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In some cases, the compounds of the present disclosure may contain one or more acidic functional groups and, thus, are capable of forming pharmaceutically-acceptable salts with pharmaceutically-acceptable bases. In such cases, the pharmaceutically-acceptable salts may be relatively non-toxic, inorganic and organic base addition salts of compounds of the present disclosure. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine Non-limiting examples of alkali or alkaline earth salts include the lithium, sodium, potassium, calcium, magnesium, and aluminum salts and the like. Non-limiting examples of organic amines useful for the formation of base addition salts include ethylamine, diethylamine, ethylenediamine, ethanolamine, diethanolamine, piperazine and the like.

Additional information on suitable pharmaceutically acceptable salts can be found in Remington's Pharmaceutical Sciences, 17th ed., Mack Publishing Company, Easton, Pa., 1985 and Berge et al., "Pharmaceutical Salts," *J. Pharm. Sci.* 1977, 66, 1-19, which are incorporated herein by reference.

The neutral form of a compound may be regenerated by contacting the salt with a base or acid and isolating the parent compound in the conventional manner. The parent form of the compound may differ from the various salt forms in certain physical properties, such as solubility in polar solvents.

Certain compounds of the present disclosure possess asymmetric carbon atoms (chiral centers) or double bonds; the racemates, diastereomers, geometric isomers, regioisomers and individual isomers (e.g., separate enantiomers) are all intended to be encompassed within the scope of the present disclosure. When a stereochemical depiction is shown, it is meant to refer to the compound in which one of the isomers is present and substantially free of other isomers.

'Substantially free of" other isomers indicates that at least about 80% of the disclosed isomer should be present, based on a molar amount of all isomeric forms of the disclosed isomer present, more preferably at least about 90%, such as about 95% or more. The depicted isomer may be present in an amount of at least about 99%. For example, when a disclosed isomer is provided in a pharmaceutical composition, the composition may comprise at least about 99% of said disclosed isomer in the pharmaceutical composition, based on a total molar amount of all isomeric forms of the disclosed compound present in the pharmaceutical composition (including the disclosed isomeric form and all other isomeric forms).

As used herein, the term "pharmaceutical composition" refers to a product comprising a mixture of the compound of formula (I) and one or more other chemical components. The pharmaceutical composition may comprise an excipient as defined herein, and/or other optional ingredients in specified amounts, as well as any product which results directly or indirectly from combination of the specified ingredients in the specified amounts.

As used herein, the term "excipient" refers to a substance that aids the administration of an active agent to a subject. Pharmaceutical excipients useful in the present disclosure include, but are not limited to, binders, fillers, disintegrants, lubricants, coatings, sweeteners, flavors and colors. One of skill in the art will recognize that other excipients can be useful in the present disclosure.

As used herein, the terms "treat," "treating" and "treatment" refer to any indicia of success in the treatment or amelioration of a pathology, injury, condition, or symptom related to a disease or disorder (for example a cardiac disorder having a pathophysiological feature of HCM), including any objective or subjective parameter such as abatement; remission; diminishing of symptoms; making the pathology, injury, condition, or symptom more tolerable to the patient; or decreasing the frequency or duration of the pathology, injury, condition, or symptom. Treatment or amelioration can be based on any objective or subjective parameter; including, e.g., the result of a physical examination.

As used herein, the terms "prevent," "preventing," or "prevention" refers to a prophylactic treatment of a subject who does not and did not have a pathology, injury, condition, or symptom related to a disease or disorder (for example a cardiac disorder having a pathophysiological feature of HCM) but is at risk of developing the pathology, injury, condition, or symptom or who was with a pathology, injury, condition, or symptom, is not with the pathology, injury, condition, or symptom, but is at risk of regression of the pathology, injury, condition, or symptom. In certain aspects, the subject is at a higher risk of developing the pathology, injury, condition, or symptom or at a higher risk of regression of the pathology, injury, condition, or symptom than an average healthy member of a population. In some aspects, preventing refers to the prevention of the onset of the pathology, injury, condition, or symptom.

An "effective amount" or a "pharmaceutically effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s).

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal A "patient" refers to a human subject in need of treatment of a disease.

Hypertrophic cardiomyopathy (HCM) is identified clinically as unexplained left ventricular (LV) hypertrophy in the absence of known causes such as pressure overload, systemic diseases, or infiltrative processes. One phenotypic hallmark of HCM is myocardial hypercontractility accompanied by reduced LV compliance, reflected clinically as reduced ventricular chamber size, often supranormal ejection fraction, increased wall thickness, and diastolic dysfunction. Some of the symptoms and signs that HCM patients have include, but are not limited to, shortness of breath (especially during exercise), chest pain (especially during exercise), fainting (especially during or just after exercise), sensation of rapid, fluttering or pounding heartbeats, and heart murmur.

Obstructive HCM (oHCM), also known as hypertrophic obstructive cardiomyopathy (HOCM), refers to HCM in the presence of left ventricular outflow tract obstruction (LVOT).

Non-obstructive HCM (nHCM) refers to HCM without outflow tract obstruction at rest or upon provocation.

Heart failure refers to a clinical syndrome that a patient's heart is unable to provide an adequate supply of blood to the body. For some people with heart failure, the heart has difficulty pumping enough blood to support other organs in the body. For others, they may have a hardening and stiffening of the heart muscle itself, which blocks or reduces blood flow to the heart. Heart failure can affect the right or left side of the heart, or both at the same time. It can be either an acute (short-term) or chronic (ongoing) condition. Symptoms of heart failure include, but are not limited to, excessive fatigue, sudden weight gain, a loss of appetite, persistent coughing, irregular pulse, heart palpitations, abdominal swelling, shortness of breath, leg and ankle swelling, protruding neck veins and edema.

Heart failure with preserved ejection fraction (HFpEF), also called diastolic heart failure or diastolic failure refers to heart failure when the heart's ejection fraction is normal (e.g., equal to or greater than 50 percent). Often, heart muscle contracts normally but the ventricles do not relax as they should during ventricular filling, leading to reduced stroke volume.

Stable Diastolic Heart Failure refers to patients with disastolic heart failure who are not having an acute worsening of symptoms. These patients have impaired diastolic function, wherein symptoms can be controlled or stabilized using available therapies.

Diastolic dysfunction refers to abnormal diastole function. Abnormal diastolic function includes impaired left ventricle relaxation, filling, diastolic distensibility, or stiffness. These traits can be measured using echocardiography. Further determining factors for diagnosing diastolic dysfunction using echocardiography are described in J Am Soc Echocardiogr. 29(4):277-314 (2016), the contents of which are incorporated by reference. Left ventricle stiffness can be measured by cardiac magnetic resonance. Cardiac magnetic resonance is used to determine peak filling rate, time to peak filling, and peak diastolic strain rate. Subjects with diastolic dysfunction may also display increased levels of biomarkers in the blood. For example, brain natriuretic peptide (BNP) or N-terminal-pro-brain natriuretic peptide (NT-pro BNP) are present at elevated levels in the blood of individuals with diastolic dysfunction.

Diastolic dysfunction is present or an important feature of a series of diseases including, but not limited to, hypertrophic cardiomyopathy (HCM), heart failure with preserved ejection fraction (HFpEF)—including both disorders of active relaxation and disorders of chamber stiffness (e.g., diabetic HFpEF); ischemic cardiomyopathy, cardiac transplant allograft vasculopathy, restrictive cardiomyopathy (e.g., genetic mutations in one or more sarcomeric protein), inflammatory cardiomyopathy (e.g., Loefllers and EMF), infiltrative cardiomyopathy (e.g., amyloid, sarcoid and XRT), storage diseases (e.g., hemochromatosis, Fabry and glycogen storage disease, congenital heart disease (e.g., pressure-overloaded RV, Tetrology of Fallot (e.g., diastolic dysfunction pre-op and early post-op), and valvular heart disease (e.g., aortic stenosis).

Class I HCM refers to HCM which is Class I according to the New York Heart Association (NYHA).

Class II-III nHCM Refers to nHCM which is Class II or Class III according to the NYHA Class II-III oHCM Refers to oHCM which is Class II or Class III according to the NYHA NYHA Class I refers to a classification wherein a patient or subject has no limitation of physical activity and ordinary physical activity does not cause undue fatigue, palpitation, dyspnea (shortness of breath).

NYHA Class II refers to a classification wherein a patient or subject has slight limitation of physical activity, is comfortable at rest, and ordinary physical activity results in fatigue, palpitation, dyspnea (shortness of breath).

NYHA Class III refers to a classification wherein a patient or subject has marked limitation of physical activity, is comfortable at rest, and less than ordinary activity causes fatigue, palpitation, or dyspnea.

NYHA Class IV refers to a classification wherein a patient or subject is unable to carry on any physical activity without discomfort with symptoms of heart failure at rest, and if any physical activity is undertaken, discomfort increases As used herein "Valsalva gradient" refers to the pressure gradient across LVOT in an individual while this individual is performing a Valsalva maneuver.

III. Compounds

In one aspect, provided herein is a compound having formula (I):

(I)

or a pharmaceutically acceptable salt thereof, wherein
the subscript n is 1 or 2;
each $R^1$ is a member independently selected from the group consisting of fluoro, chloro, $C_1$-$C_4$ alkyl, $C_1$-$C_4$ haloalkyl, $C_1$-$C_4$ alkoxy, $C_1$-$C_4$ haloalkoxy, and $C_2$-$C_4$ alkynyl; wherein at least one $R^1$ is fluoro; and
one of $R^{2a}$ and $R^{2b}$ is fluoro and the other of $R^{2a}$ and $R^{2b}$ is H.

$R^{2a}$ may be fluoro. $R^{2b}$ may be fluoro. $R^{2a}$ may be fluoro when n is 1. $R^{2a}$ may be fluoro when n is 2.

$R^{2b}$ may be fluoro when n is 1. $R^{2b}$ may be fluoro when n is 2.

In one aspect, provided herein is a compound having formula (I):

(I)

or a pharmaceutically acceptable salt thereof, wherein
the subscript n is 1 or 2;
each $R^1$ is a member independently selected from the group consisting of fluoro, chloro, optionally substituted $C_1$-$C_4$ alkyl, optionally substituted $C_1$-$C_4$ haloalkyl, optionally substituted $C_1$-$C_4$ alkoxy, optionally substituted $C_1$-$C_4$ haloalkoxy, and optionally substituted $C_2$-$C_4$ alkynyl; wherein at least one $R^1$ is fluoro; and
one of $R^{2a}$ and $R^{2b}$ is fluoro and the other of $R^{2a}$ and $R^{2b}$ is H.

$R^{2a}$ may be fluoro. $R^{2b}$ may be fluoro. Rea may be fluoro when n is 1. Rea may be fluoro when n is 2. $R^{2b}$ may be fluoro when n is 1. $R^{2b}$ may be fluoro when n is 2.

A pharmaceutically acceptable salt of such compounds of formula (I) is also provided.

In certain aspects, the compound of formula (I) may have the formula:

(Ia)

or a pharmaceutically acceptable salt thereof, wherein the subscript n is 1; and
the $R^1$ is a member independently selected from the group consisting of fluoro, chloro, $C_1$-$C_4$ alkyl, $C_1$-$C_4$ haloalkyl, $C_1$-$C_4$ alkoxy, $C_1$-$C_4$ haloalkoxy, and $C_2$-$C_4$ alkynyl; and
one of $R^{2a}$ and $R^{2b}$ is fluoro and the other of $R^{2a}$ and $R^{2b}$ is H.

In certain aspects, the compound of formula (I) may have the formula:

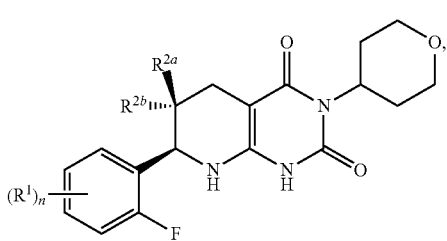

(Ia)

or a pharmaceutically acceptable salt thereof, wherein the subscript n is 1; and
the $R^1$ is a member independently selected from the group consisting of fluoro, chloro, optionally substituted $C_1$-$C_4$ alkyl, optionally substituted $C_1$-$C_4$ haloalkyl, optionally substituted $C_1$-$C_4$ alkoxy, optionally substituted $C_1$-$C_4$ haloalkoxy, and optionally substituted $C_2$-$C_4$ alkynyl; and one of $R^{2a}$ and $R^{2b}$ is fluoro and the other of $R^{2a}$ and $R^{2b}$ is H.

In some instances, n of the compound of formula (I) is 1.
The compound of formula (I) may have the formula:

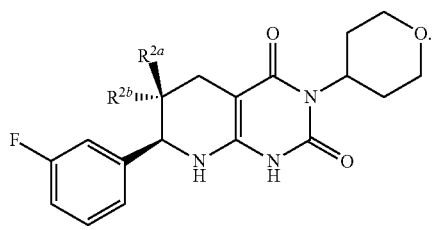

(Ib)

One of $R^{2a}$ and $R^{2b}$ is fluoro and the other of $R^{2a}$ and $R^{2b}$ is H.

A pharmaceutically acceptable salt of such compounds of formula (Ib) is also provided.

In some instances, n of the compound of formula (I) is 2. In some instances where n is 2, one $R^1$ is fluoro and the other may be selected from the group consisting of fluoro, $C_1$-$C_4$ alkyl, $C_1$-$C_4$ alkoxy, and $C_2$-$C_4$ alkynyl; optionally fluoro, methyl, methoxy and ethynyl (—C≡CH), optionally methyl, methoxy and ethynyl (—C≡CH).

In some instances, n of the compound of formula (I) is 2. In some instances where n is 2, one $R^1$ is fluoro and the other may be selected from the group consisting of fluoro, optionally substituted $C_1$-$C_4$ alkyl, optionally substituted $C_1$-$C_4$ alkoxy, and optionally substituted $C_2$-$C_4$ alkynyl; optionally fluoro, methyl, methoxy and ethynyl (—C≡CH), optionally methyl, methoxy and ethynyl (—C≡CH).

The compound of formula (I) may have the formula:

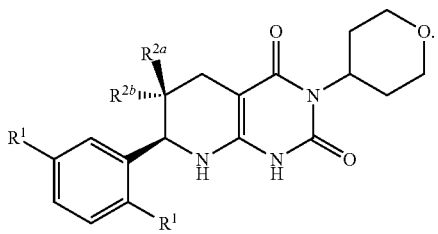

(Ic)

One of $R^{2a}$ and $R^{2b}$ is fluoro and the other of $R^{2a}$ and $R^{2b}$ is H; and
each $R^1$ is a member independently selected from the group consisting of fluoro, chloro, $C_1$-$C_4$ alkyl, $C_1$-$C_4$ haloalkyl, $C_1$-$C_4$ alkoxy, $C_1$-$C_4$ haloalkoxy, and $C_2$-$C_4$ alkynyl.

The compound of formula (I) may have the formula:

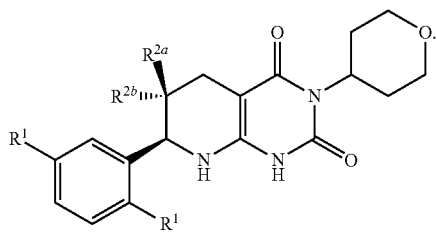

(Ic)

One of $R^{2a}$ and $R^{2b}$ is fluoro and the other of $R^{2a}$ and $R^{2b}$ is H; and
each $R^1$ is a member independently selected from the group consisting of fluoro, chloro, optionally substituted $C_1$-$C_4$ alkyl, optionally substituted $C_1$-$C_4$ haloalkyl, optionally substituted $C_1$-$C_4$ alkoxy, optionally substituted $C_1$-$C_4$ haloalkoxy, and optionally substituted $C_2$-$C_4$ alkynyl.

In some instances, for formula (I) one $R^1$ is fluoro and the other may be selected from the group consisting of fluoro, $C_1$-$C_4$ alkyl, $C_1$-$C_4$ alkoxy, and $C_2$-$C_4$ alkynyl; optionally fluoro, methyl, methoxy and ethynyl (—C≡CH), optionally methyl, methoxy and ethynyl (—C≡CH).

In some instances, for formula (I) one $R^1$ is fluoro and the other may be selected from the group consisting of fluoro, optionally substituted $C_1$-$C_4$ alkyl, optionally substituted $C_1$-$C_4$ alkoxy, and optionally substituted $C_2$-$C_4$ alkynyl. In some instances, for formula (I) one $R^1$ is fluoro and the other may be selected from the group consisting of optionally fluoro, methyl, methoxy and ethynyl (—C≡CH), optionally methyl, methoxy and ethynyl (—C≡CH). In some instances, for formula (I) one $R^1$ is fluoro and the other is a hydroxy substituted alkyl. In some instances, for formula (I) one $R^1$ is fluoro and the other is hydroxymethyl.

A pharmaceutically acceptable salt of such compound of formula (Ic) is also provided.

The compound of formula (I) may have the formula:

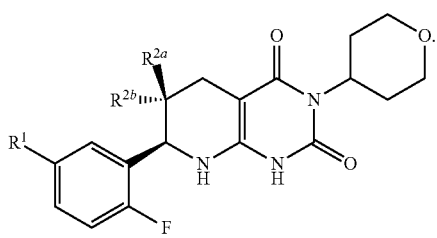

(Id)

$R^1$ may be selected from the group consisting of fluoro, $C_1$-$C_4$ alkyl, $C_1$-$C_4$ alkoxy, and $C_2$-$C_4$ alkynyl; optionally fluoro, methyl, methoxy and ethynyl (—C≡CH), optionally methyl, methoxy and ethynyl (—C≡CH); and
one of $R^{2a}$ and $R^{2b}$ is fluoro and the other of $R^{2a}$ and $R^{2b}$ is H.

The compound of formula (I) may have the formula:

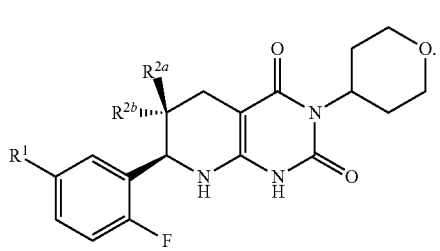
(Id)

R$^1$ may be selected from the group consisting of fluoro, optionally substituted C$_1$-C$_4$ alkyl, optionally substituted C$_1$-C$_4$ alkoxy, and optionally substituted C$_2$-C$_4$ alkynyl; optionally fluoro, methyl, methoxy and ethynyl (—C≡CH), optionally methyl, methoxy and ethynyl (—C≡CH); and one of R$^{2a}$ and R$^{2b}$ is fluoro and the other of R$^{2a}$ and R$^{2b}$ is H. In certain aspects, R$^1$ is hydroxymethyl.

A pharmaceutically acceptable salt of such compound of formula (Id) is also provided.

The compound of formula (I) may have the formula:

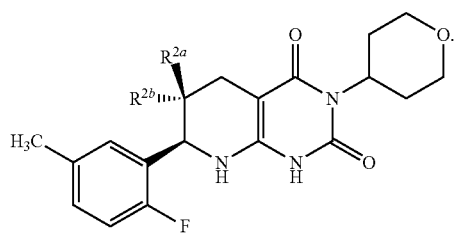
(Ie)

In certain aspects, one of R$^{2a}$ and R$^{2b}$ is fluoro and the other of R$^{2a}$ and R$^{2b}$ is H.

A pharmaceutically acceptable salt of such compound of formula (Ie) is also provided.

The compound of formula (I) may have the formula:

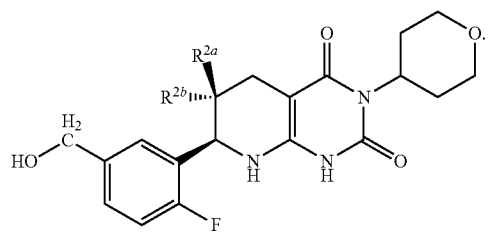

In some aspects, of R$^{2a}$ and R$^{2b}$ is fluoro and the other of R$^{2a}$ and R$^{2b}$ is H. A pharmaceutically acceptable salt of such compound is also provided.

The compound of formula (I) may be of the formula:

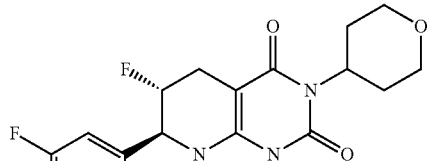

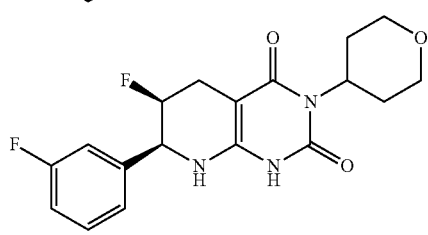

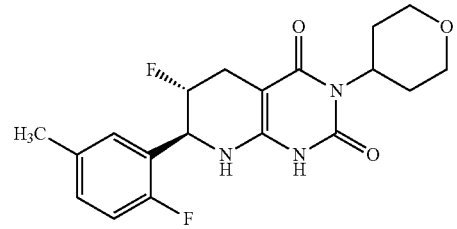

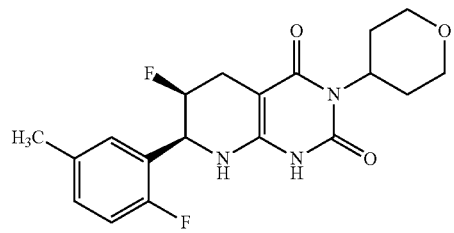

or pharmaceutically acceptable salt thereof.

The compound may be:

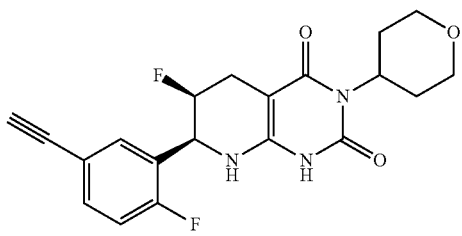 [SMILES: C#Cc1ccc(F)c([C@@H]2Nc3[nH]c(=O)n(C4CCOCC4)c(=O)c3C[C@@H]2F)c1]

or

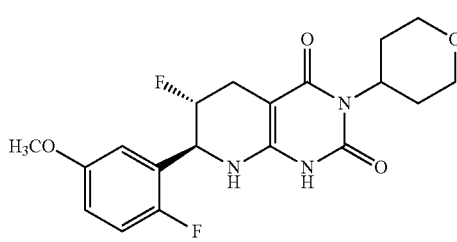

or a pharmaceutically acceptable salt thereof.

The compound may be:

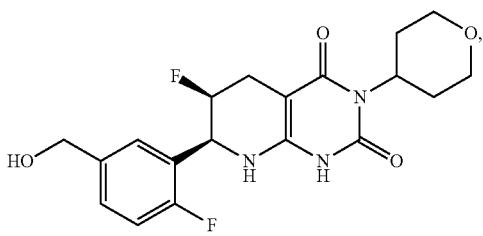

or a pharmaceutically acceptable salt thereof.

The compound disclosed above, or a pharmaceutically acceptable salt thereof, may be provided (e.g. in a pharmaceutical composition) substantially free of other isomers at the carbon atom bearing the phenyl ring (i.e. having an absolute configuration differing from that disclosed and depicted herein). The compound, or a pharmaceutically acceptable salt thereof, may, alternatively or additionally, be provided substantially free of other isomers at the carbon atom bearing fluoro adjacent the carbon atom bearing the phenyl ring. For example, when provided in a pharmaceutical composition, the composition may be substantially free of other isomers at the carbon atom bearing the phenyl ring. Similarly, the composition may, alternatively or additionally, be substantially free of other isomers at the carbon atom bearing fluoro adjacent the carbon atom bearing the phenyl ring. In some aspects, substantially free refers an enantiomeric excess (ee) of ≥95%, ≥98%, ≥99%, or 100% at the carbon atom bearing the phenyl ring. In some aspects, substantially free refers an ee of ≥95%, ≥98%, ≥99%, or 100% at the carbon atom bearing fluoro adjacent the carbon atom bearing the phenyl ring. In some aspects, substantially free refers a diastereomeric excess (de) of ≥95%, ≥98%, ≥99%, or 100%.

In another aspect, provided herein is Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione. Form 1 polymorph is characterized by at least one of:
  a. a powder X-ray diffraction pattern having two or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees;
  b. a DSC thermogram showing endotherms at about 226.05° C., at about 302.47° C., and at about 310.13° C.; or
  c. an X-ray crystal structure substantially the same as in FIG. 4. In another aspect, Form 1 polymorph is characterized by a powder X-ray diffraction pattern having three or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees. In some aspects, Form 1 polymorph is characterized by a powder X-ray diffraction pattern having four or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees. In some aspects, Form 1 polymorph is characterized by a powder X-ray diffraction having peaks expressed in degrees 2-theta±0.2° at each of 11.3, 12.4, and 13.3 degrees. In another aspect, Form 1 polymorph is characterized by a powder X-ray diffraction having peaks expressed in degrees 2-theta±0.2° at each of 11.3, 12.4, 13.3, 16.5, 17.3, 19.3, 20.4, and 29.5 degrees. In another aspect, Form 1 polymorph is characterized by melt onsets of about 221.51° C., about 299.53° C., and about 308.81° C. In some aspects, Form 1 polymorph has a powder X-ray diffraction pattern substantially the same as in FIG. 1A. In some aspects, Form 1 polymorph is substantially free of other forms of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

The compounds of formula (I) can be prepared via any suitable method. Compounds can be prepared, for example, by the route outlined in in the Examples below. One of skill in the art will appreciate that the compounds of formula (I) can be prepared using other synthetic methods, including transformations as described in, for example, Larock (Comprehensive Organic Transformations: A Guide to Functional Group Preparations, Wiley, 1999, which is incorporated herein by reference).

In another aspect, provided herein is a pharmaceutical composition containing a compound of formula (I) or a pharmaceutically acceptable salt thereof. The pharmaceutical composition may comprise a pharmaceutically acceptable excipient. The compositions are useful for treating conditions, such as hypertrophic cardiomyopathy in humans and other subjects. In some aspects, the pharmaceutical composition further comprises an additional agent. Exemplary non-limiting additional agents include agents that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); agents that improve cardiac function by stimulating cardiac contractility (e.g., positive inotropic agents, such as the β-adrenergic agonist dobutamine or the phosphodiesterase inhibitor milrinone); and/or agents that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). In certain aspects, the additional agent in the pharmaceutical composition is a cardiovascular medication. In further aspects, additional exemplary therapeutic agents include a beta adrenergic blocking agent (beta-blocker), renin-angiotensin-aldosterone system (RAAS) inhibitor (e.g., an angiotensin converting enzyme (ACE) inhibitor, an angiotensin receptor antagonist, such as an angiotensin II receptor blocker), an angiotensin receptor neprilysin inhibitor (ARNI) (e.g., sacubitril/valsartan), a mineralocorticoid receptor antagonist (MRA) (e.g., an aldosterone inhibitor such as a potassium-sparing diuretic such as eplerenone, spironolactone, or canrenone), a cholesterol lowering drug (e.g., a statin), a neutral endopeptidase inhibitor (NEPi), a positive inotropic agent (e.g., digoxin, pimobendane, a beta adrenergic receptor agonist such as dobutamine, a phosphodiesterase (PDE)-3 inhibitor such as milrinone, or a calcium-sensitizing agent such as levosimendan), potassium or magnesium, a proprotein convertase subtilisin kexin-type 9 (PCSK9) inhibitor, a vasodilator (e.g., a calcium channel blocker, phosphodiesterase inhibitor, endothelin receptor antagonist, renin inhibitor, or smooth muscle myosin modulator), a diuretic (e.g., furosemide), an arrhythmia medication, an anticoagulant (e.g., warfarin), an antithrombotic agent, an antiplatelet agent, or any combination thereof. Suitable angiotensin II receptor blockers (ARBs) may include, e.g., A-81988, A-81282, BIBR-363, BIBS39, BIBS-222, BMS-180560, BMS-184698, candesartan, candesartan cilexetil, CGP-38560A, CGP-48369, CGP-49870, CGP-63170, CI-996, CV-11194, DA-2079, DE-3489, DMP-811, DuP-167, DuP-532, E-4177, elisartan, EMD-66397, EMD-73495, eprosartan, EXP-063, EXP-929, EXP-3174, EXP-6155, EXP-6803, EXP-7711, EXP-9270, FK-739, GA-0056, HN-65021, HR-720, ICI-D6888, ICI-D7155, ICI-D8731, irbesartan, isoteoline, KRI-1177, KT3-671, KW-3433, losartan, LR-B/ 057, L-158809, L-158978, L-159282, L-159874, L-161177, L-162154, L-163017, L-159689, L-162234, L-162441, L-163007, LR-B/081, LR B087, LY-285434, LY-302289, LY-315995, LY-235656, LY-301875, ME-3221, olmesartan, PD-150304, PD-123177, PD-123319, RG-13647, RWJ-38970, RWJ-46458, saralasin acetate, S-8307, S-8308, SC-52458, saprisartan, saralasin, sarmesin, SL-91.0102, tasosartan, telmisartan, UP-269-6, U-96849, U-97018, UP-275-22, WAY-126227, WK-1492.2K, YM-31472, WK-1360, X-6803, valsartan, XH-148, XR-510, YM-358, ZD-6888, ZD-7155, ZD-8731, and zolasartan. In particular aspects, the additional therapeutic agent may be an ARNI such as sacubitril/valsartan (Entresto®) or a sodium-glucose cotransporter 2 inhibitor (SGLT2), such as empaglifozin (e.g., Jardiance®), dapagliflozin (e.g., Farxiga®), or sotagliflozin. In some aspects, the subject is administered an additional medication for improving cardiovascular conditions in the subject. The additional medication may be, e.g., a beta blocker, a diuretic, an angiotensin-converting enzyme (ACE) inhibitor, a calcium channel blocker, an angiotensin II receptor blocker, a mineralocorticoid receptor antagonist, an ARNI, a RAAS inhibitor, or an arrhythmia medication. In particular aspects, the additional medication is an ANRI such as sacubitril/valsartan or an SGLT2 inhibitor.

In another aspect, provided herein is a pharmaceutical composition comprising Form 1 polymorph. In some aspects, the pharmaceutical composition comprises a pharmaceutically acceptable excipient. In some aspects, provided herein is a pharmaceutical composition, wherein the ratio of the amount of the Form 1 polymorph to the sum of the amounts of other forms is equal to or greater than 80:20. In another case, the ratio of the amount of the Form 1 polymorph to the sum of the amounts of other forms is equal to or greater than 90:10. In certain aspects, the ratio of the amount of the Form 1 polymorph to the sum of the amounts of other forms is equal to or greater than 95:5. In some cases, the ratio of the amount of the Form 1 polymorph to the sum of the amounts of other forms is equal to or greater than 97:3. In certain cases, the ratio of the amount of the Form 1 polymorph to the sum of the amounts of other forms is equal to or greater than 98:2. In some cases, the ratio of the amount of the Form 1 polymorph to the sum of the amounts of other forms is equal to or greater than 99:1.

In some aspects, the pharmaceutical composition comprising Form 1 polymorph further comprises an additional agent. Exemplary non-limiting additional agents include agents that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); agents that improve cardiac function by stimulating cardiac contractility (e.g., positive inotropic agents, such as the β-adrenergic agonist dobutamine or the phosphodiesterase inhibitor milrinone); and/or agents that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). In certain aspects, the additional agent in the pharmaceutical composition is a cardiovascular medication. In further aspects, additional exemplary therapeutic agents include a beta adrenergic blocking agent (beta-blocker), renin-angiotensin-aldosterone system (RAAS) inhibitor (e.g., an angiotensin converting enzyme (ACE) inhibitor, an angiotensin receptor antagonist, such as an angiotensin II receptor blocker), an angiotensin receptor neprilysin inhibitor (ARNI) (e.g., sacubitril/valsartan), a mineralocorticoid receptor antagonist (MRA) (e.g., an aldosterone inhibitor such as a potassium-sparing diuretic such as eplerenone, spironolactone, or canrenone), a cholesterol lowering drug (e.g., a statin), a neutral endopeptidase inhibitor (NEPi), a positive inotropic agent (e.g., digoxin, pimobendane, a beta adrenergic receptor agonist such as dobutamine, a phosphodiesterase (PDE)-3 inhibitor such as milrinone, or a calcium-sensitizing agent such as levosimendan), potassium or magnesium, a proprotein convertase subtilisin kexin-type 9 (PCSK9) inhibitor, a vasodilator (e.g., a calcium channel blocker, phosphodiesterase inhibitor, endothelin receptor antagonist, renin inhibitor, or smooth muscle myosin modulator), a diuretic (e.g., furosemide), an arrhythmia medication, an anticoagulant (e.g., warfarin), an antithrombotic agent, an antiplatelet agent, or any combination thereof. Suitable angiotensin II receptor blockers (ARBs) may include, e.g., A-81988, A-81282, BIBR-363, BIBS39, BIBS-222, BMS-180560, BMS-184698, candesartan, candesartan cilexetil, CGP-38560A, CGP-48369, CGP-49870, CGP-63170, CI-996, CV-11194, DA-2079, DE-3489, DMP-811, DuP-167, DuP-532, E-4177, elisartan, EMD-66397, EMD-73495, eprosartan, EXP-063, EXP-929, EXP-3174, EXP-6155, EXP-6803, EXP-7711, EXP-9270, FK-739, GA-0056, HN-65021, HR-720, ICI-D6888, ICI-D7155, ICI-D8731, irbesartan, isoteoline, KRI-1177, KT3-671, KW-3433, losartan, LR-B/ 057, L-158809, L-158978, L-159282, L-159874, L-161177, L-162154, L-163017, L-159689, L-162234, L-162441, L-163007, LR-B/081, LR B087, LY-285434, LY-302289, LY-315995, LY-235656, LY-301875, ME-3221, olmesartan, PD-150304, PD-123177, PD-123319, RG-13647, RWJ-38970, RWJ-46458, saralasin acetate, S-8307, S-8308, SC-52458, saprisartan, saralasin, sarmesin, SL-91.0102, tasosartan, telmisartan, UP-269-6, U-96849, U-97018, UP-275-22, WAY-126227, WK-1492.2K, YM-31472, WK-1360, X-6803, valsartan, XH-148, XR-510, YM-358, ZD-6888, ZD-7155, ZD-8731, and zolasartan. In particular aspects, the additional therapeutic agent may be an ARNI such as sacubitril/valsartan (Entresto®) or a sodium-glucose cotransporter 2 inhibitor (SGLT2), such as empaglifozin (e.g., Jardiance®), dapagliflozin (e.g., Farxiga®), or sotagliflozin. In some aspects, the subject is administered an additional medication for improving cardiovascular conditions in the subject. The additional medication may be, e.g., a beta blocker, a diuretic, an angiotensin-converting enzyme (ACE) inhibitor, a calcium channel blocker, an angiotensin II receptor blocker, a mineralocorticoid receptor antagonist, an ARNI, a RAAS inhibitor, or an arrhythmia medication. In particular aspects, the additional medication is an ANRI such as sacubitril/valsartan or an SGLT2 inhibitor.

The pharmaceutical compositions for the administration of the compounds of formula (I) or their pharmaceutically acceptable salts or polymorphs provided herein may conveniently be presented in unit dosage form and may be prepared by any of the methods known in the art of pharmacy and drug delivery. All methods include the step of bringing the compound of formula (I), or pharmaceutically acceptable salt thereof, into association with a carrier containing one or more accessory ingredients. In general, the pharmaceutical compositions are prepared by uniformly and intimately bringing the compound of formula (I), or pharmaceutically acceptable salt thereof, into association with a liquid carrier or a finely divided solid carrier or both, and then, if necessary, shaping the product into the desired formulation. In the pharmaceutical composition, the compound of formula (I), or pharmaceutically acceptable salt thereof, is generally included in an amount sufficient to produce the desired effect upon myocardial contractility (e.g., to decrease the often supranormal systolic contractility in HCM) and/or to improve left ventricular relaxation in diastole. Such improved relaxation can alleviate symptoms in hypertrophic cardiomyopathy and/or other etiologies of diastolic dysfunction. The pharmaceutical compositions can, alternatively or additionally, ameliorate the effects of diastolic dysfunction causing impairment of coronary blood flow, thereby improving the latter as an adjunctive agent in angina pectoris and/or ischemic heart disease. The pharmaceutical compositions can, alternatively or additionally, confer benefits on salutary left ventricular remodeling in HCM and/or other causes of left ventricular hypertrophy due to chronic volume or pressure overload from, e.g., valvular heart disease and/or systemic hypertension.

The pharmaceutical compositions containing the compound of formula (I), or pharmaceutically acceptable salt or polymorph thereof, may be in a form suitable for oral use, for example, as tablets, troches, lozenges, aqueous or oily suspensions, dispersible powders or granules, emulsions, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the compound of formula (I), or pharmaceutically acceptable salt thereof, in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Pharmaceutical compositions for oral use may also be presented as gelatin capsules, such as hard gelatin capsules wherein the compound of formula (I), or pharmaceutically acceptable salt thereof or polymorph, is mixed with an inert solid diluent, for example, calcium carbonate, calcium phosphate or kaolin, or as soft gelatin capsules wherein the compound of formula (I), or pharmaceutically acceptable salt thereof, is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the compound of formula (I), or pharmaceutically acceptable salt or polymorph thereof, in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the compound of formula (I), or pharmaceutically acceptable salt or polymorph thereof, in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the compound of formula (I), or pharmaceutically acceptable salt or polymorph thereof, in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions provided herein may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of formula (I) or their pharmaceutically acceptable salts or polymorph provided herein may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds or their pharmaceutically acceptable salts provided herein are employed. As used herein, topical application is also meant to include the use of mouth washes and gargles.

The compounds of formula (I) or their pharmaceutically acceptable salts or polymorph provided herein may also be coupled to a carrier that is a suitable polymer for targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of formula (I) or their pharmaceutically acceptable salts provided herein may be coupled to a carrier that is a biodegradable polymer useful in achieving controlled release of a drug, such as polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

The mutations that lead to HCM cause significant perturbations in myosin mechanics. These mutations exert their effects via distinct mechanisms depending on their locations in the myosin gene. The well-studied HCM mutations, R403Q and R453C, are located in different sections of the motor domain and cause distinct mechanistic perturbations that lead to the common outcome of increased force production. Without wishing to be bound by any particular theory, it is believed that the compounds of formula (I) or their pharmaceutically acceptable salts provided herein can bind directly to the mutant sarcomeric proteins and correct for their aberrant function, either in cis (by affecting the same specific function) or in trans (by altering a complementary function). As such, they can provide therapeutic benefit for HCM patients by counteracting the hypercontractile and/or impaired relaxation associated with this disease.

Accordingly, the disclosure provides a method of treating hypertrophic cardiomyopathy (HCM) or a cardiac disorder having one or more pathophysiological features associated with HCM. The method includes administering to a subject in need thereof an effective amount of a compound provided herein, or a pharmaceutical composition comprising a compound of formula (I) or a pharmaceutically acceptable salt thereof. The method includes administering to a subject in need thereof an effective amount of a compound provided herein, or a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

The disclosure also provides a method of treating hypertrophic cardiomyopathy (HCM) or a cardiac disorder. The method includes administering to a subject in need thereof an effective amount of a compound provided herein, or a pharmaceutical composition comprising a compound of formula (I) or a pharmaceutically acceptable salt thereof. The method includes administering to a subject in need thereof an effective amount of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, or a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

Diastolic dysfunction is present or an important feature of a series of diseases including, but not limited to, hypertrophic cardiomyopathy (HCM), heart failure with preserved ejection fraction (HFpEF)—including both disorders of active relaxation and disorders of chamber stiffness (e.g., diabetic HFpEF); ischemic cardiomyopathy, cardiac transplant allograft vasculopathy, restrictive cardiomyopathy (e.g., genetic mutations in one or more sarcomeric protein), inflammatory cardiomyopathy (e.g., Loefllers and EMF), infiltrative cardiomyopathy (e.g., amyloid, sarcoid and XRT), storage diseases (e.g., hemochromatosis, Fabry and glycogen storage disease, congenital heart disease (e.g., pressure-overloaded RV, Tetrology of Fallot (e.g., diastolic dysfunction pre-op and early post-op), and valvular heart disease (e.g., aortic stenosis).

The present disclosure provides methods of treating a cardiac disease or disorder in a subject in need thereof, comprising administering to the subject an effective amount of a compound, or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione described herein. In some aspects, diastolic dysfunction is a feature of and/or associated with the cardiac disease or disorder. For instance, the cardiac disease or disorder may be cardiomyopathy (e.g., hypertrophic cardiomyopathy), heart failure (e.g., heart failure with preserved ejection fraction, heart failure with midrange ejection fraction), valvular disease (e.g., valvular aortic stenosis), congenital heart disease (e.g., Tetralogy of Fallot), left ventricular hypertrophy, angina pectoris (e.g., refractory angina pectoris), or Chagas disease. In certain aspects, a normal or preserved ejection fraction (e.g., ejection fraction of greater than or equal to about 50%) is a feature of the cardiac disease or disorder. In some such cases, features of the cardiac disease or disorder include a normal or preserved ejection fraction and diastolic dysfunction. For instance, a subject in need of treatment for the cardiac disease or disorder (e.g., HCM, HFpEF, valvular aortic stenosis) may have diastolic dysfunction and an ejection fraction of greater than or equal to about 50%. In certain aspects, a moderate ejection fraction (e.g., ejection fraction of between about 40% and about 50%) is a feature of the cardiac disease or disorder. In some such cases, a subject in need of treatment for the cardiac disease or disorder may have a moderate ejection fraction and diastolic dysfunction. For example, a subject in need of treatment for the cardiac disease or disorder (e.g., heart failure with midrange ejection fraction) may have diastolic dysfunction and an ejection fraction of between about 40% and about 50%.

In some aspects, methods for treating diastolic dysfunction in a subject in need thereof are provided. In some aspects, the method comprises administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to the subject. In some instances, the diastolic dysfunction is left ventricular diastolic dysfunction, right ventricular diastolic dysfunction, or both. The diastolic dysfunction may be chronic, stable, or acute. In some aspects, the subject in need of treatment for diastolic dysfunction may be suffering from one or more diseases or disorders selected from the group consisting of hypertrophic cardiomyopathy (e.g., oHCM, nHCM), restrictive cardiomyopathy, heart failure (e.g., HFpEF, diabetic HFpEF, HFmrEF), infiltrative cardiomyopathy (e.g., due to amyloidosis, sarcoidosis, and/or X-ray therapy), inflammatory cardiomyopathy (e.g., Loeffler endocarditis, endomyocardial fibrosis), hemochromatosis, Fabry disease, glycogen storage disease, congenital heart disease (e.g., Tetralogy of Fallot), valvular heart disease (e.g., aortic stenosis), left ventricular hypertrophy (e.g., due to mitral regurgitation, aortic stenosis, aortic regurgitation, and/or chronic systemic hypertension), hypertension (e.g., chronic, systemic), Chagas disease, and angina pectoris (e.g., refractory angina pectoris). In certain aspects, the subject in need of treatment for diastolic dysfunction may be suffering from one or more diseases or disorders selected from the group consisting of hypertrophic cardiomyopathy (e.g., oHCM, nHCM), heart failure (e.g., HFpEF, diabetic HFpEF, HFmrEF), valvular heart disease (e.g., aortic stenosis), congenital heart disease (e.g., Tetralogy of Fallot), and left ventricular hypertrophy (e.g., due to mitral regurgitation, aortic stenosis, aortic regurgitation, and/or chronic systemic hypertension). In some aspects, the subject in need of treatment for diastolic dysfunction may have undergone one or more surgical procedure. For instance, the subject may have undergone valve replacement surgery (e.g., surgical aortic valve replacement, transcatheter aortic valve replacement) and/or corrective surgery for a congenital heart disease, such as Tetralogy of Fallot. In some aspects, the subject in need of treatment for diastolic dysfunction may an artificial heart valve (e.g., artificial aortic valve). In some cases, the subject in need of treatment for diastolic dysfunction has post-operative diastolic dysfunction. For instance, the subject may have post-operative diastolic dysfunction (e.g., right ventricular diastolic dysfunction) after corrective surgery for a congenital disorder (e.g., Tetralogy of Fallot). In some instances, the subject in need of treatment for diastolic dysfunction has a normal or preserved ejection fraction. In other instances, the subject in need of treatment for diastolic dysfunction has a moderate ejection fraction.

In some aspects, methods for treating a cardiomyopathy (e.g., hypertrophic) in a subject in need thereof are provided.

In certain aspects, the method comprises administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to the subject. Non-limiting examples of cardiomyopathies that may be treated using the compounds described herein include hypertrophic cardiomyopathy (e.g., obstructive cardiomyopathy, non-obstructive cardiomyopathy), restrictive cardiomyopathy, infiltrative cardiomyopathy (e.g., with diastolic dysfunction), and inflammatory cardiomyopathy (e.g., with diastolic dysfunction). In some aspects, the cardiomyopathy is hypertrophic cardiomyopathy. In some instances, the hypertrophic cardiomyopathy is nHCM. The method may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to a subject in need of treatment for nHCM. The subject in need of treatment for nHCM may have NYHA class II, III, or IV heart failure. In other instances, the hypertrophic cardiomyopathy is oHCM. The method may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to a subject in need of treatment for oHCM. The subject in need of treatment for oHCM may have NYHA class II, III, or IV heart failure.

In some aspects, the cardiomyopathy is restrictive cardiomyopathy. The method may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to a subject in need of treatment for restrictive cardiomyopathy. In some aspects, the restrictive cardiomyopathy may be due to, e.g., one or more mutations (e.g., gene mutation) in a sarcomeric protein. In some aspects, the cardiomyopathy is infiltrative cardiomyopathy. The infiltrative cardiomyopathy may be due to amyloidosis, sarcoidosis, and/or X-ray therapy. In some instances, a feature of the infiltrative cardiomyopathy may be diastolic dysfunction. The method of treating infiltrative cardiomyopathy may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4 (1H,3H)-dione to a subject in need thereof. In some aspects, the cardiomyopathy is inflammatory cardiomyopathy. Non-limiting examples of inflammatory cardiomyopathy include Loeffler endocarditis and endomyocardial fibrosis. In some instances, a feature of the inflammatory cardiomyopathy may be diastolic dysfunction. The method of treating inflammatory cardiomyopathy may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to a subject in need thereof.

In some aspects, methods for treating heart failure (e.g., HFpEF, HFmrEF) in a subject in need thereof are provided. The method comprises administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido

[2,3-d]pyrimidine-2,4(1H,3H)-dione to the subject. The heart failure may be left-sided heart failure, right-sided heart failure, or both. The heart failure may be chronic, stable, or acute. The subject in need of treatment for heart failure may have NYHA class II, III, or IV heart failure. Non-limiting examples of heart failure that may be treated using the compounds described herein include HFpEF, diabetic HFpEF, and HFmrEF. In some aspects, the heart failure is HFpEF. In some instances, the subject in need of treatment for HFpEF may have normal or elevated contractility (e.g., as measured by echocardiogram). In some cases, the subject in need of treatment for HFpEF may have an abnormal global longitudinal strain (e.g., less than −15%). In certain aspects, the subject in need of treatment for HFpEF may suffer from diabetes (type I, type II) and/or valvular disease (e.g., aortic stenosis). In some instances, the subject in need of treatment for HFpEF may have an artificial valve (e.g., aortic valve) due to valvular disease (e.g., aortic stenosis). A method of treating HFpEF (e.g., diabetic HFpEF) in a subject in need thereof may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to the subject. In some instances, the heart failure is HFmrEF. The method may comprise administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to a subject in need of treatment for HFmrEF. The subject in need of treatment for HFmrEF may have NYHA class II, III, or IV heart failure.

In some aspects, methods for treating left ventricular hypertrophy in a subject in need thereof are provided. The method comprises administering an effective amount of a compound of Formula (I), or salt thereof, or the Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione to the subject. In some aspects, the subject in need of treatment for left ventricular hypertrophy has an abnormal left ventricular wall thickness. The left ventricular wall thickness in the subject may be greater than normal, but less than a diagnostic criterion for hypertrophic cardiomyopathy. For example, the subject in need of treatment for left ventricular hypertrophy may have a left ventricular wall thickness of greater than about 10 mm (e g, greater than about 11 mm) and less than about 15 mm (e.g., less than or equal to about 14 mm, less than or equal to about 13 mm). In some aspects, the subject in need of treatment for left ventricular hypertrophy has left ventricular hypertrophy in the absence of hypertrophic cardiomyopathy. In certain aspects, the subject in need of treatment for left ventricular hypertrophy may suffer from hypertension (e.g., chronic and/or systemic). In some aspects, the left ventricular hypertrophy may be due to, e.g., chronic mitral regurgitation, chronic aortic regurgitation, chronic aortic stenosis, and/or chronic systemic hypertension.

Further determining factors for diagnosing diastolic dysfunction using echocardiography are described in J Am Soc Echocardiogr. 29(4):277-314 (2016), the contents of which are incorporated herein for all purposes.

Subjects in need of treatment for diastolic dysfunction include subjects from a patient population having non-obstructive hypertrophic cardiomyopathy (nHCM), or subjects having heart failure with preserved ejection fraction (HFpEF). Subjects in need of treatment for diastolic dysfunction include subjects who exhibit left ventricle stiffness as measured by echocardiography or left ventricle stiffness as measured by cardiac magnetic resonance.

In some aspects, the subject in need thereof is from a patient population having HFpEF.

The disclosure also provides a method of treating a disease or disorder selected from the group consisting of diastolic heart failure (for example heart failure with preserved ejection fraction), ischemic heart disease, angina pectoris, and restrictive cardiomyopathy, comprising administering to a subject in need thereof an effective amount of a compound of formula (I), or a pharmaceutically acceptable salt thereof, or a pharmaceutical composition comprising a compound of formula (I) or a pharmaceutically acceptable salt thereof.

The compounds of formula (I) may be administered as a monotherapy or combination therapy. In combination therapy, a compound of formula (I) is used in combination with an additional therapy regimen, e.g., a standard of care (SOC) therapy for the subject's cardiac condition or other therapy useful for treating the relevant disease or disorder. The additional therapeutic agent may be administered by a route and in an amount commonly used for said agent or at a reduced amount, and may be administered simultaneously, sequentially, or concurrently with a compound of formula (I).

In certain aspects, a compound of formula (I) is administered on top of the SOC for a condition of diastolic dysfunction, such as diastolic heart failure. In further aspects, the subject is given, in addition to the compound of formula (I), another therapeutic agent such as a beta-blocker, a RAAS inhibitor (e.g., an angiotensin converting enzyme (ACE) inhibitor, an angiotensin receptor antagonist such as an angiotensin II receptor blocker), an angiotensin receptor neprilysin inhibitor (ARNI) (e.g., sacubitril/valsartan), a mineralocorticoid receptor antagonist (e.g., an aldosterone inhibitor such as a potassium-sparing diuretic such as eplerenone, spironolactone, or canrenone), a cholesterol lowering drug (e.g., a statin), a neutral endopeptidase inhibitor (NEPi), a positive inotropic agent (e.g., digoxin, pimobendane, a beta adrenergic receptor agonist such as dobutamine, a phosphodiesterase (PDE)-3 inhibitor such as milrinone, or a calcium-sensitizing agent such as levosimendan), potassium or magnesium, a proprotein convertase subtilisin kexin-type 9 (PCSK9) inhibitor, a vasodilator (e.g., a calcium channel blocker, phosphodiesterase inhibitor, endothelin receptor antagonist, renin inhibitor, or smooth muscle myosin modulator), a diuretic (e.g., furosemide), an arrhythmia medication, an anticoagulant (e.g., warfarin), an antithrombotic agent, an antiplatelet agent, or any combination thereof.

Suitable ARBs may include, e.g., A-81988, A-81282, BIBR-363, BIBS39, BIBS-222, BMS-180560, BMS-184698, candesartan, candesartan cilexetil, CGP-38560A, CGP-48369, CGP-49870, CGP-63170, CI-996, CV-11194, DA-2079, DE-3489, DMP-811, DuP-167, DuP-532, E-4177, elisartan, EMD-66397, EMD-73495, eprosartan, EXP-063, EXP-929, EXP-3174, EXP-6155, EXP-6803, EXP-7711, EXP-9270, FK-739, GA-0056, HN-65021, HR-720, ICI-D6888, ICI-D7155, ICI-D8731, irbesartan, isoteoline, KRI-1177, KT3-671, KW-3433, losartan, LR-B/057, L-158809, L-158978, L-159282, L-159874, L-161177, L-162154, L-163017, L-159689, L-162234, L-162441, L-163007, LR-B/081, LR B087, LY-285434, LY-302289, LY-315995, LY-235656, LY-301875, ME-3221, olmesartan, PD-150304, PD-123177, PD-123319, RG-13647, RWJ-38970, RWJ-46458, saralasin acetate, S-8307, S-8308, SC-52458, saprisartan, saralasin, sarmesin, SL-91.0102, tasosartan, telmisartan, UP-269-6, U-96849, U-97018, UP-275-22, WAY-126227, WK-1492.2K, YM-31472, WK-1360, X-6803, valsartan, XH-148, XR-510, YM-358, ZD-6888, ZD-7155, ZD-8731, and zolasartan. In particular aspects, the additional therapeutic agent may be an ARNI such as sacubitril/valsartan (Entresto®) or a sodium-glucose cotransporter 2 inhibitor (SGLT2) such as empaglifozin (e.g., Jardiance®), dapagliflozin (e.g., Farxiga®), or sotagliflozin. In some aspects, the subject is administered an additional medication for improving cardiovascular conditions in the subject. The additional medication may be, e.g., a beta blocker, a diuretic, an angiotensin-converting enzyme (ACE) inhibitor, a calcium channel blocker, an angiotensin II receptor blocker, a mineralocorticoid receptor antagonist, an ARNI, a RAAS inhibitor, or an arrhythmia medication. In particular aspects, the additional medication is an ANRI such as sacubitril/valsartan or an SGLT2 inhibitor. In yet another aspect, a subject being treated for heart failure with a compound of formula (I) is also being treated with an ARNI, a beta blocker, and an MRA.

The disclosure also provides a method of treating a disease or disorder selected from the group consisting of diastolic heart failure (for example heart failure with preserved ejection fraction), ischemic heart disease, angina pectoris, and restrictive cardiomyopathy, comprising administering to a subject in need thereof an effective amount of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione The disclosure also provides a method of treating a disease or disorder selected from the group consisting of diastolic heart failure (for example heart failure with preserved ejection fraction), ischemic heart disease, angina pectoris, and restrictive cardiomyopathy, comprising administering to a subject in need thereof an effective amount of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

The Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione may be administered as a monotherapy or combination therapy. In combination therapy, Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione is used in combination with an additional therapy regimen, e.g., a standard of care (SOC) therapy for the subject's cardiac condition or other therapy useful for treating the relevant disease or disorder. The additional therapeutic agent may be administered by a route and in an amount commonly used for said agent or at a reduced amount, and may be administered simultaneously, sequentially, or concurrently with Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione. In certain aspects, Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione is administered on top of the SOC for a condition of diastolic dysfunction, such as diastolic heart failure. In further aspects, the subject is given, in addition to Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, another therapeutic agent such as a beta-blocker, a RAAS inhibitor (e.g., an angiotensin converting enzyme (ACE) inhibitor, an angiotensin receptor antagonist such as an angiotensin II receptor blocker), an angiotensin receptor neprilysin inhibitor (ARNI) (e.g., sacubitril/valsartan), a mineralocorticoid receptor antagonist (e.g., an aldosterone inhibitor such as a potassium-sparing diuretic such as eplerenone, spironolactone, or canrenone), a cholesterol lowering drug (e.g., a statin), a neutral endopeptidase inhibitor (NEPi), a positive inotropic agent (e.g., digoxin, pimobendane, a beta adrenergic receptor agonist such as dobutamine, a phosphodiesterase (PDE)-3 inhibitor such as milrinone, or a calcium-sensitizing agent such as levosimendan), potassium or magnesium, a proprotein convertase subtilisin kexin-type 9 (PCSK9) inhibitor, a vasodilator (e.g., a calcium channel blocker, phosphodiesterase inhibitor, endothelin receptor antagonist, renin inhibitor, or smooth muscle myosin modulator), a diuretic (e.g., furosemide), an arrhythmia medication, an anticoagulant (e.g., warfarin), an antithrombotic agent, an antiplatelet agent, or any combination thereof. Suitable ARBs are provided herein (vide supra). In particular aspects, the additional therapeutic agent may be an ARNI such as sacubitril/valsartan (Entresto®) or a sodium-glucose cotransporter 2 inhibitor (SGLT2) such as empaglifozin (e.g., Jardiance®), dapagliflozin (e.g., Farxiga®), or sotagliflozin. In some aspects along with administration of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, the subject is administered an additional medication for improving cardiovascular conditions in the subject. The additional medication may be, e.g., a beta blocker, a diuretic, an angiotensin-converting enzyme (ACE) inhibitor, a calcium channel blocker, an angiotensin II receptor blocker, a mineralocorticoid receptor antagonist, an ARNI, a RAAS inhibitor, or an arrhythmia medication. In particular aspects, the additional medication is an ANRI such as sacubitril/valsartan or an SGLT2 inhibitor. In yet another aspect, a subject being treated for heart failure with Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4 (1H,3H)-dione is also being treated with an ARNI, a beta blocker, and an MRA.

The disclosure also provides a method of treating a disease or disorder characterized by left ventricular hypertrophy (for example due to volume or pressure overload), said disease or disorder selected from the group consisting of chronic mitral regurgitation, chronic aortic stenosis, and chronic systemic hypertension, combined with therapies aimed at correcting or alleviating the primary cause of volume or pressure overload, including valve repair/replacement or effective antihypertensive therapy, comprising administering to a subject in need thereof an effective amount of a compound of formula (I), or a pharmaceutically acceptable salt thereof. The disclosure also provides a method of treating a disease or disorder characterized by left ventricular hypertrophy (for example due to volume or pressure overload), said disease or disorder selected from the group consisting of chronic mitral regurgitation, chronic aortic stenosis, and chronic systemic hypertension, combined with therapies aimed at correcting or alleviating the primary cause of volume or pressure overload, including valve repair/replacement or effective antihypertensive therapy, comprising administering to a subject in need thereof an effective amount of a pharmaceutical composition comprising a compound of formula (I) or a pharmaceutically acceptable salt thereof.

The disclosure also provides a method of treating a disease or disorder characterized by left ventricular hypertrophy (for example due to volume or pressure overload), said disease or disorder selected from the group consisting of chronic mitral regurgitation, chronic aortic stenosis, and chronic systemic hypertension, combined with therapies aimed at correcting or alleviating the primary cause of volume or pressure overload, including valve repair/replacement or effective antihypertensive therapy, comprising administering to a subject in need thereof an effective amount of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

The disclosure also provides a method of treating a disease or disorder characterized by left ventricular hypertrophy (for example due to volume or pressure overload), said disease or disorder selected from the group consisting of chronic mitral regurgitation, chronic aortic stenosis, and chronic systemic hypertension, combined with therapies aimed at correcting or alleviating the primary cause of volume or pressure overload, including valve repair/replacement or effective antihypertensive therapy, comprising administering to a subject in need thereof an effective amount of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

The disclosure also provides a method of treating hypertrophic cardiomyopathy (HCM), or a cardiac disorder (for example a cardiac disorder having a pathophysiological feature associated with HCM), comprising administering to a subject in need thereof an effective amount of a compound of formula (I), or a pharmaceutically acceptable salt thereof, combined with (1) therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); (2) therapies that improve cardiac function by stimulating cardiac contractility (e.g., positive inotropic agents, such as the β-adrenergic agonist dobutamine or the phosphodiesterase inhibitor milrinone); and/or (3) therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides a method of treating hypertrophic cardiomyopathy (HCM), or a cardiac disorder (for example a cardiac disorder having a pathophysiological feature associated with HCM), comprising administering to a subject in need thereof an effective amount of a pharmaceutical composition comprising a compound of formula (I) or a pharmaceutically acceptable salt thereof, combined with (1) therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); (2) therapies that improve cardiac function by stimulating cardiac contractility (e.g., positive inotropic agents, such as the β-adrenergic agonist dobutamine or the phosphodiesterase inhibitor milrinone); and/or (3) therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides a method of treating hypertrophic cardiomyopathy (HCM), or a cardiac disorder (for example a cardiac disorder having a pathophysiological feature associated with HCM), comprising administering to a subject in need thereof an effective amount of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, combined with (1) therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); (2) therapies that improve cardiac function by stimulating cardiac contractility (e.g., positive inotropic agents, such as the β-adrenergic agonist dobutamine or the phosphodiesterase inhibitor milrinone); and/or (3) therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides a method of treating hypertrophic cardiomyopathy (HCM), or a cardiac disorder (for example a cardiac disorder having a pathophysiological feature associated with HCM), comprising administering to a subject in need thereof an effective amount of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, combined with (1) therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); (2) therapies that improve cardiac function by stimulating cardiac contractility (e.g., positive inotropic agents, such as the β-adrenergic agonist dobutamine or the phosphodiesterase inhibitor milrinone); and/or (3) therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides a compound of formula (I) or pharmaceutically acceptable salt thereof, for use as a medicament. The disclosure also provides a pharmaceutical composition comprising a compound of formula (I) or a pharmaceutically acceptable salt thereof, for use as a medicament. The disclosure also provides Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione for use as a medicament. The disclosure also provides a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use as a medicament.

The disclosure also provides a compound of formula (I) or pharmaceutically acceptable salt thereof for use in the treatment of hypertrophic cardiomyopathy, or a cardiac disorder (for example a cardiac disorder having a pathophysiological feature of HCM). The disclosure also provides a pharmaceutically acceptable salt thereof, for use in the treatment of hypertrophic cardiomyopathy, or a cardiac disorder (for example a cardiac disorder having a pathophysiological feature of HCM). The disclosure also provides Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of hypertrophic cardiomyopathy, or a cardiac disorder (for example a cardiac disorder having a pathophysiological feature of HCM). The disclosure also provides a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of hypertrophic cardiomyopathy, or a cardiac disorder (for example a cardiac disorder having a pathophysiological feature of HCM).

The disclosure also provides a compound of formula (I) or pharmaceutically acceptable salt thereof, for use in the treatment of a disease or disorder selected from the group consisting of diastolic heart failure (for example heart failure with preserved ejection fraction), ischemic heart disease, angina pectoris, and restrictive cardiomyopathy. The disclosure also provides a compound of a pharmaceutical composition comprising a compound of formula (I) or a pharmaceutically acceptable salt thereof, for use in the treatment of a disease or disorder selected from the group consisting of diastolic heart failure (for example heart failure with preserved ejection fraction), ischemic heart disease, angina pectoris, and restrictive cardiomyopathy. The disclosure also provides Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of a disease or disorder selected from the group consisting of diastolic heart failure (for example heart failure with preserved ejection fraction), ischemic heart disease, angina pectoris, and restrictive cardiomyopathy. The disclosure also provides a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of a disease or disorder selected from the group consisting of diastolic heart failure (for example heart failure with preserved ejection fraction), ischemic heart disease, angina pectoris, and restrictive cardiomyopathy.

The disclosure also provides a compound of formula (I) or pharmaceutically acceptable salt thereof, for use in the treatment of disease or disorder characterized by left ventricular hypertrophy (for example due to volume or pressure overload), said disease or disorder selected from the group consisting of chronic mitral regurgitation, chronic aortic stenosis, and chronic systemic hypertension; wherein the compound is for use in combination with therapies aimed at correcting or alleviating the primary cause of volume or pressure overload, including valve repair/replacement or effective antihypertensive therapy. The disclosure also provides a pharmaceutical composition comprising a compound of formula (I) or a pharmaceutically acceptable salt thereof, for use in the treatment of disease or disorder characterized by left ventricular hypertrophy (for example due to volume or pressure overload), said disease or disorder selected from the group consisting of chronic mitral regurgitation, chronic aortic stenosis, and chronic systemic hypertension; wherein the compound is for use in combination with therapies aimed at correcting or alleviating the primary cause of volume or pressure overload, including valve repair/replacement or effective antihypertensive therapy. The disclosure also provides Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of disease or disorder characterized by left ventricular hypertrophy (for example due to volume or pressure overload), said disease or disorder selected from the group consisting of chronic mitral regurgitation, chronic aortic stenosis, and chronic systemic hypertension; wherein the compound is for use in combination with therapies aimed at correcting or alleviating the primary cause of volume or pressure overload, including valve repair/replacement or effective antihypertensive therapy. The disclosure also provides a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of disease or disorder characterized by left ventricular hypertrophy (for example due to volume or pressure overload), said disease or disorder selected from the group consisting of chronic mitral regurgitation, chronic aortic stenosis, and chronic systemic hypertension; wherein the compound is for use in combination with therapies aimed at correcting or alleviating the primary cause of volume or pressure overload, including valve repair/replacement or effective antihypertensive therapy.

The disclosure also provides a compound of formula (I) or pharmaceutically acceptable salt thereof, for use in the treatment of hypertrophic cardiomyopathy (HCM), or a cardiac disorder (for example a cardiac disorder having a pathophysiological feature associated with HCM), wherein the compound is for use in combination with (1) therapies that retard the progression of heart failure by down-regulating neurohormonal stimulation of the heart and attempt to prevent cardiac remodeling (e.g., ACE inhibitors, angiotensin receptor blockers (ARBs), ß-blockers, aldosterone receptor antagonists, or neural endopeptidase inhibitors); (2) therapies that improve cardiac function by stimulating cardiac contractility (e.g., positive inotropic agents, such as the β-adrenergic agonist dobutamine or the phosphodiesterase inhibitor milrinone); and/or (3) therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The disclosure also provides a pharmaceutical composition comprising a compound of formula (I) or a pharmaceutically acceptable salt thereof, for use in the treatment of hypertrophic cardiomyopathy (HCM), or a cardiac disorder (for example a cardiac disorder having a pathophysiological feature associated with HCM), wherein the compound is for use in combination with (1) therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); (2) therapies that improve cardiac function by stimulating cardiac contractility (e.g., positive inotropic agents, such as the β-adrenergic agonist dobutamine or the phosphodiesterase inhibitor milrinone); and/or (3) therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides Form 1 polymorph of (6S, 7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of hypertrophic cardiomyopathy (HCM), or a cardiac disorder (for example a cardiac disorder having a pathophysiological feature associated with HCM), wherein the compound is for use in combination with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The disclosure also provides a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for use in the treatment of hypertrophic cardiomyopathy (HCM), or a cardiac disorder (for example a cardiac disorder having a pathophysiological feature associated with HCM), wherein the compound is for use in combination with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides a use of a compound of formula (I) or pharmaceutically acceptable salt thereof, for the manufacture of a medicament. The disclosure also provides a use of a pharmaceutical composition comprising a compound of formula (I) or a pharmaceutically acceptable salt thereof, for the manufacture of a medicament. The disclosure also provides a use of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione for the manufacture of a medicament. The disclosure also provides a use of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione for the manufacture of a medicament.

The disclosure also provides a use of a compound of formula (I) or pharmaceutically acceptable salt thereof, for the manufacture of a medicament for the treatment of hypertrophic cardiomyopathy, or a cardiac disorder (for example a cardiac disorder having a pathophysiological feature of HCM). The disclosure also provides a use of a pharmaceutical composition comprising a compound of formula (I) or a pharmaceutically acceptable salt thereof, for the manufacture of a medicament for the treatment of hypertrophic cardiomyopathy, or a cardiac disorder (for example a cardiac disorder having a pathophysiological feature of HCM). The disclosure also provides a use of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for the manufacture of a medicament for the treatment of hypertrophic cardiomyopathy, or a cardiac disorder (for example a cardiac disorder having a pathophysiological feature of HCM). The disclosure also provides a use of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for the manufacture of a medicament for the treatment of hypertrophic cardiomyopathy, or a cardiac disorder (for example a cardiac disorder having a pathophysiological feature of HCM).

The disclosure also provides a use of a compound of formula (I) or pharmaceutically acceptable salt thereof, for the manufacture of a medicament for the treatment of a disease or disorder selected from the group consisting of diastolic heart failure (for example heart failure with preserved ejection fraction), ischemic heart disease, angina pectoris, and restrictive cardiomyopathy. The disclosure also provides a use of a pharmaceutical composition comprising a compound of formula (I) or a pharmaceutically acceptable salt thereof, for the manufacture of a medicament for the treatment of a disease or disorder selected from the group consisting of diastolic heart failure (for example heart failure with preserved ejection fraction), ischemic heart disease, angina pectoris, and restrictive cardiomyopathy. The disclosure also provides a use of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for the manufacture of a medicament for the treatment of a disease or disorder selected from the group consisting of diastolic heart failure (for example heart failure with preserved ejection fraction), ischemic heart disease, angina pectoris, and restrictive cardiomyopathy. The disclosure also provides a use of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for the manufacture of a medicament for the treatment of a disease or disorder selected from the group consisting of diastolic heart failure (for example heart failure with preserved ejection fraction), ischemic heart disease, angina pectoris, and restrictive cardiomyopathy.

The disclosure also provides a use of a compound of formula (I) or pharmaceutically acceptable salt thereof for the manufacture of a medicament for the treatment of left ventricular hypertrophy (for example due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy. The disclosure also provides a use of a pharmaceutically acceptable salt thereof, for the manufacture of a medicament for the treatment of left ventricular hypertrophy (for example due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy. The disclosure also provides a use of Form 1 polymorph of (6S,7S)-6-fluoro-7-(2-fluoro-5-methylphenyl)-3-(tetrahydro-2H- pyran-4-yl)-5,6,7,8-tetrahydropyrido[2,3-d]pyrimidine-2,4 (1H,3H)-dione for the manufacture of a medicament for the treatment of left ventricular hypertrophy (for example due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy. The disclosure also provides a use of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for the manufacture of a medicament for the treatment of left ventricular hypertrophy (for example due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy.

The disclosure also provides a use of a compound of formula (I) or pharmaceutically acceptable salt thereof for the manufacture of a medicament for the treatment of hypertrophic cardiomyopathy (HCM), or a cardiac disorder (for example a cardiac disorder having a pathophysiological feature associated with HCM), combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The disclosure also provides a use of a pharmaceutical composition comprising a compound of formula (I) or a pharmaceutically acceptable salt thereof, for the manufacture of a medicament for the treatment of hypertrophic cardiomyopathy (HCM), or a cardiac disorder (for example a cardiac disorder having a pathophysiological feature associated with HCM), combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The disclosure also provides a use of Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione for the manufacture of a medicament for the treatment of hypertrophic cardiomyopathy (HCM), or a cardiac disorder (for example a cardiac disorder having a pathophysiological feature associated with HCM), combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The disclosure also provides a use of a pharmaceutical composition comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, for the manufacture of a medicament for the treatment of hypertrophic cardiomyopathy (HCM), or a cardiac disorder (for example a cardiac disorder having a pathophysiological feature associated with HCM), combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The compounds of formula (I) or their pharmaceutically acceptable salts can alter the natural history of HCM and other diseases rather than merely palliating symptoms. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of formula (I) or their pharmaceutically acceptable salts can specifically target the root causes of the conditions or act upon other downstream pathways. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione can be used to specifically target the root causes of the conditions or act upon other downstream pathways. Accordingly, the compounds of formula (I) or their pharmaceutically acceptable salts can also confer benefit to patients suffering from heart failure with preserved ejection fraction, ischemic heart disease, angina pectoris, or restrictive cardiomyopathy. Accordingly, Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione can also confer benefit to patients suffering from heart failure with preserved ejection fraction, ischemic heart disease, angina pectoris, or restrictive cardiomyopathy. Compounds of formula (I) or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressure the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short and long-term complications. The compounds of formula (I) or their pharmaceutically acceptable salts may reduce the severity of the chronic ischemic state associated with HCM and thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione may reduce the severity of the chronic ischemic state associated with HCM and thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. The compounds of formula (I) or their pharmaceutically acceptable salts could be valuable in reducing or eliminating the need for concomitant medications with their attendant potential toxicities, drug-drug interactions, and/or side effects. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione could be valuable in reducing or eliminating the need for concomitant medications with their attendant potential toxicities, drug-drug interactions, and/or side effects. The compounds of formula (I) or their pharmaceutically acceptable salts may reduce interstitial myocardial fibrosis and/or slow the progression, arrest, or reverse left ventricular hypertrophy. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione may reduce interstitial myocardial fibrosis and/or slow the progression, arrest, or reverse left ventricular hypertrophy.

Depending on the disease to be treated and the subject's condition, the compounds of formula (I) or their pharmaceutically acceptable salts provided herein may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

Depending on the disease to be treated and the subject's condition, Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione provided herein may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The compounds of formula (I) or pharmaceutically acceptable salts thereof, or pharmaceutical compositions comprising compounds of formula (I) or pharmaceutically acceptable salts thereof, may be administered on a regimen of 1 to 4 times per day, preferably once or twice per day. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, or pharmaceutical compositions comprising Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione, may be administered on a regimen of 1 to 4 times per day, preferably once or twice per day.

It will be understood, however, that the specific dose level and frequency of dosage for any particular patient may be varied and will depend upon a variety of factors including the activity of the specific compound, or pharmaceutically acceptable salt, employed, the metabolic stability and length of action of that compound or pharmaceutically acceptable salt thereof, the age, body weight, hereditary characteristics, general health, sex and diet of the subject, as well as the mode and time of administration, rate of excretion, drug combination, and the severity of the particular condition for the subject undergoing therapy.

Compounds of formula (I), pharmaceutically acceptable salts of compounds of formula (I) and/or pharmaceutical compositions provided herein may be used in combination with other drugs that are used in the treatment, prevention, suppression or amelioration of the diseases or conditions for which compounds and compositions provided herein are useful. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione and/or pharmaceutical compositions provided herein may be used in combination with other drugs that are used in the treatment, prevention, suppression or amelioration of the diseases or conditions for which compounds and compositions provided herein are useful. Such other drugs may be administered, by a route and in an amount commonly used therefor, contemporaneously or sequentially with a compound or composition provided herein. When a compound or composition provided herein is used contemporaneously with one or more other drugs, a pharmaceutical composition containing such other drugs in addition to the compound or composition provided herein is preferred. Accordingly, the pharmaceutical compositions provided herein include those that also contain one or more other active ingredients or therapeutic agents, in addition to a compound or composition provided herein. Suitable additional active agents include, for example: therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators). The weight ratio of the compound of formula (I), or pharmaceutically acceptable salt thereof, provided herein to the second active ingredient may be varied and will depend upon the effective dose of each ingredient. Generally, an effective dose of each will be used.

Where a compound of the disclosure is administered in combination with another therapeutic agent, the other therapeutic agent can be administered simultaneously, separately or sequentially with the compound of formula (I). The precise dosage regimen being commensurate with the properties of the therapeutic agent(s). Where a compound of the disclosure is administered in combination with another therapeutic agent, the other therapeutic agent can be administered simultaneously, separately or sequentially with Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione. The precise dosage regimen being commensurate with the properties of the therapeutic agent(s).

EXAMPLES

Abbreviations: ACN: acetonitrile; aq: aqueous; Ar: argon; $CH_2Cl_2$: dichloromethane; $CH_3CN$: acetonitrile; $CH_3OH$: methanol; $Cs_2CO_3$: cesium carbonate; DCM: dichloromethane; DIEA: diisopropyl ethylamine; DMF: dimethyl formamide; DMSO: dimethyl sulfoxide; equiv.: equivalent(s); $Et_2O$: diethyl ether; EtOAc: ethyl acetate; EtOH: ethanol; h or hr: hour(s); HATU: 1-[bis(dimethylamino)methylene]-1H-1,2,3-triazolo[4,5-b]pyridinium 3-oxid hexafluorophosphate, N-[(dimethylamino)-1H-1,2,3-triazolo-[4,5-b]pyridin-1-ylmethylene]-N-methylmethanaminium hexafluorophosphate N-oxide; HCl: hydrogen chloride; $H_2O$: water; IPA: isopropyl alcohol; $iPr_2O$: diisopropyl ether; $K_2CO_3$: potassium carbonate; LiHMDS: lithium hexamethyldisilazane; MeOH: methanol; $MgSO_4$: magnesium sulfate; min: minutes; mL: milliliter; MW or μW: microwave (reaction done in microwave reactor); $NaBH_4$: sodium borohydride; $NaBH_3CN$: sodium cyanoborohydride; NaCl: sodium chloride; $NaBH_{3CN}$: sodium cyanoboro hydride; NaH: sodium hydride; $NaHCO_3$: sodium bicarbonate; NaOH: sodium hydroxide; NaOMe: sodium methoxide; $Na_2SO_4$: sodium sulfate; n-BuOH: n-butanol; $NH_4Cl$: ammonium chloride; pH: –log [$H^+$]; RT: room temperature; $SOCl_2$: thionyl chloride; TFA: trifluoroacetic acid; THF: tetrahydrofuran; THP, tetrahydropyran or tetrahydropyranyl; and Zn: zinc powder. All of the experiments were carried out in fume hoods with specific safety precautions and necessary personal protective equipment.

Example 1: Synthesis

Intermediate Example 1: Preparation of (S)-3-(((S)-tert-butylsulfinyl)amino)-2,2-difluoro-3-(3-fluorophenyl)propanoic acid (1-4)

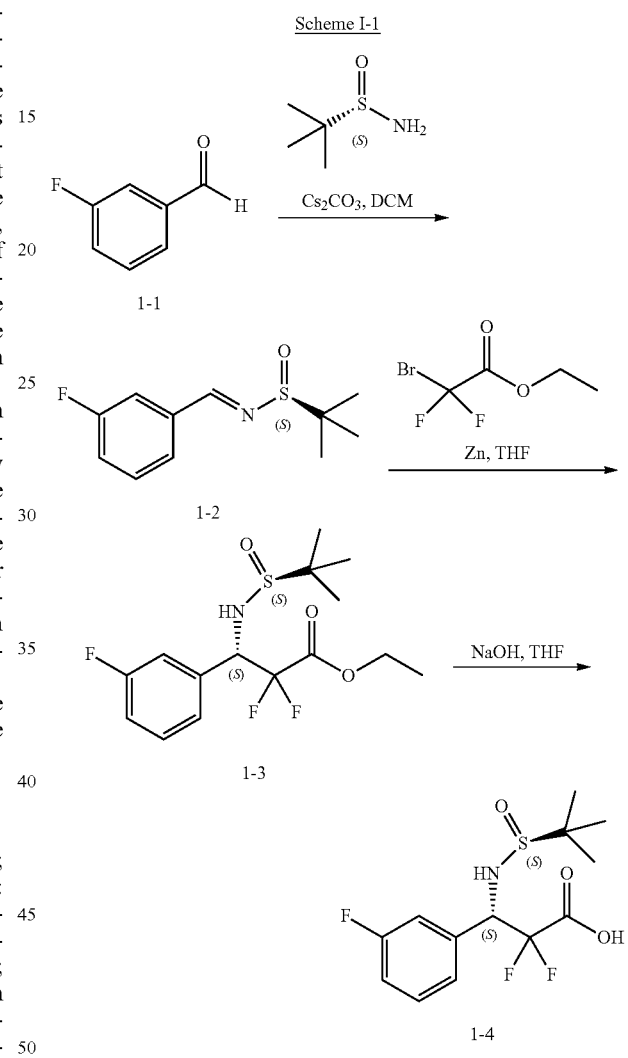

Step 1. Synthesis of (S,E)-N-(3-fluorobenzylidene)-2-methylpropane-2-sulfinamide (1-2). To a 1000-mL round-bottom flask were added 3-fluorobenzaldehyde (50 g, 0.40 mol), (S)-2-methylpropane-2-sulfinamide (50 g, 0.41 mol), $Cs_2CO_3$ (157 g, 0.48 mol), and dichloromethane (500 mL) under an atmosphere of Ar. After stirring at rt for 4 h, the reaction mixture was diluted with methyl tert-butylether (MTBE) (1000 mL). Subsequently, the mixture was filtered, and the filtrate was concentrated to give crude 1-2 (87 g, 95%) as an off-while solid, which was used for the next step without further purification. LC-MS (ES, m/z): 228 [M+H]$^+$; $^1$H NMR (300 MHz, CDCl$_3$): δ 8.55 (d, 1H), 7.63-7.48 (m, 2H), 7.41-7.48 (td, J=8.0, 5.5 Hz, 1H), 7.17-7.7.26 (m, 1H), 1.26 (d, J=2.6 Hz, 9H).

Step 2. Synthesis of ethyl (S)-3-(((S)-tert-butylsulfinyl)amino)-2,2-difluoro-3-(3-fluorophenyl)propanoate (1-3). To a suspension of Zn (38 g, 0.58 mmol) in tetrahydrofuran (600 mL) was added a solution of 1-2 (53.5 g, 0.24 mol) and ethyl 2-bromo-2, 2-difluoroacetate (120 g, 0.59 mol) in tetrahydrofuran (250 mL) at 70° C. with stirring for 40 min under an atmosphere of Ar. After stirring at 70° C. for another 30 min, the reaction mixture was filtered, and the filtrate was concentrated. The residue was diluted with EtOAc (1000 mL). Next, the resulting mixture was washed with sat. aq. citric acid (500 mL) and dried over anhydrous $Na_2SO_4$. The solvent was removed and the residue was dried in vacuo to give 1-3 (50 g, 60%) as a yellow oil. LC-MS (ES, m/z): 352 $[M+H]^+$.

Step 3. (S)-3-(((S)-tert-butylsulfinyl)amino)-2,2-difluoro-3-(3-fluorophenyl)propanoic acid (1-4). A solution of 1-3 (80 g, 0.23 mol) in tetrahydrofuran (1000 mL) was added 1 N aq. NaOH (350 mL) at rt under an atmosphere of Ar. After stirring at rt for 30 min, the pH value of the reaction mixture was adjusted to 5 with 1 N aq. citric acid. The resulting mixture was extracted with ethyl acetate (1000 mL×3). Next, the combined organic extracts were washed with brine (500 mL) and dried over anhydrous $Na_2SO_4$. The solvent was removed and the residue was purified by Flash-Prep-HPLC (column: C18 silica gel; mobile phase: $CH_3CN/H_2O$=10/90 (v/v) increasing to $CH_3CN/H_2O$=95/5 (v/v) over 60 min; detector: UV 254 nm) to give 1-4 (30 g, 41%) as a white solid. LC-MS (ES, m/z): 324 $[M+H]^+$; $^1H$-NMR (400 MHz, $d^6$-DMSO): δ 14.97 (s, 1H), 7.48-7.36 (m, 2H), 7.32 (d, J=7.8 Hz, 1H), 7.23-7.13 (m, 1H), 6.56 (d, J=10.1 Hz, 1H), 4.98 (m, 1H), 1.01 (s, 9H).

Intermediate Example 2: Preparation of 1-(tetrahydro-2H-pyran-4-yl)piperidine-2,4,6-trione (2-3)

pension was filtered and the solid was washed with ether (500 mL×3) and dried in vacuo to give 2-2 (34 g, 68%) as a white solid. $^1H$ NMR (300 MHz, $d^6$-DMSO): δ 5.96 (d, J=7.8 Hz, 1H), 5.37 (s, 2H), 3.79 (m, 2H), 3.63-3.43 (m, 1H), 3.32 (m, 2H), 1.70 (m, 2H), 1.29 (m, 2H).

Step 2. Synthesis of 1-(tetrahydro-2H-pyran-4-yl)piperidine-2,4,6-trione (2-3). To a solution of NaOMe (20 g, 0.38 mol) in MeOH (3000 mL) was added 2-2 (34 g, 0.24 mol), followed by 1,3-dimethyl propanedioate (470 g, 0.36 mol) at rt under an atmosphere of Ar. After stirring at 80° C. overnight, the reaction mixture was concentrated and the residue was dilute with water (50 mL). Subsequently, the pH value of the resulting mixture was adjusted to 2 by adding concd. aq. HCl at 0° C. The suspension was filtered and the solid was washed with water and dried in vacuo at 45° C. for 24 h to give 2-3 (30 g, 60%) as a white solid. $^1H$ NMR (300 MHz, $d^6$-DMSO): δ 11.25 (s, 1H), 4.69 (m, 1H), 3.91 (m, 2H), 3.60 (s, 2H), 3.33 (m, 2H), 2.43 (m, 2H), 1.59-1.40 (m, 2H).

Step B-1. Synthesis of phenyl carbamate (2-5). To a mixture of sat. aq ammonia (50 mL) and DCM (50 mL) was added a solution of 2-4 (30 g) in DCM (45 mL) at 0° C. After stirring at 0° C. for 4 h, the reaction mixture was filtered and the solid was washed with water and dried in vacuo at 45° C. for 12 h to give 2-5 (18.3 g, 70%) as a white solid. LC-MS (ES, m/z): 138 $[M+H]^+$; $^1H$ NMR (400 MHz, $d^6$-DMSO): δ 7.42-7.32 (m, 2H), 7.24-7.15 (m, 1H), 7.13-7.04 (m, 2H), 6.89 (br, 2H).

Step B-2. Synthesis of 1-(tetrahydro-2H-pyran-4-yl)urea (2-2) (Method B). A mixture of 2-5 (18.3 g, 0.13 mol), DIEA (17.3 g, 0.13 mol), and 2-1 (13.5 g, 0.13 mol) in THF (130 mL) was stirred at 70° C. for 3 h under an atmosphere of Ar.

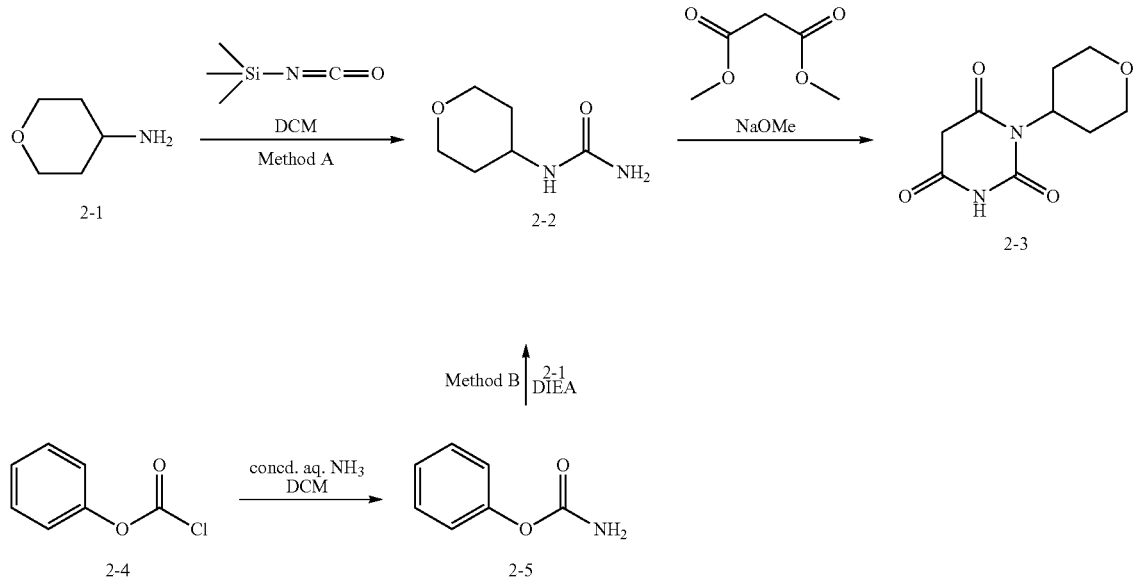

Scheme I-2

Step A-1. Synthesis of 1-(tetrahydro-2H-pyran-4-yl)urea (2-2) (Method A). To a solution of 2-1 (24 g, 0.24 mol) in DCM (3000 mL) was added isocyanatotrimethylsilane (30 g, 0.26 mol) at 0° C. under an atmosphere of Ar. After stirring at rt overnight, the reaction was quenched by adding MeOH (20 mL). The solvent was removed and the residue was triturated with ether (50 mL). Subsequently, the sus- Subsequently, the suspension was filtered and the solid was washed with ether (100 mL) and dried in vacuo at 45° C. for 12 h to give 2-2 (18.3 g, 95%) as a white solid. $^1H$ NMR (400 MHz, $d^6$-DMSO): δ 5.96 (d, J=7.8 Hz, 1H), 5.37 (s, 2H), 3.78 (m, 2H), 3.51 (m, 1H), 3.32 (m, 2H), 1.69 (m, 2H), 1.28 (m, 2H).

Intermediate Example 3: Preparation of (2R,3S)-3-(((R)-tert-butylsulfinyl)amino)-2-fluoro-3-(3-fluorophenyl)propanoic acid (3-3)

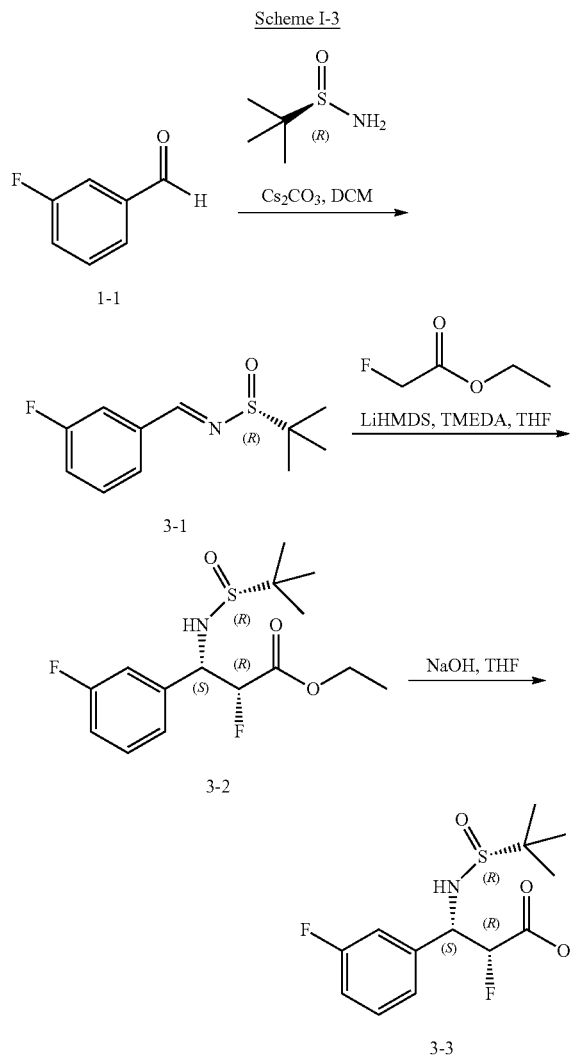

Step 1. Synthesis of (R,E)-N-(3-fluorobenzylidene)-2-methylpropane-2-sulfinamide (4-1). A mixture of 1-1 (5.0 g, 40.3 mmol), (R)-2-methylpropane-2-sulfinamide (5.1 g, 42.2 mmol), and Cs$_2$CO$_3$ (15.7 g, 48.25 mol) in DCM (60 mL) was stirred at rt overnight under an atmosphere of Ar. Subsequently, the reaction mixture was diluted with ether (200 mL) and then filtered. The filtrate was concentrated and the residue was dried in vacuo to give crude 3-1 (10 g) as a white solid, which was used in the next step without further purification. LC-MS (ES, m/z): 228 [M+H]$^+$; $^1$H NMR (300 MHz, d$^6$-DMSO): δ 8.58 (s, 1H), 7.88-7.73 (m, 2H), 7.60 (m, 1H), 7.45 (m, 1H), 1.19 (s, 9H).

Step 2. Synthesis of ethyl (2R,3S)-3-(((R)-tert-butylsulfinyl)amino)-2-fluoro-3-(3-fluorophenyl)propanoate (3-2). To a solution of crude 3-1 (3.0 g, 13.2 mmol), TMEDA (3.6 mL), and ethyl 2-fluoroacetate (2.1 g, 19.8 mol) in THF (30 mL) was added LiHMDS (1M in THF, 19.8 mL) dropwise at −78° C. over 30 min under an atmosphere of Ar. After stirring at −78° C. for 1 h, the reaction was quenched by adding 2 N aq. HCl (45 mL) at −78° C. The reaction mixture was concentrated to remove most of THF and then extracted with EtOAc (100 mL×3). Subsequently, the combined organic extracts were washed with brine and dried over anhydrous Na$_2$SO$_4$. The solvent was removed and the residue was dried in vacuo to give crude 3-2 (4.6 g) as an off-white solid, which was used for the next step without further purification. LC-MS (ES, m/z): 334 [M+H]$^+$.

Step 3. Synthesis of (2R,3S)-3-(((R)-tert-butylsulfinyl)amino)-2-fluoro-3-(3-fluorophenyl)propanoic acid (3-3). To a solution of crude 3-2 (6 g, 18 mmol) in THF (60 mL) was added 1N aq. NaOH (36 mL, 36 mmol) at rt. After stirring at rt overnight, the reaction mixture was diluted with water (100 mL). The resulting mixture was extracted with EtOAc (100 mL×2). The aqueous layer was adjusted to pH 5 with sat. aq. citric acid and the resulting mixture was extracted with EtOAc (200 mL×3). Next, the combined organic extracts were washed with brine (100 mL) and dried over anhydrous Na$_2$SO$_4$. The solvent was removed and the residue was purified by preparative HPLC (column: XBridge Prep OBD C18 column, 19×250 mm, 5um; mobile phase: water (0.05% TFA (v/v)) and ACN (3.0% (v/v) up to 17.0% (v/v) in 8 min); detector: UV 220 nm) to give 3-3 (1.5 g, 27%) as a white solid. LC-MS (ES, m/z): 306 [M+H]$^+$; $^1$H NMR (400 MHz, d$^6$-DMSO): δ 12.83 (s, 1H), 7.53-7.44 (m, 1H), 7.42-7.35 (m, 2H), 7.12 (m, 1H), 6.12 (d, J=10.7 Hz, 1H), 5.33 (m, 1H), 4.86 (m, 1H), 1.14 (s, 9H).

Comparative Example 1: Preparation of (S)-6,6-difluoro-7-(3-fluorophenyl)-3-(tetrahydro-2H-pyran-4-yl)-5,6,7,8-tetrahydropyrido[2,3-d]pyrimidine-2,4(1H,3H)-dione (C-1)

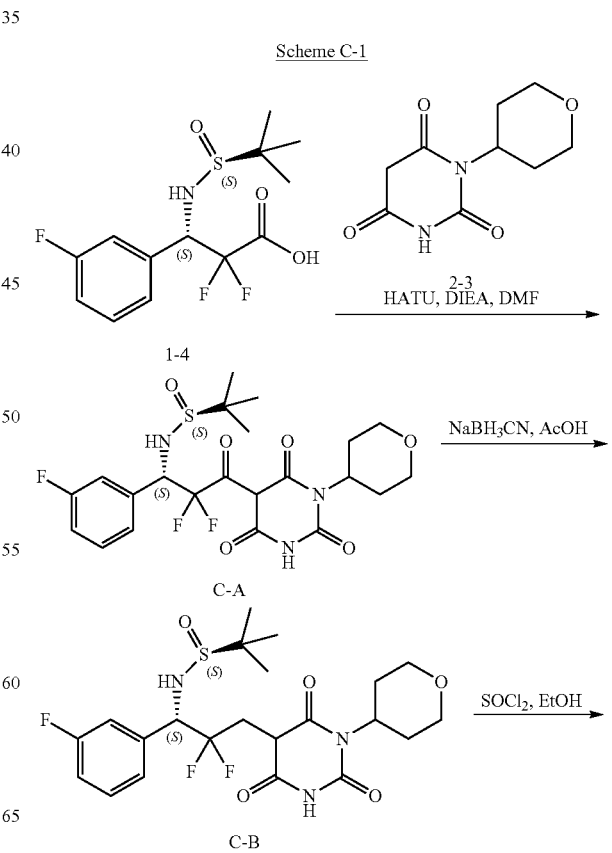

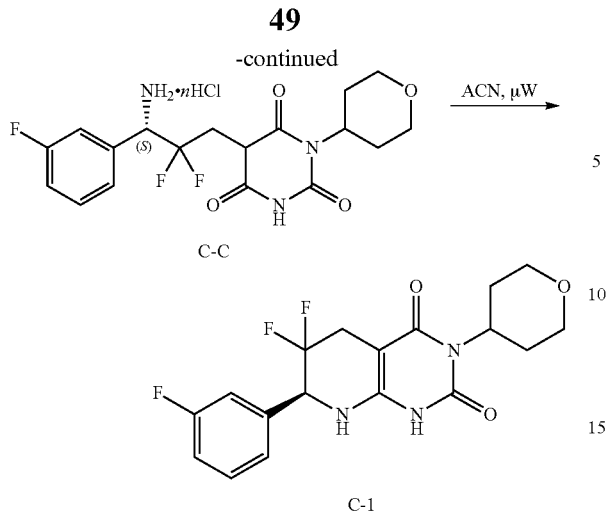

Step 1. Synthesis of (S)—N-((1S)-2,2-difluoro-1-(3-fluorophenyl)-3-oxo-3-(2,4,6-trioxo-1-(tetrahydro-2H-pyran-4-yl)hexahydropyrimidin-5-yl)propyl)-2-methylpropane-2-sulfinamide (C-A). To a solution of 1-4 (2.69 g, 8.32 mmol), HATU (4.75 g, 12.49 mmol), and 2-3 (2.65 g, 12.49 mmol) in DMF (30 mL) was added DIEA (2.15 g, 16.63 mmol) dropwise at 0° C. After stirring at rt overnight, the reaction mixture was diluted with sat. aq. NaHCO$_3$ (100 mL) and ice water (100 mL). The mixture was extracted with EtOAc (100 mL×3) and the combined organic extracts were washed with brine and dried over anhydrous Na$_2$SO$_4$. The solvent was removed and the residue was dried in vacuo to give crude C-A (1.23 g, 29%) as a yellow solid, which was used for the next step without further purification. LC-MS (ES, m/z): 518 [M+H]$^+$.

Step 2. Synthesis of (S)—N-((1S)-2,2-difluoro-1-(3-fluorophenyl)-3-(2,4,6-trioxo-1-(tetrahydro-2H-pyran-4-yl)hexahydropyrimidin-5-yl)propyl)-2-methylpropane-2-sulfinamide (C-B). A mixture of C-A (1 g, 1.93 mmol) and sodium cyanoborohydride (606.8 mg, 9.66 mmol) in acetic acid (15 mL) was stirred at rt for 1 h. Subsequently, the reaction mixture was diluted with ice water (50 mL) and extracted with EtOAc (50 mL×3). The combined organic extracts were washed with brine and dried over anhydrous Na$_2$SO$_4$. The solvent was removed and the residue was dried in vacuo to give crude C-B (1.28 g) as a white solid, which was used for the next step without further purification. LC-MS (ES, m/z): 504 [M+H]$^+$.

Step 3. Synthesis of 5-((S)-3-amino-2, 2-difluoro-3-(3-fluorophenyl)propyl)-1-(tetrahydro-2H-pyran-4-yl)pyrimidine-2,4,6(1H, 3H, 5H)-trione (C-C). To a solution of crude C-B (1.28 g) in ethanol (18 mL) was added thionyl chloride (2.7 mL) at 0° C. over 3 min. After stirring at rt for 1 h, the reaction mixture was concentrated and dried in vacuo to give crude C-C (800 mg) as a yellow solid, which was used for the next step without further purification. LC-MS (ES, m/z): 400 [M+H]$^+$.

Step 4. Synthesis of (S)-6,6-difluoro-7-(3-fluorophenyl)-3-(tetrahydro-2H-pyran-4-yl)-5,6,7,8-tetrahydropyrido[2,3-d]pyrimidine-2,4(1H,3H)-dione (C-1). A mixture of crude C-C (800 mg) in CH$_3$CN (10 mL) in a sealed vial was stirred 120° C. for 20 min in a microwave reactor. Subsequently, the mixture was diluted with water (50 mL) and the resulting mixture was extracted with EtOAc (50 mL×3). The combined organic extracts were washed with brine and dried over anhydrous Na$_2$SO$_4$. The solvent was removed and the residue was purified by preparative HPLC (column: XBridge C18 OBD Prep Column, 19 mm×250 mm; mobile phase: water (0.05% (v/v) NH$_3$·H$_2$O)/CH$_3$CN=11.0% (v/v) to 30.0% (v/v) in 8 min; detector: UV 254 nm) to give C-1 (197 mg, 27% three steps from C-A) as a white solid. LC-MS (ES, m/z): 382 [M+H]+; $^1$H NMR (400 MHz, d$^6$-DMSO): δ 10.67 (s, 1H), 7.51-7.45 (m, 1H), 7.32-7.14 (m, 3H), 7.05 (s, 1H), 5.04-4.73 (m, 2H), 4.02-3.80 (m, 2H), 3.36-3.30 (m, 2H), 2.95-2.72 (m, 1H), 2.66-2.52 (m, 3H), 1.51-1.33 (m, 2H).

Example 1-1: Preparation of (6S,7S)-6-fluoro-7-(3-fluorophenyl)-3-(tetrahydro-2H-pyran-4-yl)-5,6,7,8-tetrahydropyrido[2,3-d]pyrimidine-2,4(1H, 3H)-dione (1)

Scheme 1

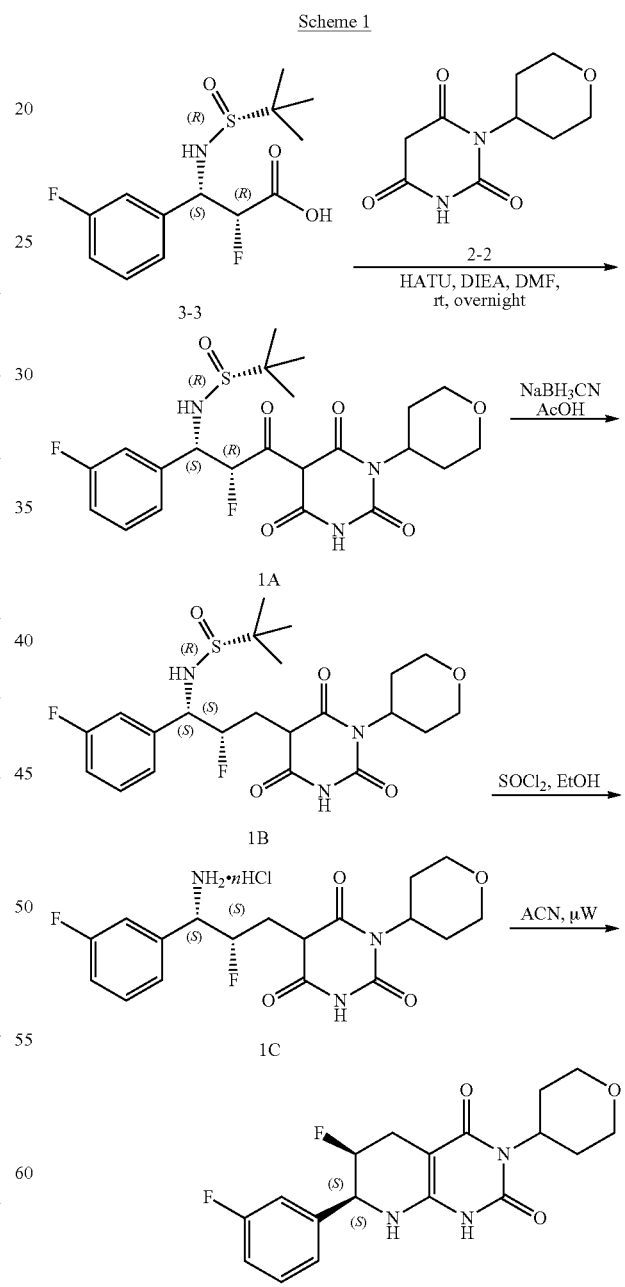

Steps 1 to 4. Synthesis of (6S,7S)-6-fluoro-7-(3-fluorophenyl)-3-(tetrahydro-2H-pyran-4-yl)-5,6,7,8-tetrahydropyrido[2,3-d]pyrimidine-2,4(1H, 3H)-dione (1). Following the same procedure as that described for preparing (S)-6,6-difluoro-7-(3-fluorophenyl)-3-(tetrahydro-2H-pyran-4-yl)-5, 6, 7, 8-tetrahydropyrido[2,3-d]pyrimidine-2,4(1H, 3H)-dione (C-4) and replacing (S)-3-(((S)-tert-butylsulfinyl)amino)-2,2-difluoro-3-(3-fluorophenyl)propanoic acid (1-4) with (2R,3S)-3-(((R)-tert-butylsulfinyl)amino)-2-fluoro-3-(3-fluorophenyl)propanoic acid (3-3), 1 was obtained as a white solid. LC-MS (ES, m/z): 364 [M+H]+; 1H NMR (300 MHz, d6-DMSO): δ 10.18 (s, 1H), 7.61-7.37 (m, 1H), 7.31-7.11 (m, 3H), 6.52 (s, 1H), 5.08 (m, 1H), 4.88 (m, 1H), 4.72 (d, J=26.8 Hz, 1H), 3.93 (m, 2H), 3.34 (m, 2H), 2.74-2.53 (m, 4H), 1.46-1.31 (m, 2H); 19F NMR (376 MHz, d6-DMSO): δ −113.18, −192.36.

Example 1-2: Preparation of (6R,7S)-6-fluoro-7-(3-fluorophenyl)-3-(tetrahydro-2H-pyran-4-yl)-5, 6, 7, 8-tetrahydropyrido[2,3-d]pyrimidine-2,4(1H, 3H)-dione (2)

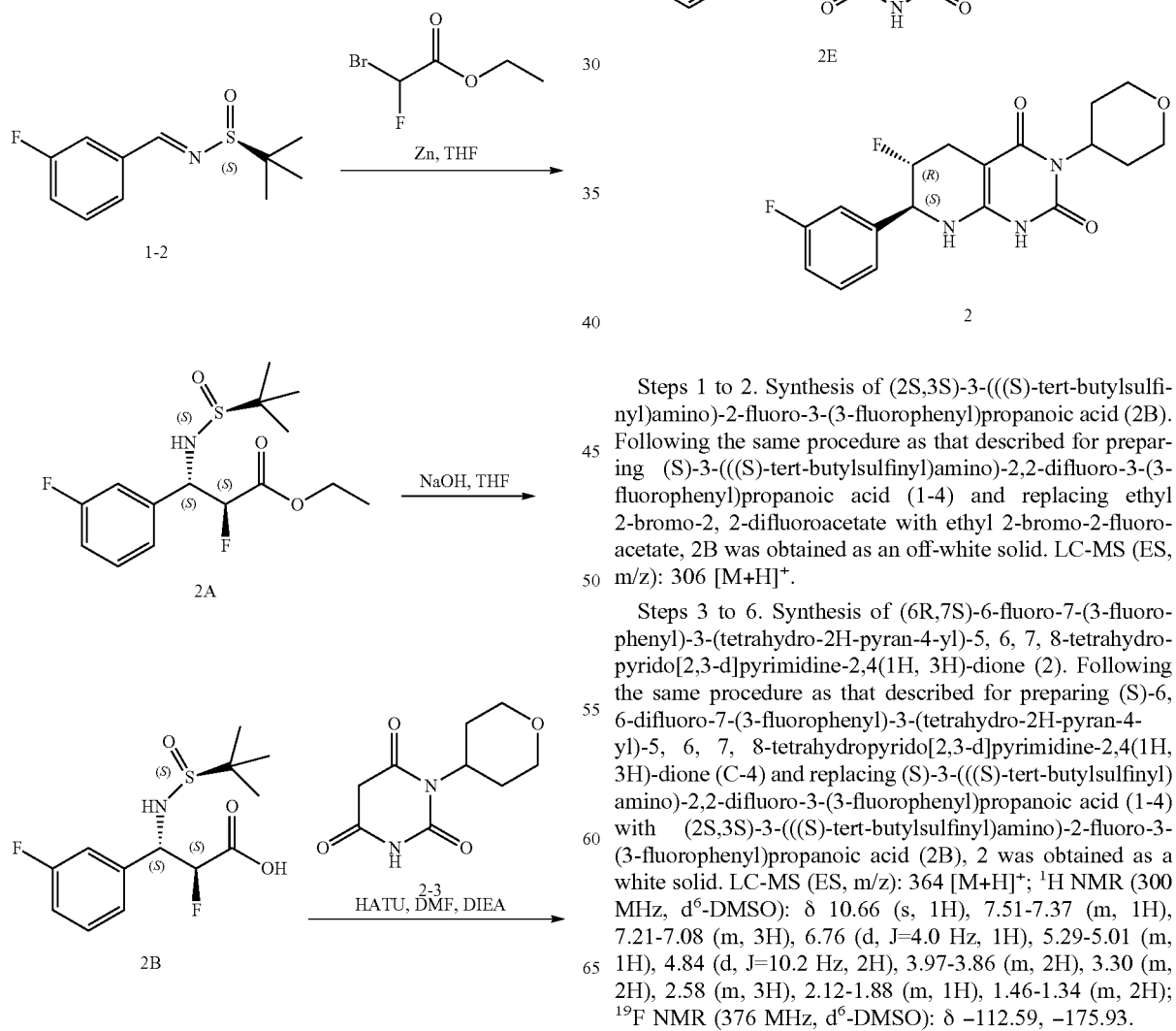

Steps 1 to 2. Synthesis of (2S,3S)-3-(((S)-tert-butylsulfinyl)amino)-2-fluoro-3-(3-fluorophenyl)propanoic acid (2B). Following the same procedure as that described for preparing (S)-3-(((S)-tert-butylsulfinyl)amino)-2,2-difluoro-3-(3-fluorophenyl)propanoic acid (1-4) and replacing ethyl 2-bromo-2, 2-difluoroacetate with ethyl 2-bromo-2-fluoroacetate, 2B was obtained as an off-white solid. LC-MS (ES, m/z): 306 [M+H]+.

Steps 3 to 6. Synthesis of (6R,7S)-6-fluoro-7-(3-fluorophenyl)-3-(tetrahydro-2H-pyran-4-yl)-5, 6, 7, 8-tetrahydropyrido[2,3-d]pyrimidine-2,4(1H, 3H)-dione (2). Following the same procedure as that described for preparing (S)-6,6-difluoro-7-(3-fluorophenyl)-3-(tetrahydro-2H-pyran-4-yl)-5, 6, 7, 8-tetrahydropyrido[2,3-d]pyrimidine-2,4(1H, 3H)-dione (C-4) and replacing (S)-3-(((S)-tert-butylsulfinyl)amino)-2,2-difluoro-3-(3-fluorophenyl)propanoic acid (1-4) with (2S,3S)-3-(((S)-tert-butylsulfinyl)amino)-2-fluoro-3-(3-fluorophenyl)propanoic acid (2B), 2 was obtained as a white solid. LC-MS (ES, m/z): 364 [M+H]+; 1H NMR (300 MHz, d6-DMSO): δ 10.66 (s, 1H), 7.51-7.37 (m, 1H), 7.21-7.08 (m, 3H), 6.76 (d, J=4.0 Hz, 1H), 5.29-5.01 (m, 1H), 4.84 (d, J=10.2 Hz, 2H), 3.97-3.86 (m, 2H), 3.30 (m, 2H), 2.58 (m, 3H), 2.12-1.88 (m, 1H), 1.46-1.34 (m, 2H); 19F NMR (376 MHz, d6-DMSO): δ −112.59, −175.93.

Example 1-3: Preparation of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2, 4 (1H, 3H)-dione (3)

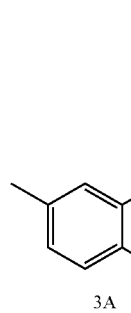

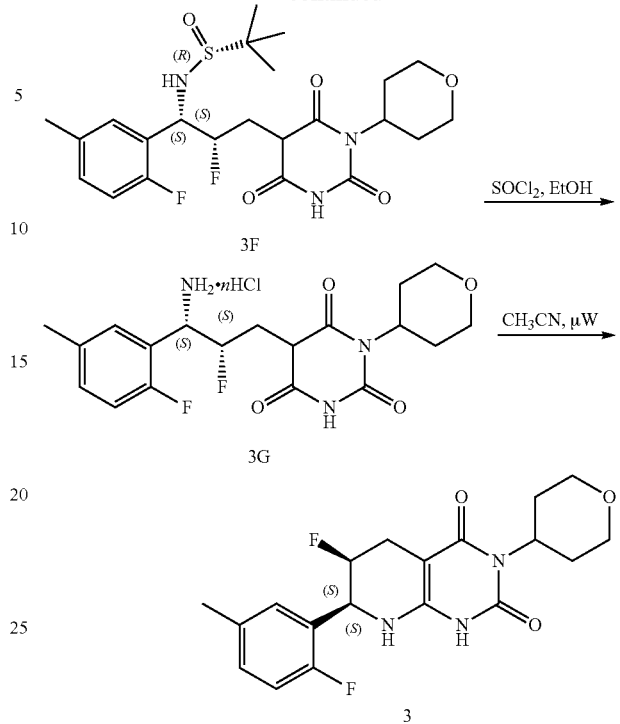

Step 1. Synthesis of (R,E)-N-(2-fluoro-5-methylbenzylidene)-2-methylpropane-2-sulfinamide (3B). A mixture of 2-fluoro-5-methylbenzaldehyde (3A) (5 g, 36.2 mmol), Cs$_2$CO$_3$ (17.6 g, 54.0 mmol), and (R)-2-methylpropane-2-sulfinamide (4.6 g, 38.0 mmol) in DCM (100 mL) was stirred at rt overnight under an atmosphere of Ar. The reaction mixture was filtered and the filtrate was diluted with ether (150 mL). Subsequently, the resulting suspension was filtered. The filtrate was concentrated and the residue was dried in vacuo to give 3B (8.7 g, 97%) as a yellow oil. LC-MS (ES, m/z): 242 [M+H]$^+$; $^1$H NMR (400 MHz, d$^6$-DMSO): δ 8.87 (s, 1H), 7.76 (m, 1H), 7.29 (m, 1H), 7.03 (m, 1H), 2.37 (d, J=1.0 Hz, 3H), 1.27 (s, 9H).

Step 2. Synthesis of ethyl (2R,3S)-3-(((R)-tert-butylsulfinyl)amino)-2-fluoro-3-(2-fluoro-5-methylphenyl)propanoate (3C). To a solution of 3B (4 g, 16.6 mmol), ethyl 2-fluoroacetate (2.6 g, 24.6 mmol), and TMEDA (4.8 mL) in anhydrous THF (40 mL) was added LiHMDS (1 M in THF, 24.6 mL, 24.6 mmol) dropwise at −78° C. over 30 min under an atmosphere of Ar. After stirring at −78° C. for 1 h, the reaction was quenched by adding 1 N aq. HCl (50 mL), while maintaining the inner temperature of the mixture at <−20° C. Subsequently, the mixture was concentrated to remove most of the organic solvent and then extracted with EtOAc (100 mL×3). The combined organic extracts were washed with brine (100 mL) and dried over anhydrous Na$_2$SO$_4$. The solvent was removed and the residue was dried in vacuo to give crude 3C (6.0 g) as a yellow oil, which was used for the next step without further purification. LC-MS (ES, m/z): 348 [M+H]$^+$.

Step 3. Synthesis of (2R,3S)-3-(((R)-tert-butylsulfinyl)amino)-2-fluoro-3-(2-fluoro-5-methylphenyl)propanoic acid (3D). To a solution of 3C (6.0 g, 17.3 mmol) in THF (40 mL) was added 1N aq. NaOH (34.6 mL, 34.6 mmol) at rt. After stirring at rt for 1 h, the reaction mixture was added ice water (50 mL). The resulting mixture was extracted with EtOAc (100 mL×2). The aqueous layer was adjusted to pH 5 with sat. aq. citric acid, followed by extraction with EtOAc (100 mL×3). Subsequently, the combined organic extracts were washed with brine (100 mL) and dried over anhydrous Na₂SO₄. The solvent was removed and the residue was purified by preparative HPLC (Column: XBridge Prep OBD C18 Column, 19×250 mm, 5um; mobile phase: water (0.05% TFA) and ACN (28.0% ACN up to 36.0% in 10 min); detector: UV 220 nm) to give 3D (2 g, 36%) as a white solid. LC-MS (ES, m/z): 320 [M+H]⁺; ¹H NMR (400 MHz, d⁶-DMSO): δ 13.57 (br, 1H), 7.55 (dd, J=7.5, 2.2 Hz, 1H), 7.23-6.94 (m, 2H), 6.04 (d, J=10.8 Hz, 1H), 5.37-4.86 (m, 2H), 2.29 (s, 3H), 1.12 (s, 9H).

Step 4. Synthesis of (R)—N-S,2R)-2-fluoro-1-(2-fluoro-5-methylphenyl)-3-oxo-3-(2,4,6-trioxo-1-(tetrahydro-2H-pyran-4-yl)hexahydropyrimidin-5-yl)propyl)-2-methylpropane-2-sulfinamide (3E). A solution of 3D (700 mg, 2.19 mmol), 2-2 (698 mg, 3.29 mmol), and HATU (1.25 g, 3.29 mmol) in DMF (10 mL) was added DIEA (849 mg, 6.57 mmol) at 0° C. under an atmosphere of Ar. After stirring at rt for 2 h, the reaction was quenched by adding sat. aq. sodium bicarbonate (30 mL) and the resulting solution was extracted with ethyl acetate (50 mL×3). The combined organic extracts were washed with brine (50 mL×2) and dried over anhydrous Na₂SO₄. The solvent was removed and the residue was dried in vacuo to give crude 3E (1.3 g) as a white solid, which was used for the next step without further purification. LC-MS (ES, m/z): 514 [M+H]⁺; ¹H NMR (400 MHz, d⁶-DMSO): δ 12.16 (br, 1H), 7.66-7.45 (m, 1H), 7.23-6.98 (m, 2H), 6.37 (m, 1H), 6.13 (d, J=10.7 Hz, 1H), 5.22 (m, 1H), 4.79 (m, 1H), 3.94 (m, 2H), 3.35 (t, J=11.7 Hz, 2H), 2.52-2.39 (m, 2H), 2.29 (s, 3H), 1.49 (d, J=12.2 Hz, 2H), 1.04 (s, 9H).

Step 5. Synthesis of (R)—N-((1S,2S)-2-fluoro-1-(2-fluoro-5-methylphenyl)-3-(2,4,6-trioxo-1-(tetrahydro-2H-pyran-4-yl)hexahydropyrimidin-5-yl)propyl)-2-methylpropane-2-sulfinamide (3F). A solution of crude 3E (1.3 g, 2.53 mmol) in AcOH (10 mL) was added NaBH3CN (398 mg, 6.33 mmol) at 0° C. under an atmosphere of Ar. After stirring at rt for 1 h, the reaction mixture was added ice water (20 mL) and the resulting solution was extracted with EtOAc (50 mL×3). Next, the combined organic extracts were washed with brine (50 mL) and dried over anhydrous Na₂SO₄. The solvent was removed and the residue was dried in vacuo to give crude 3F (1.3 g) as a white solid, which was used for the next step without further purification. LC-MS (ES, m/z): 500 [M+H]⁺; ¹H NMR (400 MHz, d⁶-DMSO): δ 11.31 (d, J=28.1 Hz, 1H), 7.41 (d, J=7.4 Hz, 1H), 7.27-6.84 (m, 2H), 6.11-5.78 (m, 2H), 5.08-4.43 (m, 3H), 3.87 (m, 3H), 2.29 (s, 6H), 1.99 (s, 1H), 1.53-1.28 (m, 2H), 1.10 (d, J=2.1 Hz, 10H).

Step 6. Synthesis of 5-02S,3S)-3-amino-2-fluoro-3-(2-fluoro-5-methylphenyl)propyl)-1-(tetrahydro-2H-pyran-4-yl)pyrimidine-2, 4, 6 (1H, 3H, 5H)-trione (3G). A solution of crude 3F (1.3 g, 2.60 mmol) in ethanol (10 mL) was added thionyl chloride (334 mg) at 0° C. After stirring at rt for 1 h, the reaction mixture was concentrated and the residue was dried in vacuo to give crude 3G (1.0 g) as a white solid, which was used for the next step without further purification. LC-MS (ES, m/z): 396 [M+H]⁺.

Step 7. Synthesis of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2, 4 (1H, 3H)-dione (3). A mixture of crude 3G (1.0 g, 2.53 mmol) in CH₃CN (15 mL) was put into a microwave reactor with stirring at 120° C. for 30 min. Subsequently, the mixture was concentrated and the residue was purified by preparative HPLC (column: C18 silica gel; mobile phase: CH₃CN:H2O=20:80 (v/v) increasing to CH3CN:H2O=80:20 (v/v) within 40 min; detector: UV 254 nm) to give compound 3 (302 mg, 32%), as a white solid, which was identified as Form 1 polymorph (see Example 2). LC-MS (ES, m/z): 378 [M+H]⁺; ¹H NMR (300 MHz, d⁶-DMSO): δ 10.20 (s, 1H), 7.38-7.05 (m, 3H), 6.45 (s, 1H), 5.11-4.81 (m, 3H), 3.89 (dd, J=10.8, 3.9 Hz, 2H), 3.34-3.27 (m, 3H), 2.76-2.48 (m, 4H), 2.28 (s, 3H), 1.39-1.36 (m, 2H); ¹⁹F NMR (376 MHz, d⁶-DMSO): δ -123.51 (t, J=86.5 Hz), -191.57 (d, J=129.34 Hz).

Example 1-4: Preparation of (6R,7S)-6-fluoro-7-(2-fluoro-5-methylphenyl)-3-(tetrahydro-2H-pyran-4-yl)-5,6,7,8-tetrahydropyrido[2,3-d]pyrimidine-2,4 (1H, 3H)-dione (4)

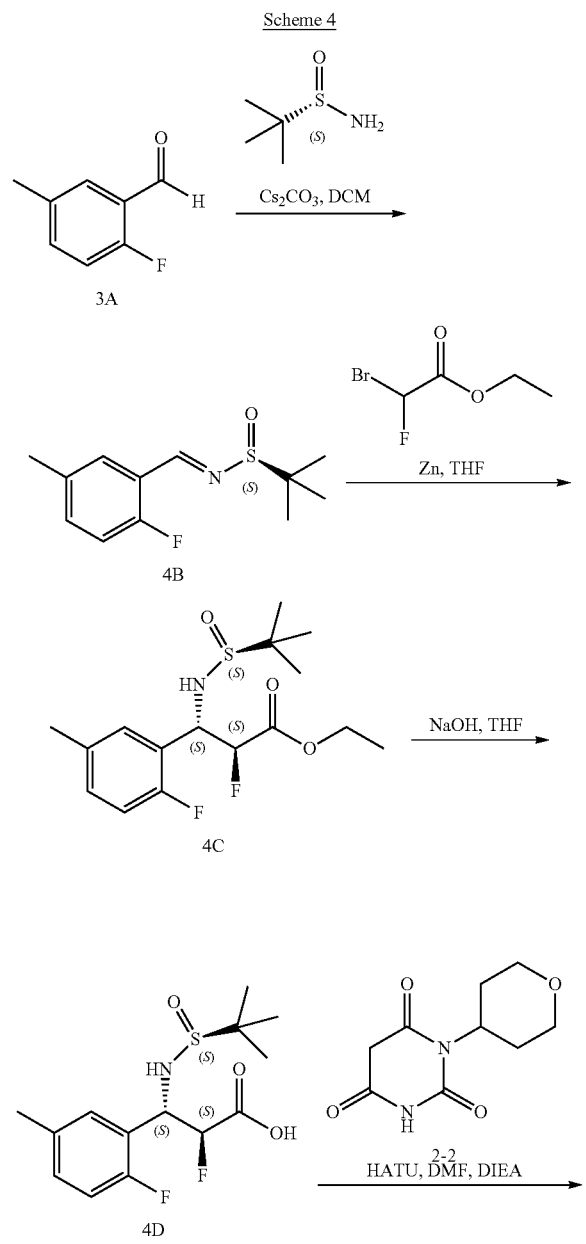

Scheme 4

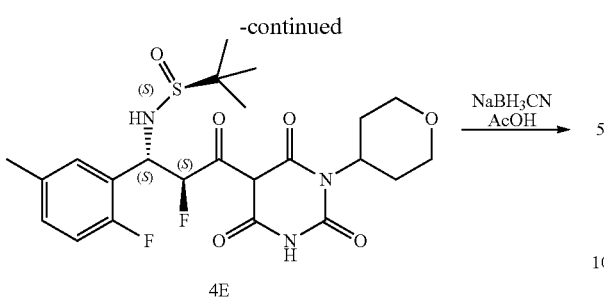

4E

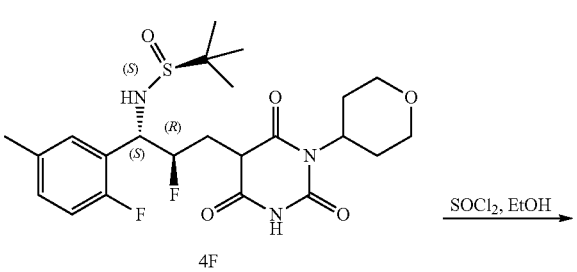

4F

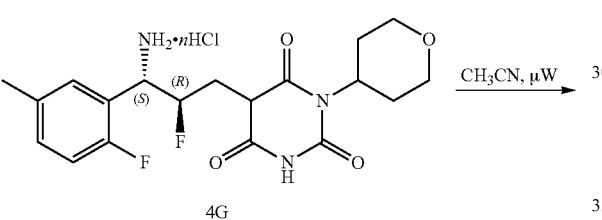

4G

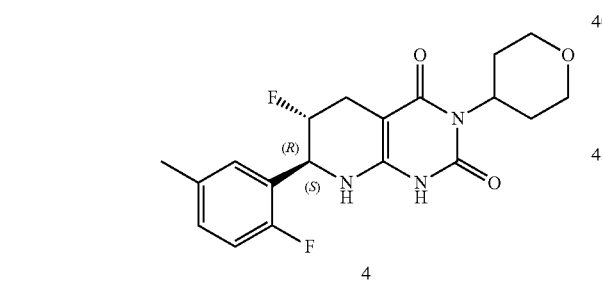

4

Steps 1 to 7. Synthesis of (6R,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H, 3H)-dione (4). Following the same procedure as that described for preparing (6R,7S)-6-fluoro-7-(3-fluorophenyl)-3-(tetrahydro-2H-pyran-4-yl)-5, 6, 7, 8-tetrahydropyrido[2,3-d]pyrimidine-2, 4(1H, 3H)-dione (2) and replacing 3-fluorobenzaldehyde (1-1) with 2-fluoro-5-methylbenzaldehyde (3A), 4 was obtained as a white solid. LC-MS (ES, m/z): 378 [M+H]+; 1H NMR (400 MHz, d6-DMSO): δ 10.69 (s, 1H), 7.19-7.09 (m, 2H), 6.98 (d, J=6.8 Hz, 1H), 6.62 (d, J=3.6 Hz, 1H), 5.08-4.84 (m, 3H), 3.91 (dd, J=11.2, 3.6 Hz, 2H), 3.32 (m, 2H), 2.68-2.55 (m, 4H), 2.27 (s, 3H), 2.17-2.03 (m, 1H), 1.42-1.39 (m, 2H); 19F NMR (376 MHz, d6-DMSO): δ −124.08, −175.61.

Example 1-5: Preparation of Synthesis of (6R,7R)-6-fluoro-7-(2-fluoro-5-methylphenyl)-3-(tetrahydro-2H-pyran-4-yl)-5,6,7,8-tetrahydropyrido[2,3-d]pyrimidine-2,4(1H, 3H)-dione (5)

Scheme 5

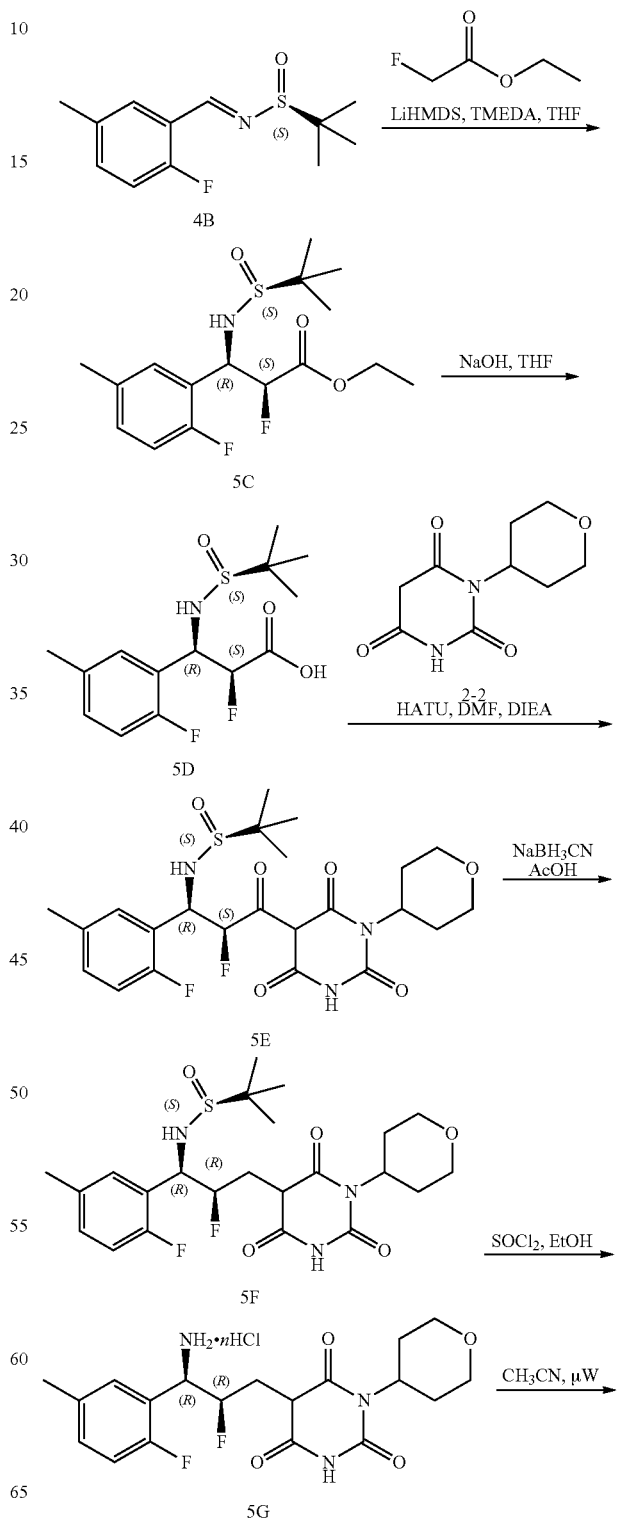

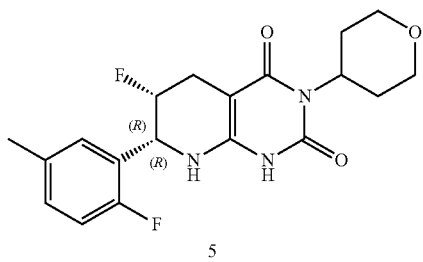

5

Steps 1 to 6. Synthesis of (6R,7R)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione (5). Following the same procedure as that described for preparing (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione (3) and replacing (R,E)-N-(2-fluoro-5-methylbenzylidene)-2-methylpropane-2-sulfinamide (3B) with (S,E)-N-(2-fluoro-5-methylbenzylidene)-2-methylpropane-2-sulfinamide (4B), 5 was obtained as a white solid. LC-MS (ES, m/z): 378 [M+H]$^+$; $^1$H NMR (300 MHz, d$^6$-DMSO): δ 10.72 (s, 1H), 7.85-7.11 (m, 3H), 6.45 (s, 1H), 5.14-3.93 (m, 3H), 3.92 (dd, J=10.4, 5.2 Hz, 2H), 3.52-3.29 (m, 3H), 2.82-2.66 (m, 4H), 2.31 (s, 3H), 1.39-1.36 (m, 2H); 19F NMR (376 MHz, d$^6$-DMSO): δ −123.49, −191.34.

Example 1-6: Preparation of (6S,7R)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione (6)

Scheme 6

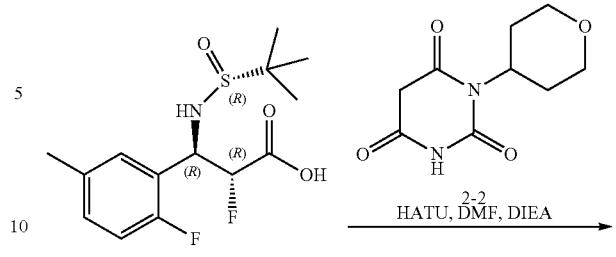

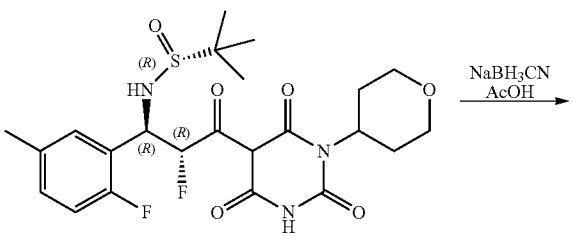

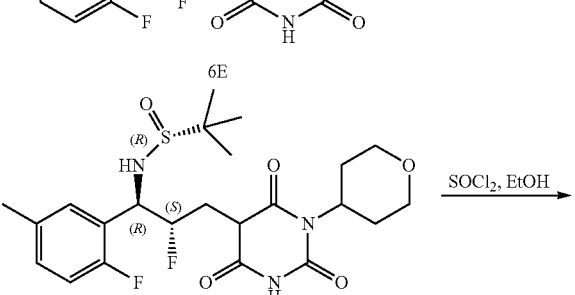

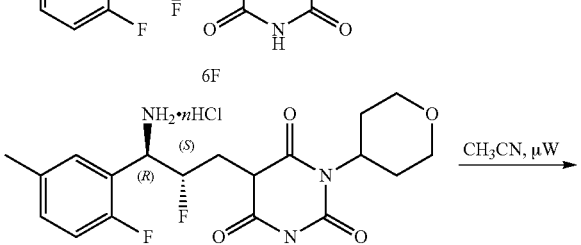

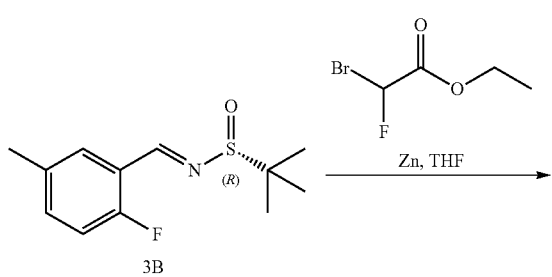

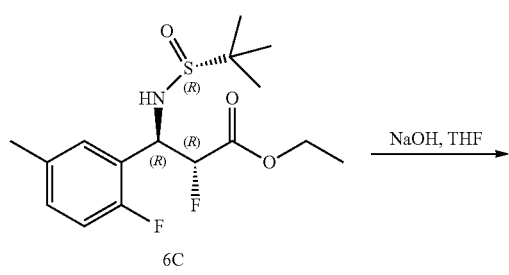

Steps 1 to 6. (6S,7R)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione (6). Following the same procedure as that described for preparing (6R,7S)-6-fluoro-7-(3-fluorophenyl)-3-(tetrahydro-2H-pyran-4-yl)-5,6,7,8-tetrahydropyrido[2,3-d]pyrimidine-2,4(1H,3H)-dione (2) and replacing (S,E)-N-(3-fluorobenzylidene)-2-methylpropane-2-sulfinamide (1-2) with (R,E)-N-(2-fluoro-5-methylbenzylidene)-2-methylpropane-2-sulfinamide (3B), 6 was obtained as a white solid. LC-MS (ES, m/z): 378 [M+H]+; $^1$H NMR (300 MHz, D$^6$-DMSO): δ 10.69 (s, 1H), 7.21-7.09 (m, 2H), 6.98 (d, J=6.8 Hz, 1H), 6.66 (d, J=3.6 Hz, 1H), 5.11-4.84 (m, 3H), 3.92 (dd, J=11.1, 3.9 Hz, 2H), 3.35-3.29 (m, 2H), 2.69-2.52 (m, 4H), 2.27 (s, 3H), 2.14-2.00 (m, 1H), 1.43-1.39 (m, 2H); 19F NMR (376 MHz, D$^6$-DMSO): δ −124.36, −175.43.

Additional compounds were prepared using similar approaches to those provided above.

Characterization Data for Compounds

TABLE 1A

| STRUCTURE | Observed MS [M + H]+ | Proton NMR | Synthetic method(s) | bcMF pCa_6 IC50 MEAN |
|---|---|---|---|---|
| 7 | 388 | ¹H NMR (400 MHz, d⁶-DMSO in ppm): δ 7.68-7.51 (m, 2H), 7.33-7.29 (m, 1H), 5.14 -4.83 (m, 3H), 4.20 (s, 1H), 3.91-3.88 (m, 2H), 3.39-3.28 (m, 2H), 2.77-2.58 (m, 4H), 1.39-1.31 (m, 2H) | Scheme 3 | 0.54 |
| 8 | 364 | ¹H NMR (400 MHz, d⁶-DMSO in ppm): δ 10.73 (s, 1H), 7.43-7.36 (m, 1H), 7.27-7.18 (m, 3H), 6.65 (d, J = 4.0 Hz, 1H), 5.13-4.97 (m, 2H), 4.86 (tt, J = 12.1 and 4.2 Hz, 1H), 3.91 (dd, J = 11.4 and 4.5 Hz, 2 H), 3.36-3.29 (m, 2H), 2.69-2.55 (m, 3H), 2.05 (ddd, J = 40.8, 17.0 and 3.3 Hz, 1H), 1.45-1.37 (m, 2H) | Scheme 2 | 1.46 |
| 9 | 364 | ¹H NMR (400 MHz, d⁶-DMSO in ppm): δ 10.24 (s, 1H), 7.45-7.38 (m, 1H), 7.30-7.21 (m, 3H), 6.44 (s, 1H), 5.08 (dm, J = 47.4 Hz, 1H), 4.98 (d, J = 25.0 Hz, 1H), 4.87 (tt, J = 12.1 and 4.2 Hz, 1H), 3.92 (dd, J = 11.2 and 4.4 Hz, 2H), 3.37-3.29 (m, 2H), 2.78-2.52 (m, 4H), 1.44-1.36 (m, 2H) | Scheme 1 | 5.59 |
| 10 | 394 | ¹H NMR (400 MHz, d⁶-DMSO in ppm): δ 10.26 (s, 1H), 7.20 (dd, J = 10.1 and 9.0 Hz, 1H), 6.97 (ddd, J = 9.0, 4.0 and 2.5 Hz, 1H), 6.91 (dd, J = 6.1 and 2.5 Hz, 1H), 6.47 (s, 1H), 5.14-4.81 (m, 3H), 3.91 (dd, J = 11.4 and 4.6 Hz, 2H), 3.74 (s, 3H), 3.36-3.28 (m, 2H), 2.75-2.53 (m, 4H), 1.43-1.35 (m, 2H) | Scheme 3 | 1.02 |
| 11 | 394 | ¹H NMR (400 MHz, d⁶-DMSO in ppm): δ 10.75 (s, 1H), 7.19 (dd, J = 10.0 and 9.1 Hz, 1H), 6.94 (dt, J = 9.1 and 3.5 Hz, 1H), 6.72 (s, 1H), 6.65 (dd, J = 6.1 and 3.5 Hz, 1H), 5.12-4.94 (m, 2H), 4.86 (tt, J = 12.1 and 4.0 Hz, 1H), 3.90 (dd, J = 11.4 and 4.2 Hz, 2H), 3.71 (s, 3H), 3.37-3.28 (m, 2H), 2.69-2.53 (m, 3H), 2.09 (ddd, J = 39.6, 16.8 and 3.4 Hz, 1H), 1.44-1.37 (m, 2H) | Scheme 4 | 0.49 |

TABLE 1A-continued

| STRUCTURE | Observed MS [M + H]+ | Proton NMR | Synthetic method(s) | bcMF pCa_6 IC50 MEAN |
|---|---|---|---|---|
| 6 | 378 | ¹H NMR (300 MHz, d⁶-DMSO in ppm): δ 10.69 (s, 1H), 7.21-7.09 (m, 2H), 6.98 (d, J = 6.8 Hz, 1H), 6.66 (d, J = 3.6 Hz, 1H), 5.11-4.84 (m, 3H), 3.92 (dd, J = 11.1, 3.9 Hz, 2H), 3.35-3.29 (m, 2H), 2.69-2.52 (m, 4H), 2.27 (s, 3H), 2.14-2.00 (m, 1H), 1.43-1.39 (m, 2H) | Scheme 6 | 26.4 |
| 5 | 378 | ¹H NMR (300 MHz, d⁶-DMSO in ppm): δ 10.72 (s, 1H), 7.85-7.11 (m, 3H), 6.45 (s, 1H), 5.14-3.93 (m, 3H), 3.92 (dd, J = 10.4, 5.2 Hz, 2H), 3.52-3.29 (m, 3H), 2.82-2.66 (m, 4H), 2.31 (s, 3H), 1.39-1.36 (m, 2H) | Scheme 5 | 20.84 |
| 4 | 378 | ¹H NMR (400 MHz, d⁶-DMSO in ppm): δ 10.69 (s, 1H), 7.19-7.09 (m, 2H), 6.98 (d, J = 6.8 Hz, 1H), 6.62 (d, J = 3.6 Hz, 1H), 5.08-4.84 (m, 3H), 3.91 (dd, J = 11.2, 3.6 Hz, 2H), 3.32 (m, 2H), 2.68-2.55 (m, 4H), 2.27 (s, 3H), 2.17-2.03 (m, 1H), 1.42-1.39 (m, 2H) | Scheme 4 | 0.37 |
| 3 | 378 | ¹H NMR (300 MHz, d⁶-DMSO in ppm): δ 10.20 (s, 1H), 7.38-7.05 (m, 3H), 6.45 (s, 1H), 5.11-4.81 (m, 3H), 3.89 (dd, J = 10.8, 3.9 Hz, 2H), 3.34-3.27 (m, 3H), 2.76-2.48 (m, 4H), 2.28 (s, 3H), 1.39-1.36 (m, 2H) | Scheme 3 | 1.11 |
| 1 | 364 | ¹H NMR (300 MHz, d⁶-DMSO in ppm): δ 10.18 (s, 1H), 7.61-7.37 (m, 1H), 7.31-7.11 (m, 3H), 6.52 (s, 1H), 5.08 (m, 1H), 4.88 (m, 1H), 4.72 (d, J = 26.8 Hz, 1H), 3.93 (m, 2H), 3.34 (m, 2H), 2.74-2.53 (m, 4H), 1.46-1.31 (m, 2H) | Scheme 1 | 3.0325 |

TABLE 1A-continued

| STRUCTURE | Observed MS [M + H]+ | Proton NMR | Synthetic method(s) | bcMF pCa_6 IC50 MEAN |
|---|---|---|---|---|
| 12 | 364 | $^1$H NMR (300 MHz, d$^6$-DMSO in ppm): δ 10.13 (s, 1H), 7.57-7.37 (m, 1H), 7.18 (m, 3H), 6.47 (s, 1H), 5.03 (d, J = 47.8 Hz, 1H), 4.90-4.76 (m, 1H), 4.67 (d, J = 26.6 Hz, 1H), 3.88 (m, 2H), 3.33 (m, 1H), 3.25 (m, 1H), 2.76-2.48 (m, 4H), 1.37 (m, 2H) | Scheme 5 | 23.17 |
| 2 | 364 | $^1$H NMR (300 MHz, d$^6$-DMSO in ppm): δ 10.66 (s, 1H), 7.51-7.37 (m, 1H), 7.21-7.08 (m, 3H), 6.76 (d, J = 4.0 Hz, 1H), 5.29-5.01 (m, 1H), 4.84 (d, J = 10.2 Hz, 2H), 3.97-3.86 (m, 2H), 3.30 (m, 2H), 2.58 (m, 3H), 2.12-1.88 (m, 1H), 1.46-1.34 (m, 2H) | Scheme 2 | 2.134 |
| 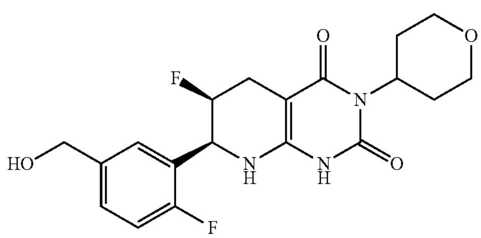 [SMILES: O=c1[nH]c2c(c(=O)n1C1CCOCC1)C[C@H](F)[C@H](c1cc(CO)ccc1F)N2] | 394 | $^1$H NMR (400 MHz, DMSO-d$^6$): δ 10.24 (s, 1H), 7.40 (d, J = 7.1 Hz, 1H), 7.33 (s, 1H), 7.25-7.16 (m, 1H), 6.45 (s, 1H), 5.30 (t, J = 5.6 Hz, 1H), 5.16-4.86 (m, 3H), 4.49 (d, J = 5.1 Hz, 2H), 3.92 (dd, J = 11.4, 4.4 Hz, 2H), 3.36 (s, 2H), 2.63 (s, 4H), 1.40 (d, J = 12.2 Hz, 2H) | Scheme 3 | 0.78 |

Example 2

Single Crystal X-Ray Analysis—Form 1

SXRD analysis was conducted on an Agilent Technologies (Dual Source) SuperNova diffractometer using monochromated Cu Kα (λ. 1.54178 Å) radiation generated by sealed tube. The diffractometer was fitted with an Oxford Cryosystems low temperature device to enable data collection to be performed at 120(1) K and the crystal encased in a protective layer of Paratone oil. The data collected were corrected for absorption effects based on Gaussian integration over a multifaceted crystal model, implemented as a part of the CrysAlisPro software package (Agilent Technologies, 2014).

Figure 4:
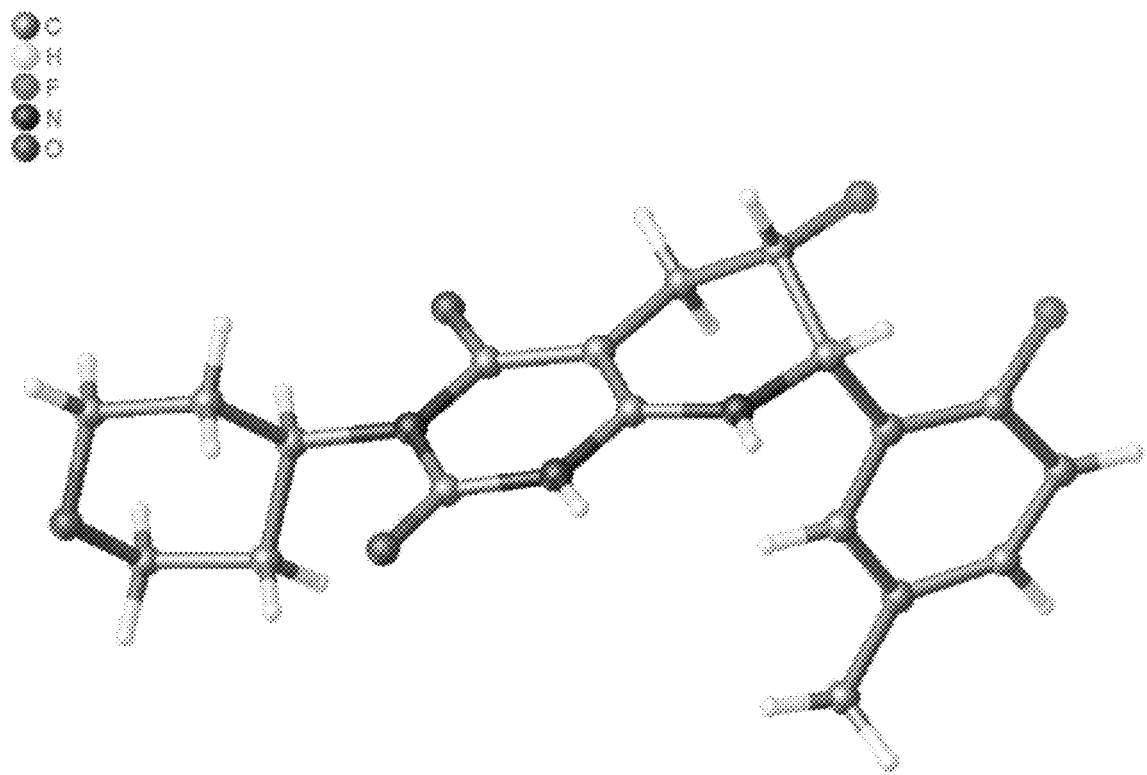
FIG. 4 shows crystal structure of Form 1 polymorph of the compound of Example 1-3 (also referred to as compound 3) obtained by single crystal X-ray diffraction.

The structure was solved by direct methods (SHELXS97)[1] and developed by full least squares refinement on F$^2$ (SHELXL97)[1] interfaced via the OLEX2 software package (see FIG. 4). Images produced were done so via OLEX2.[2] Data was collected, solved and refined in the orthorhombic space-group P2$_1$2$_1$2$_1$ and a search for higher metric symmetry using the ADDSYMM[3] routine of PLATON[4] but failed to uncover any higher order symmetry. All non-hydrogen atoms were located in the Fourier map and their positions refined prior to describing their thermal movement of all non-hydrogen atoms anisotropically. Within the structure, one, complete molecule of 3 (also referred to as a compound of Example 3) was located in the asymmetric unit only. Due to the weak diffraction data obtained, the Flack parameter could be calculated to −0.0657 with esd of 0.7497 (calculated from 1477 Bijovet pairs with 97.6% completeness). Attempts to refine the structure using TWIN and BASF commands did not yield further improvements. All hydrogen atoms were placed in calculated positions using a riding model with fixed Uiso at 1.2 times for all CH, CH$_2$ and NH groups, and 1.5 times for all CH$_3$ groups. The highest residual Fourier peak was found to be 1.34 e·Å$^{-3}$ approx 0.68 Å from C(16) and the deepest Fourier hole was found to be −0.89 e·Å$^{-3}$ approx 0.58 Å from O(2).

Crystal Data—Form 1

$C_{19}H_{21}F_2N_3O_3$ (M=377.39 g/mol): orthorhombic, space group P2$_1$2$_1$2$_1$ (no. 19), a=28.153(2) Å, b=6.6890(3) Å, c=9.1390(6) A, V=1721.04(19) Å$^3$, Z=4, T=120(1) K, μ(CuKα)=0.964 mm$^{-1}$, Dcalc=1.456 g/cm$^3$, 30202 reflections measured (10.18°≤2Θ≤) 153.36°, 3570 unique ($R_{int}$=0.1117, $R_{sigma}$=0.0636) which were used in all calculations. The final R1 was 0.1591 (>2sigma(I)) and wR$_2$ was 0.3889 (all data).

X-ray Powder Diffraction (XRPD), Dynamic Scanning calorimetry (DSC) and Thermo Gravimeric Analysis (TGA) data for Form 1 of the compound of Example 1-3 are shown in FIGS. 1A-1C, 2 and 3, respectively.

BIOLOGICAL EXAMPLES

Compounds were profiled by assessing their physicochemical properties, biochemical activities, cell-based activities, selectivity profiles, pharmacokinetic (PK) profiles, pharmacodynamic (PD) profiles, and safety profiles in various in vitro and in vivo assays, including but not limited to myosin ATPase assays (bovine cardiac myobril system (bcMF) with/without serum and rabbit skeletal myobril system (rbskMF), cardiomyocyte contractility and reactive metabolite identification.

Compounds with a reduced half-life were selected to enable a potentially more rapid dose adjustment, since a shorter half-life allows a faster time to get to steady-state exposures. Removal, or minimization, of dependence on polymorphic cytochrome P450 (CYP) enzymes, such as CYP2C19, for the metabolic clearance of the drug candidates provided a potential advantage for reduced human PK variability that may occur for instance between poor and rapid drug metabolizers. Removal, or minimization, of potent CYP enzyme induction properties of a new drug candidates provided an advantage to avoid potential for drug-drug interactions. Increased selectivity of the drug candidate for cardiac myosin over skeletal myosin had a benefit for desired human pharmacokinetics related to myosin modulator drug distribution. Myosin modulator candidate drugs with decreased potency toward skeletal myosin were predicted to distribute less into skeletal muscle tissue, due to lower drug binding to skeletal myosin, leading to decreased volume of distribution and therefore decreased half-life in human Preclinical pharmacokinetic/pharmacodynamics studies were performed to optimize the selection compounds with that may allow oral dosing with reduced risk of drug-induced liver toxicity. Lammert et al. (2008) Relationship Between Daily Dose of Oral Medications and Idiosyncratic Drug-induced Liver Injury: Search for Signals. Hepatology, 47: 2003-2009.

KS Solubility Assay

Small molecule agents were assessed for their kinetic solubility in PBS at pH7.4 at rt using Reserpine (kinetic solubility <15 µM in PBS at 7.4) as a negative control and Verapamil (kinetic solubility >200 µM in PBS at 7.4) as a positive control. 2 µL of the 20 mM DMSO stock solution of a compound was added into a well in a 96-well plate, followed by adding 198 µL of PBS at rt. After shaking at room temperature for 1.5 h, the mixture was filtered under vacuum through a 96-well filter plate, which was pre-washed with 100 µL of 70% ethanol per well. Subsequently, 70 µL of the filtrate was added into a well in a 96-well reading plate, which was pre-loaded with 70 µL of DMSO per well. The concentration of the sample in a well was determined on the basis of the intergration on LC with UV detection as compared to the standard curve of each compound established in DMSO.

Myosin Inhibition Assay (bcMF pCa 6 $IC_{50}$ (µM))

Small molecule agents were assessed for their ability to inhibit the enzymatic activity of bovine cardiac myosin using a biochemical assay that couples the release of ADP (adenosine diphosphate) from cardiac myosin to an enzymatic coupling system consisting of pyruvate kinase and lactate dehydrogenase (PK/LDH) and monitoring the absorbance decrease of NADH (at 340 nm) as a function of time. PK converts ADP to ATP (adenosine triphosphate) by converting PEP (phosphoenolpyruvate) to pyruvate. Pyruvate is then converted to lactate by LDH by converting NADH (nicotinamide adenine dinucleotide) to NAD (oxidized nicotinamide adenine dinucleotide). The source of cardiac myosin was from bovine heart in the form of skinned myofibrils. Prior to testing small molecule agents, the bovine myofibrils were assessed for their calcium responsiveness and the calcium concentration that achieves a 50% activation of the myofibril system was chosen as the final condition for assessing the inhibitory activity of the small molecule agents. All enzymatic activity was measured in a buffered solution containing 12 mM PIPES (piperazine-N,N'-bis(2-ethanesulfonic acid), 2 mM magnesium chloride at pH 6.8 (PM12 buffer). Final assay conditions were 1 mg/mL of bovine cardiac myofibrils, 0.4 mM PK/LDH, 50 uM ATP, 0.1 mg/mL BSA (bovine serum albumin), 10 ppm antifoam, 2 mM BME, 0.5 mM NADH, and 1.5 mM PEP at the desired free calcium concentration required to achieve 50% activation of the myofibrils.

A dilution series of compound was created in DMSO such that the final desired concentration of compound would be achieved in a volume of 30 µL with a fixed DMSO concentration of 3.3% (v/v). Typically 1 µL of the dilution series were added to 384 well plate to achieve a 10 point dose response. Following the addition of 14 µL of a solution containing bovine cardiac myofibrils, PK/LDH and a solution of calcium (that achieved 50% activation), the enzymatic reaction was started with the addition of 15 µL of a solution containing ATP, PEP and NADH. The reaction progress was followed in a PerkinElmer Envision plate reader at ambient temperature using clear bottom plates. The plate reader was configured to read absorbance at 340 nm in kinetics mode for 15 minutes. Data were recorded as the slope of the absorbance response to time. The slopes of the absorbance response as a function of time were normalized to slopes on the plate containing DMSO. This normalized rate was then plotted as a function of small molecule concentration and the data was fitted to a four-parameter fit using EXCEL XLfit. The $IC_{50}$ is the concentration at which fifty percent of the total response is inhibited. Any agent that failed to achieve a fifty percent inhibition at the highest concentration tested was reported as an $IC_{50}$ greater than the highest concentration tested (ie. $IC_{50}$>50 µM).

Myosin Inhibition Assay (bcMF Serum pCa 6 $IC_{50}$ (µM))

Inhibition of the enzymatic activity of bovine cardiac myosin associated with the release of ADP (adenosine diphosphate) at the calcium concentrate that achieves a 50% activation of the bovine cardiac myofibril system in the presence of 10% human serum. The procedure was the same as that bovin cardiac myosin inhibition assay (bcMF pCa 6 $IC_{50}$ (µM)) but with the addition of 10% human serum.

Myosin Inhibition Assay (rbskMF pCa 6 $IC_{50}$ (µM))

Inhibition of the enzymatic activity of rabbit skeletal myosin associated with the release of ADP (adenosine diphosphate) at the calcium concentrate that achieves a 50% activation of the rabbit skeletal myofibril system. The procedure was the same as that of bovin cardiac myosin inhibition assay (bcMF pCa 6 $IC_{50}$ (µM)) by replacing bovine cardiac myofibril with rabbit skeletal myofibril.

Pharmacokinetic/Pharmacodynamics (PK/PD) Relationship

The ability of small molecules to dose-dependently modulate systolic cardiac performance was assessed non-invasively using echocardiography in isoflurane-anesthetized SD rats. First, cardiac function/geometry were studied serially both before and during (~every 3 min) a continuous 30-60 min intravenous infusions (2.0 mg/kg/hr IV, n=4). Subsequently, a set of conscious rats were also treated with either vehicle control (0 mg/kg PO, n=3) or three dose-levels of compound 3 via oral gavage: LOW (2 mg/kg PO, n=4), MID (5 mg/kg PO, n=4), or HIGH (10 mg/kg PO, n=5). In these animals, cardiac function/geometry were recorded at two separate time-points/days under isoflurane anesthesia: once prior to dosing (i.e., at baseline, day −2) and at 2 hrs post-dosing (day 0), a time when exposures are known to approach steady-state and peak responses are expected. In these experiments, left-ventricular fractional shortening (FS), an index of systolic performance, as well as LV dimensions/volumes and heart rates were measured using a high-frequency transducer and parasternal long-axis transthoracic views (Vevo2100, VisualSonic). FS was defined as the end-diastole normalized change in internal dimensions/diameter of the left ventricle between end-systole (LVESd) and end-diastole (LVEDd) (i.e., FS=100×[LVEDd−LVESd]/LVEDd). LV volumes were derived assuming a Teichholz model (LVV=7×[2.4+LVid]$^{-1}$×LVid$^3$). In all cases, blood samples were taken (via tail-vein micro-sampling) at the time of each echocardiographic examination in order to establish pharmacokinetic/pharmacodynamics (PK/PD) relationships.

Cardiomyocyte Contractility Assay

Contractility of adult rat ventricular myocytes is determined by edge detection with an IonOptix contractility system. Aliquots of myocytes in Tyrode buffer (137 mM NaCl, 3.7 mM KCL, 0.5 mM MgCl$_2$, 1.5 mM CaCl$_2$), 4 mM HEPES, 11 mM glucose) are placed in a perfusion chamber (Series 20 RC-27NE; Warner Instruments), allowed to adhere to the coverslip, and then perfused with 37° C. Tyrode buffer. Myocytes are filed stimulated at 1 Hz and 10V. Only myocytes with clear striations, quiescent prior to pacing, with a cell length of 120-180 microns, a basal fractional shortening equal to 3-8% of the cell length, and a contraction velocity greater than 100 microns per second are used for contractility experiments. To determine the response to compounds (at 0.3 µM concentration), myocytes are first perfused for 60 seconds with Tyrodes buffer followed by 5 min of compound and a 140 second washout with Tyrodes buffer. Data is continuously recorded using IonOptix software. Contractility data is analyzed using Ionwizard software (IonOptix). For each cell, 10-20 contractility transients were averaged and compared under basal (no compound) and compound-treated conditions. Compound activity is measured by effects on fractional shortening (FS), where fractional shortening is the ratio of the peak length of the cell at contraction divided by the basal cell length normalized to 100% for an untreated cell. The % inhibition measurement is calculated by subtracting the FS value from 100%.

Reactive Metabolite Identification

In vitro determination of reactive metabolite formation for small molecules by detection of glutathione adducts formed in vitro in incubations with human liver microsomes fortified with NADPH and glutathione.

Methods: The metabolism of small molecules (30 µM) for glutathione adduct formation was assessed in incubations (200 µL volume, n=3 incubations per treatment, 60 min incubation time) with liver microsomes from human (1 mg/mL protein) conducted in potassium phosphate buffer (0.1 M, pH 7.4) for 1 h at 37° C. in a 96-well plate (2 mL well volume) and were performed in the absence of NADPH (used as a negative control) and in the presence of NADPH (1 mM) and glutathione (GSH, 10 mM). Incubations with liver microsomes were performed in a shaking water bath incubator with slow horizontal shaking (30 rpm). To obtain 30 µM incubation concentration of a compound, a 3 mM substrate stock solution in DMSO was used. Final incubation mixtures contained 148 µL of potassium phosphate buffer, 10 µL of liver microsome solution (20 mg protein/mL), 2 µL of the 3 mM substrate solution and where incubations were initiated by the addition of 40 µL of NADPH solution (5 mM dissolved in potassium phosphate buffer). Non-NADPH containing incubations were supplemented with 40 µL of potassium phosphate buffer. Post-incubation, reactions were terminated by adding an equal volume of acetonitrile containing 20 nM carbamazepine internal standard and 3% formic acid. Quenched samples then were centrifuged (4,600 rpm, 4° C., 10-min) after which the supernatants were transferred to a 96-well LC-MS sample analysis plate and diluted with one volume equivalent of HPLC-grade water, and then heat sealed with aluminum foil prior to analysis by liquid chromatography/mass spectrometry (LC-MS/MS).

Analyte identification: The LC-MS/MS detection (with in-line UV detection at 280 nm) of test compounds and potential GSH-adducts was focused on extracting selected ion chromatographic profiles using the protonated molecular ion MH$^+$ m/z for parent to 4 decimal places, and corresponding protonated molecular ions of predicted GSH-adduct metabolites (m/z MH$^+$ parent+305.0681 amu) using Xcalibur software (version 2.1.0, Thermo Fisher Scientific, Waltham, MA). Relative GSH-adduct abundance in vitro in liver microsome extracts was assessed using the LC/UV absorbance at 280 nm peak area ratio obtained by using Xcalibur software (version 2.1.0) between the detected GSH-adducts from NADPH- and GSH-fortified incubation extracts and the corresponding LC/UV peak area of the parent compound from minus NADPH containing incubation extracts. The extent of GSH-adduct formation was determined by LC-MS/MS analysis with in-line LC-UV detection at 280 nm by dividing the glutathione-adduct LC/UV peak area by the LC/UV peak area of the corresponding parent HCM-1 NG analog determined from analysis of control (-NAPDH, -GSH) incubations extracts.

Materials: Pooled male human (HLM, 50 donors) liver microsomes were obtained from Bioreclamation IVT (Baltimore, MD). Glutathione (GSH) and NADPH were purchased from Sigma Chemical Co. (St. Louis, MO). All solvents used for liquid chromatography-tandem mass spectrometry (LC-MS/MS) analyses were of chromatographic grade.

LC-MS Conditions: Extracts from incubations with liver microsomes and hepatocytes were characterized by LC-MS and LC-MS/MS on a Thermo Electron LTQ Orbitrap XL mass spectrometer coupled with a Dionex UltiMate 3000 UHPLC containing in-line diode array detection and an OAS-3300TXRS Autosampler (40 µL injection volume). Electrospray ionization (ESI) was employed in the positive ion mode with the needle potential held at 5.01 kV, a sheath flow rate of 35.02, aux flow rate of 9.99, a current of 2.6 uA, a capillary temperature of 325° C., and a capillary voltage of 15.99. Vacuum conditions used were an ion gauge pressure used was 2.33×10$^{-5}$ Torr and a convection gauge pressure of 0.90 Torr. Positive ion mode full scan (m/z 100 to m/z 1000) LC-MS analysis was conducted with a scan time of 0.73-sec and source collision energy of 10 V. The tandem MS/MS conditions used were 2 mTorr helium collision gas and a collision potential of 35 eV. Xcalibur software (version 2.1.0, Thermo Fisher Scientific, Waltham, MA) was used to acquire all data.

Capillary temperature (° C.): 325
Source heater temperature (° C.): 345
Sheath gas flow (mL/min): 50
Auxiliary gas flow (mL/min): 12
Sweep gas flow (mL/min): 5
Source voltage (kV): 5.01
Source current (µA): 2.6
S-lens RF level: 50

Data dependent scans were utilized that collected MS/MS spectra of the most abundant masses in the Orbitrap (15,000 resolving power) full scan mass spectrum.

HPLC conditions: Incubation extracts were chromatographed on a Phenomenex Kinetex®, 2.6 μm, C18, 100 Å, 100×2.1 mm reverse phase column with a column oven temperature of 30° C. for the chromatographic resolution of HCM-1 NG compounds and corresponding glutathione adducts. Chromatographic resolution was achieved by reverse phase gradient elution at a flow rate of 0.3 mL/min into the ESI source over 30 min, and where the gradient aqueous mobile phase solvent-A consisted of water with 0.1% formic acid (v/v) and the organic mobile phase (solvent-B) contained acetonitrile with 0.1% formic acid (v/v). Elution was achieved by an initial aqueous solvent-A mobile phase at 95% with a linear decrease to 50% solvent-A over 20 min, followed by linear decrease to 0% solvent-A over 3.5 min, and held constant at 0% solvent-A for 1 min. Finally, a linear increase of the gradient to 95% solvent-A over 0.5 min, followed by 5 min of equilibration at 95% solvent-A prior to further analyses.

Column: Phenomenex Kinetex®, 2.6 μm, C18, 100 Å, 100×2.1 mm reverse phase column
Column oven temperature: 30° C.
Flow rate: 0.3 mL/min
Mobile phase solvent-A: water with 0.1% formic acid (v/v)
Mobile phase solvent-B: acetonitrile with 0.1% formic acid (v/v)
Elution Gradient:
0 min 95% A
0 to 20 min 50% A; linear
20 to 23.5 min 0% A; linear
23.5 to 24.5 min 0% A
24.5 to 25.0 min 95% A; linear
25.0 to 30.0 min 95% A Biological Evaluation Tables

TABLE 5

| Structure | bcMF pCa 6 IC$_{50}$ (μM) | bcMF serum pCa 6 IC$_{50}$ (μM) | Cardiac selectivity ratio vs rbskMF pCa 6 IC$_{50}$ | % inhibition of FS at 0.3 μM | % GSH-adduct (+NADPH, +GSH) relative to parent (−NADPH, −GSH) |
|---|---|---|---|---|---|
| [structure] | 1.57 | 3.49 | 5.48 | ++ (Early after depolarization or EAD) | Not Detected |
| [structure] | 2.13 | 3.11 | 10.71 | | |
| [structure] | 3.03 | 3.7 | 7.38 | | Not Detected |
| [structure] | 1.11 | 1.56 | 4.51 | +++ | Not Detected |

In Table 1B, in the column headed "% inhibition of FS at 0.3 uM", + represents inhibition of fractional shortening less than 33%, ++ represents inhibition of fractional shortening from 33% to 66%, +++ represents inhibition of fractional shortening greater than 66% (i.e., the greatest inhibition at +++).

TABLE 6
| Compound | Glutathione Adduct Detection in Human Liver Microsome Incubations (single measurement) | Average (triple measurements) | Standard Deviation (SD) (triple measurements) |
|---|---|---|---|
| 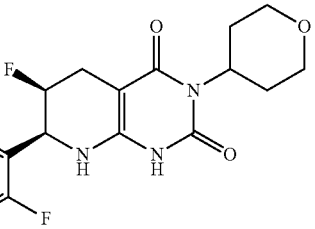<br>7 | 0.3% | 0.4 | 0.1 |
| 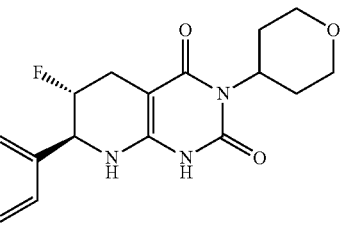<br>2 | Not Detected | Not Detected | — |
| 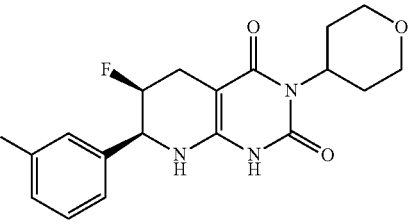<br>1 | Not Detected | Not Detected | — |
| 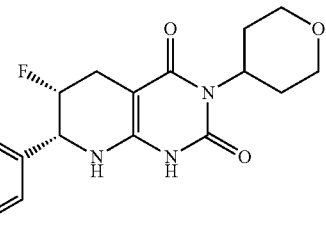<br>12 | Not Detected | Not Detected | — |
| 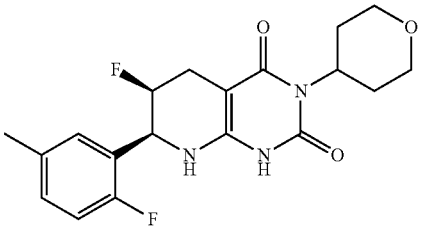 [SMILES: Cc1ccc(F)c([C@@H]2Nc3[nH]c(=O)n(C4CCOCC4)c(=O)c3C[C@@H]2F)c1]<br>3 | Not Detected | Not Detected | — |

TABLE 6-continued

| Compound | Glutathione Adduct Detection in Human Liver Microsome Incubations (single measurement) | Average (triple measurements) | Standard Deviation (SD) (triple measurements) |
|---|---|---|---|
| 4 | Not Detected | Not Detected | — |
| 5 | Not Detected | Not Detected | — |
| 6 | Not Detected | Not Detected | — |
| 11 | Not Detected | Not Detected | — |
| 9 | Not Detected | Not Detected | — |

TABLE 6-continued

| Compound | Glutathione Adduct Detection in Human Liver Microsome Incubations (single measurement) | Average (triple measurements) | Standard Deviation (SD) (triple measurements) |
|---|---|---|---|
| 8 | Not Detected | Not Detected | — |
| 10 | Not Detected | Not Detected | — |

Table 1C represents the data from a single experiment.

As demonstrated above, these compounds showed minimal or no development of reactive metabolites.

X-Ray Powder Diffraction (XRPD)

XRPD analysis was carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha_1 \lambda = 1.54060$ Å; $\alpha_2 = 1.54443$ Å; $\beta = 1.39225$ Å; $\alpha_1$: $\alpha_2$ ratio=0.5) running in transmission mode (step size 0.0130° 2θ) using 40 kV/40 mA generator settings.

Thermogravimetric Analysis (TGA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 400° C. during which time the change in sample weight was recorded along with any differential thermal events (DTA). Nitrogen was used as the purge gas, at a flow rate of 300 cm³/min.

Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to max 330° C. at scan rate of 10° C./min and the resulting heat flow response monitored. Nitrogen was used as the purge gas, at a flow rate of 50 cm³/min. Modulated DSC was carried with amplitude=0.32° C. and frequency=0.017 Hz.

The disclosure also comprises the following clauses:

1. A compound having the formula:

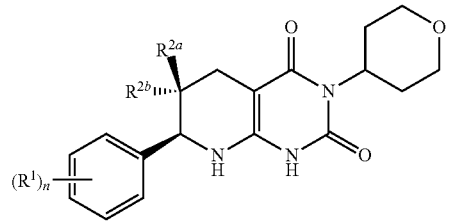

or a pharmaceutically acceptable salt thereof, wherein the subscript n is 1 or 2;

each $R^1$ is a member selected from the group consisting of fluoro, chloro, $C_1$-$C_4$ alkyl, $C_1$-$C_4$ haloalkyl, $C_1$-$C_4$ alkoxy, $C_1$-$C_4$ haloalkoxy, and $C_2$-$C_4$ alkynyl; wherein at least one $R^1$ is fluoro; and one of $R^{2a}$ and $R^{2b}$ is fluoro and the other of $R^{2a}$ and $R^{2b}$ is H; or optionally, wherein the subscript n is 1 or 2;

each $R^1$ is a member selected from the group consisting of fluoro, chloro, optionally substituted $C_1$-$C_4$ alkyl, optionally substituted $C_1$-$C_4$ haloalkyl, optionally substituted $C_1$-$C_4$ alkoxy, optionally substituted $C_1$-$C_4$ haloalkoxy, and optionally substituted $C_2$-$C_4$ alkynyl; wherein at least one $R^1$ is fluoro; and one of $R^{2a}$ and $R^{2b}$ is fluoro and the other of $R^{2a}$ and $R^{2b}$ is H.

2. The compound of clause 1, or a pharmaceutically acceptable salt thereof wherein $R^{2a}$ is fluoro.

3. The compound of clause 1, or a pharmaceutically acceptable salt thereof wherein $R^{2b}$ is fluoro.

4. The compound of clause 1, or a pharmaceutically acceptable salt thereof wherein $R^{2a}$ is fluoro, and n is 1.

5. The compound of clause 1, or a pharmaceutically acceptable salt thereof wherein $R^{2a}$ is fluoro, and n is 2.

6. The compound of clause 1, or a pharmaceutically acceptable salt thereof wherein $R^{2b}$ is fluoro, and n is 1.

7. The compound of clause 1, or a pharmaceutically acceptable salt thereof wherein $R^{2b}$ is fluoro, and n is 2.

8. The compound of any one of clauses 1 to 3, or a pharmaceutically acceptable salt thereof wherein n is 1.

9. The compound of clause 1, having the formula:

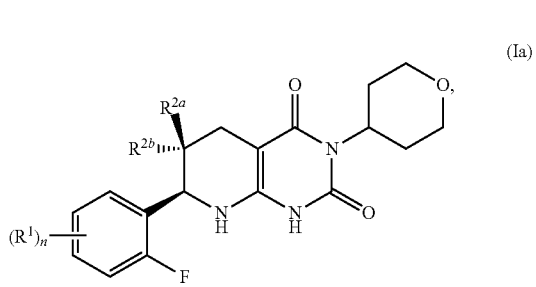

(Ia)

or pharmaceutically acceptable salt thereof, wherein the subscript n is 1; and
- $R^1$ is a member independently selected from the group consisting of fluoro, chloro, $C_1$-$C_4$ alkyl, $C_1$-$C_4$ haloalkyl, $C_1$-$C_4$ alkoxy, $C_1$-$C_4$ haloalkoxy, and $C_2$-$C_4$ alkynyl; and one of $R^{2a}$ and $R^{2b}$ is fluoro and the other of $R^{2a}$ and $R^{2b}$ is H; or optionally, wherein n is 1; and
- $R^1$ is a member independently selected from the group consisting of fluoro, chloro, optionally substituted $C_1$-$C_4$ alkyl, optionally substituted $C_1$-$C_4$ haloalkyl, optionally substituted $C_1$-$C_4$ alkoxy, optionally substituted $C_1$-$C_4$ haloalkoxy, and optionally substituted $C_2$-$C_4$ alkynyl; and
- one of $R^{2a}$ and $R^{2b}$ is fluoro and the other of $R^{2a}$ and $R^{2b}$ is H.

10. The compound of clause 8, having the formula:

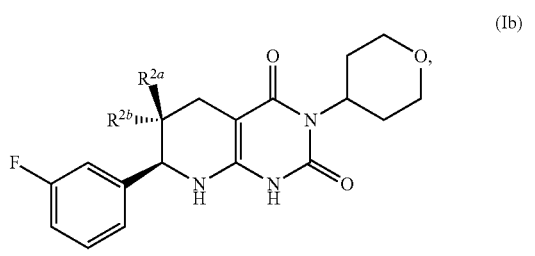

(Ib)

or a pharmaceutically acceptable salt thereof.

11. The compound of clause 1, or a pharmaceutically acceptable salt thereof where n is 2; optionally one $R^1$ is fluoro and the other is selected from the group consisting of fluoro, $C_1$-$C_4$ alkyl, $C_2$-$C_4$ alkoxy and $C_2$-$C_4$ alkynyl; optionally one $R^1$ is fluoro and the other is selected from the group consisting of fluoro, methyl, methoxy and ethynyl; or optionally,
  wherein n is 2; optionally one $R^1$ is fluoro and the other is selected from the group consisting of fluoro, optionally substituted $C_1$-$C_4$ alkyl, optionally substituted $C_2$-$C_4$ alkoxy and optionally substituted $C_2$-$C_4$ alkynyl; optionally one $R^1$ is fluoro and the other is selected from the group consisting of fluoro, hydroxymethyl, methyl, methoxy and ethynyl.

12. The compound of any one of clauses 1 to 3, or a pharmaceutically acceptable salt thereof wherein n is 2, optionally having the formula:

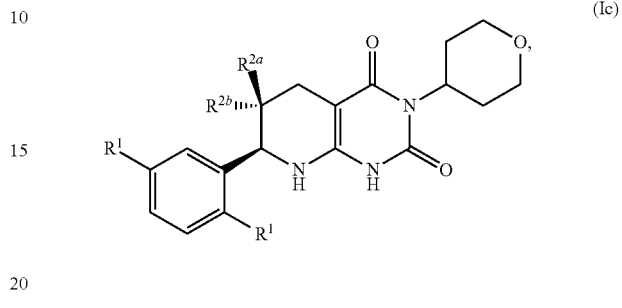

(Ic)

or a pharmaceutically acceptable salt thereof.

13. The compound of clause 12, or a pharmaceutically acceptable salt thereof wherein one $R^1$ is fluoro and the other is selected from the group consisting of fluoro, $C_1$-$C_4$ alkyl, $C_1$-$C_4$ alkoxy, and $C_2$-$C_4$ alkynyl; optionally fluoro, methyl, methoxy and ethynyl (—C≡CH), optionally methyl, methoxy and ethynyl (—C≡CH); or optionally,
  wherein one $R^1$ is fluoro and the other is selected from the group consisting of fluoro, optionally substituted $C_1$-$C_4$ alkyl, optionally substituted $C_1$-$C_4$ alkoxy, and optionally substituted $C_2$-$C_4$ alkynyl; optionally fluoro, hydroxymethyl, methoxy and ethynyl (—C≡CH), optionally methyl, methoxy and ethynyl (—C≡CH).

14. The compound of any one of clauses 1 to 3, having the formula:

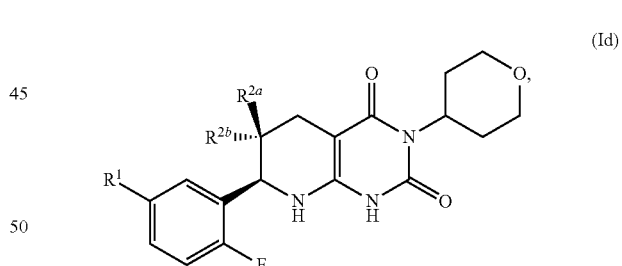

(Id)

or a pharmaceutically acceptable salt thereof.

15. The compound of clause 14, or a pharmaceutically acceptable salt thereof wherein $R^1$ is selected from the group consisting of fluoro, $C_1$-$C_4$ alkyl, $C_1$-$C_4$ alkoxy, and $C_2$-$C_4$ alkynyl; optionally fluoro, methyl, methoxy and ethynyl (—C≡CH), optionally methyl, methoxy and ethynyl (—C≡CH); or optionally,
  wherein $R^1$ is selected from the group consisting of fluoro, optionally substituted $C_1$-$C_4$ alkyl, optionally substituted $C_1$-$C_4$ alkoxy, and optionally substituted $C_2$-$C_4$ alkynyl; optionally fluoro, methyl, methoxy and ethynyl (—C≡CH), optionally methyl, hydroxymethyl, methoxy and ethynyl (—C≡CH).

16. The compound of clause 1, having the formula:

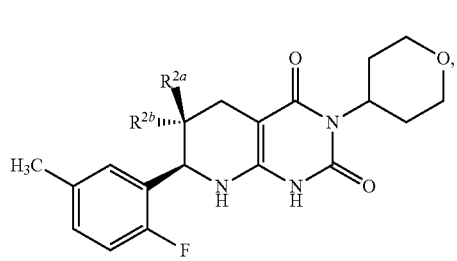
(Ie)

or a pharmaceutically acceptable salt thereof.

17. The compound of clause 1, wherein the compound is:

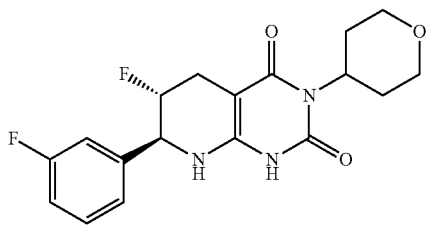

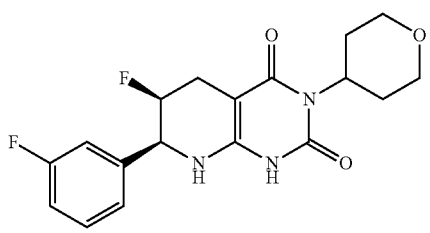

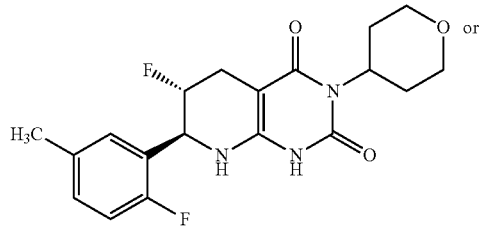

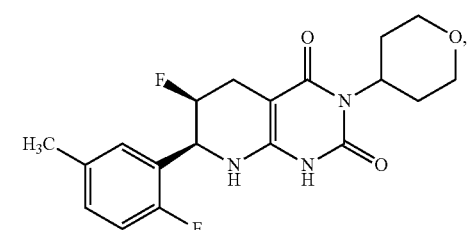

or pharmaceutically acceptable salt of any of the foregoing.

18. The compound of clause 1, wherein the compound is:

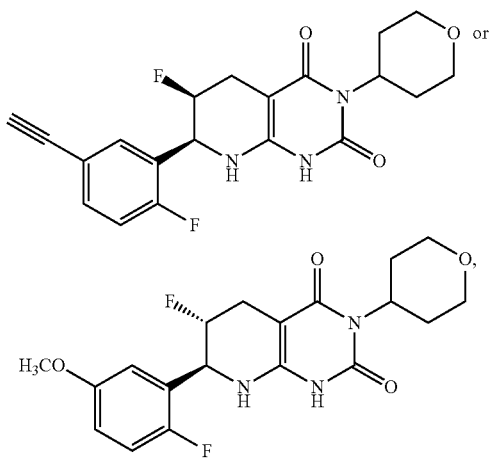

or a pharmaceutically acceptable salt of any of the foregoing.

19. The compound of clause 1, having the formula:

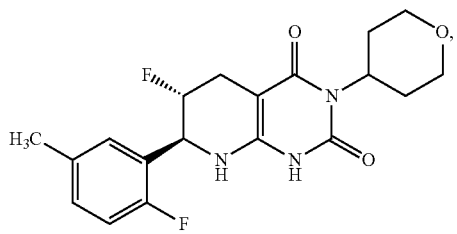 [SMILES: Cc1ccc(F)c([C@@H]2Nc3[nH]c(=O)n(C4CCOCC4)c(=O)c3C[C@H]2F)c1]

or a pharmaceutically acceptable salt thereof.

20. The compound of clause 1, having the formula:

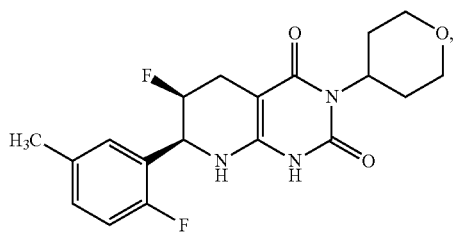 [SMILES: Cc1ccc(F)c([C@@H]2Nc3[nH]c(=O)n(C4CCOCC4)c(=O)c3C[C@@H]2F)c1]

or a pharmaceutically acceptable salt thereof.

21. The compound of clause 1, having the formula:

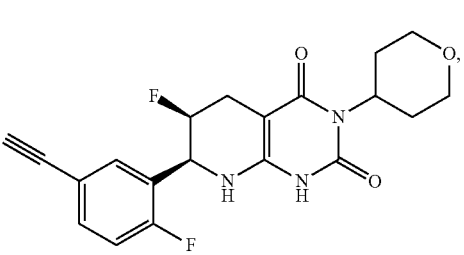 [SMILES: C#Cc1ccc(F)c([C@@H]2Nc3[nH]c(=O)n(C4CCOCC4)c(=O)c3C[C@@H]2F)c1]

or a pharmaceutically acceptable salt thereof.

22. The compound of clause 1, having the formula:

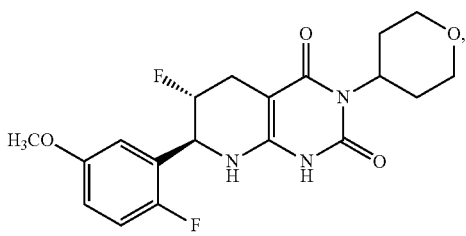 [SMILES: COc1ccc(F)c([C@@H]2Nc3[nH]c(=O)n(C4CCOCC4)c(=O)c3C[C@H]2F)c1]

or a pharmaceutically acceptable salt thereof.

23. The compound of clause 1, having the formula:

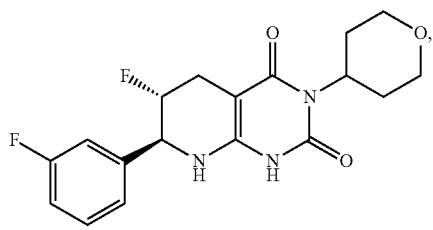 [SMILES: O=c1[nH]c2c(c(=O)n1C1CCOCC1)C[C@@H](F)[C@H](c1cccc(F)c1)N2]

or a pharmaceutically acceptable salt thereof.

24. The compound of clause 1, having the formula:

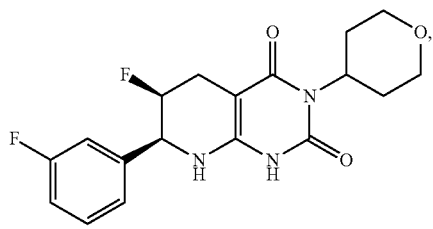 [SMILES: O=c1[nH]c2c(c(=O)n1C1CCOCC1)C[C@H](F)[C@H](c1cccc(F)c1)N2]

or a pharmaceutically acceptable salt thereof.

25. A pharmaceutical composition comprising a compound according to any one of clauses 1 to 24, or pharmaceutically acceptable salt thereof, optionally further comprising a pharmaceutically acceptable excipient.

26. The pharmaceutical composition according to clause 25, wherein the composition is substantially free of other isomers at the carbon atom bearing the phenyl ring.

27. The pharmaceutical composition according to clause 25 or 26, wherein the composition is substantially free of other isomers at the carbon atom bearing fluoro adjacent the carbon atom bearing the phenyl ring.

28. A method of treatment, comprising administering to a subject in need thereof an effective amount of a compound according to any one of clauses 1 to 24, or a pharmaceutically acceptable salt thereof, or a pharmaceutical composition according to any one of clauses 25 to 27.

29. A method of treating hypertrophic cardiomyopathy (HCM) or a cardiac disorder (for example a cardiac disorder having a pathophysiological feature of HCM), comprising administering to a subject in need thereof an effective amount of a compound according to any one of clauses 1 to 24, or a pharmaceutically acceptable salt thereof, or a pharmaceutical composition according to any one of clauses 25 to 27.

30. A method of treating a disease or disorder selected from the group consisting of diastolic heart failure (for example a heart failure with preserved ejection fraction), ischemic heart disease, angina pectoris, and restrictive cardiomyopathy, comprising administering to a subject in need thereof an effective amount of a compound according to any one of clauses 1 to 24, or a pharmaceutically acceptable salt thereof, or a pharmaceutical composition according to any one of clauses 25 to 27.

31. A method of treating a disease or disorder characterized by left ventricular hypertrophy (for example left ventricular hypertrophy due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy, comprising administering to a subject in need thereof an effective amount of a compound of any one of clauses 1 to 24, or a pharmaceutically acceptable salt thereof, or a pharmaceutical composition according to any one of clauses 25 to 27.

32. A method of treating hypertrophic cardiomyopathy (HCM), or a cardiac disorder (for example a cardiac disorder having a pathophysiological feature associated with HCM), comprising administering to a subject in need thereof an effective amount of a compound according to any one of clauses 1 to 24, or a pharmaceutically acceptable salt thereof, or a pharmaceutical composition according to any one of clauses 25 to 27, combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

33. A compound according to any one of clauses 1 to 24, or pharmaceutically acceptable salt thereof, or a pharmaceutical composition according to any one of clauses 25 to 27, for use as a medicament.

34. A compound according to any one of clauses 1 to 24, or pharmaceutically acceptable salt thereof, or a pharmaceutical composition according to any one of clauses 25 to 27, for use in the treatment of hypertrophic cardiomyopathy, or a cardiac disorder (for example a cardiac disorder having a pathophysiological feature of HCM).

35. A compound according to any one of clauses 1 to 24, or pharmaceutically acceptable salt thereof, or a pharmaceutical composition according to any one of clauses 25 to 27, for use in the treatment of a disease or disorder selected from the group consisting of diastolic heart failure (for example of heart failure with preserved ejection fraction), ischemic heart disease, angina pectoris, and restrictive cardiomyopathy.

36. A compound according to any one of clauses 1 to 24, or pharmaceutically acceptable salt thereof, or a pharmaceutical composition according to any one of clauses 25 to 27, for use in the treatment of a disease or disorder characterized by left ventricular hypertrophy (for example left ventricular hypertrophy due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy.

37. A compound according to any one of clauses 1 to 24, or pharmaceutically acceptable salt thereof, or a pharmaceutical composition according to any one of clauses 25 to 27, for use in the treatment of hypertrophic cardiomyopathy (HCM), or a cardiac disorder (for example a cardiac disorder having a pathophysiological feature associated with HCM), wherein the compound is for use in combination with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

38. A compound according to any one of clauses 1 to 24, or pharmaceutically acceptable salt thereof, or a pharmaceutical composition according to any one of clauses 25 to 27, for the manufacture of a medicament.

39. Use of compound according to any one of clauses 1 to 24 or pharmaceutically acceptable salt thereof, or a pharmaceutical composition according to any one of clauses 25 to 27, for the manufacture of a medicament for the treatment of hypertrophic cardiomyopathy, or a cardiac disorder (for example a cardiac disorder having a pathophysiological feature of HCM).

40. Use of compound according to any one of clauses 1 to 24 or pharmaceutically acceptable salt thereof, or a pharmaceutical composition according to any one of clauses 25 to 27, for the manufacture of a medicament for the treatment of a disease or disorder selected from the group consisting of diastolic heart failure (for example heart failure with preserved ejection fraction), ischemic heart disease, angina pectoris, and restrictive cardiomyopathy.

41. Use of compound according to any one of clauses 1 to 24 or pharmaceutically acceptable salt thereof, or a pharmaceutical composition according to any one of clauses 25 to 27, for the manufacture of a medicament for the treatment of a disease or disorder characterized by left ventricular hypertrophy (for example due to volume or pressure overload), said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy.

42. Use of compound according to any one of clauses 1 to 24 or pharmaceutically acceptable salt thereof, or a pharmaceutical composition according to any one of clauses 25 to 27, for the manufacture of a medicament for the treatment of hypertrophic cardiomyopathy (HCM), or a cardiac disorder (for example a cardiac disorder having a pathophysiological feature associated with HCM), combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

43. Form 1 polymorph of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione characterized by at least one of:
   a. a powder X-ray diffraction pattern having two or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees;
   b. a DSC thermogram showing endotherms at about 226.05° C., at about 302.47° C., and at about 310.13° C.; or
   c. an X-ray crystal structure substantially the same as in FIG. 4.

44. The polymorph of clause 43, characterized by a powder X-ray diffraction pattern having three or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees.

45. The polymorph of clause 43, characterized by a powder X-ray diffraction pattern having four or more peaks expressed in degrees 2-theta±0.2° and selected from 11.3, 12.4, 13.3, 16.5, 17.3, 19.3, 20.4, 21.2, 22.5, 23.2, 25.5, 26.4, 28.2, 29.5, 31.5, 32.9, 34.3, 35.5, and 38.8 degrees.

46. The polymorph of clause 43, characterized by a powder X-ray diffraction having peaks expressed in degrees 2-theta±0.2° at each of 11.3, 12.4, and 13.3 degrees.

47. The polymorph of clause 43, characterized by a powder X-ray diffraction having peaks expressed in degrees 2-theta±0.2° at each of 11.3, 12.4, 13.3, 16.5, 17.3, 19.3, 20.4, and 29.5 degrees.

48. The polymorph of clause 43, characterized by melt onsets of about 221.51° C., about 299.53° C., and about 308.81° C.

49. The polymorph of clause 43, wherein the polymorph has a powder X-ray diffraction pattern substantially the same as in FIG. 1A.

50. The polymorph of any one of clauses 43-49, wherein the Form 1 polymorph is substantially free of other forms of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione.

51. A pharmaceutical composition comprising a polymorph of any one of clauses 43-50, and a pharmaceutically acceptable excipient.

52. The composition of clause 51, wherein the ratio of the amount of the Form 1 polymorph to the sum of the amounts of other forms is equal to or greater than 80:20.

53. The composition of clause 51, wherein the ratio of the amount of the Form 1 polymorph to the sum of the amounts of other forms is equal to or greater than 90:10.

54. The composition of clause 51, wherein the ratio of the amount of the Form 1 polymorph to the sum of the amounts of other forms is equal to or greater than 95:5.

55. The composition of clause 51, wherein the ratio of the amount of the Form 1 polymorph to the sum of the amounts of other forms is equal to or greater than 97:3.

56. The composition of clause 51, wherein the ratio of the amount of the Form 1 polymorph to the sum of the amounts of other forms is equal to or greater than 98:2.

57. The composition of clause 51, wherein the ratio of the amount of the Form 1 polymorph to the sum of the amounts of other forms is equal to or greater than 99:1.

58. A method of treating hypertrophic cardiomyopathy (HCM), or a cardiac disorder having a pathophysiological feature of HCM, comprising administering to a subject in need thereof an effective amount of a polymorph of any one of clauses 43-50, or a pharmaceutical composition of any one of clauses 51-57.

59. A method of treating a disease or disorder characterized by left ventricular hypertrophy due to volume or pressure overload, said disease or disorder selected from the group consisting of chronic mitral regurgitation, chronic aortic stenosis, and chronic systemic hypertension; in conjunction with therapies aimed at correcting or alleviating the primary cause of volume or pressure overload, including valve repair/replacement or effective antihypertensive therapy, comprising administering to a subject in need thereof an effective amount of a polymorph of any one of clauses 43-50, or a pharmaceutical composition of any one of clauses 51-57.

60. A method of treating hypertrophic cardiomyopathy (HCM), or a cardiac disorder having a pathophysiological feature associated with HCM, comprising administering to a subject in need thereof an effective amount of a polymorph of any one clauses 43-50, or a pharmaceutical composition of any one of clauses 51-57, combined with therapies that retard the progression of heart failure by down-regulating neurohormonal stimulation of the heart and attempt to prevent cardiac remodeling (e.g., ACE inhibitors, angiotensin receptor blockers (ARBs), β-blockers, aldosterone receptor antagonists, or neural endopeptidase inhibitors); therapies that improve cardiac function by stimulating cardiac contractility (e.g., positive inotropic agents, such as the β-adrenergic agonist dobutamine or the phosphodiesterase inhibitor milrinone); and/or therapies that reduce cardiac preload (e.g., diuretics, such as furosemide) or afterload (vasodilators of any class, including but not limited to calcium channel blockers, phosphodiesterase inhibitors, endothelin receptor antagonists, renin inhibitors, or smooth muscle myosin modulators).

The recitation of a listing of chemical groups in any definition of a variable herein includes definitions of that variable as any single group or combination of listed groups.

Although the foregoing disclosure has been described in some detail by way of illustration and example for purposes of clarity of understanding, one of skill in the art will appreciate that 5 certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A crystalline Form 1 of (6S,7S)-6-fluoro-7-(2-fluoro-5-methylphenyl)-3-(tetrahydro-2H-pyran-4-yl)-5,6,7,8-tetrahydropyrido[2,3-d]pyrimidine-2,4(1H,3H)-dione having the following formula:

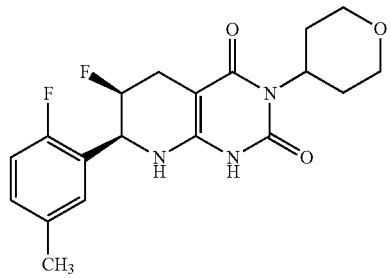 [SMILES: Cc1ccc(F)c([C@@H]2Nc3[nH]c(=O)n(C4CCOCC4)c(=O)c3C[C@@H]2F)c1]

wherein crystalline Form 1 is characterized by a powder X-ray diffraction pattern having two or more peaks at angles expressed in °2θ selected from the group consisting of 11.3°±0.2°, 12.4°±0.2°, 13.3°±0.2°, 16.5°±0.2°, 17.3°±0.2°, 19.3°±0.2°, 20.4°±0.2°, 21.2°±0.2°, 22.5°±0.2°, 23.2°±0.2°, 25.5°±0.2°, 26.4°±0.2°, 28.2°±0.2°, 29.5°±0.2°, 31.5°±0.2°, 32.9°±0.2°, 34.3°±0.2°, 35.5°±0.2°, and 38.8°±0.2°.

2. The crystalline Form 1 of claim 1, wherein the crystalline Form 1 is further characterized by a powder X-ray diffraction pattern having three or more peaks at angles expressed in °2θ selected from the group consisting of 11.3°±0.2°, 12.4°±0.2°, 13.3°±0.2°, 16.5°±0.2°, 17.3°±0.2°, 19.3°±0.2°, 20.4°±0.2°, 21.2°±0.2°, 22.5°±0.2°, 23.2°±0.2°, 25.5°±0.2°, 26.4°±0.2°, 28.2°±0.2°, 29.5°±0.2°, 31.5°±0.2°, 32.9°+0.2°, 34.3°±0.2°, 35.5°±0.2°, and 38.8°±0.2°.

3. The crystalline Form 1 of claim 1, wherein the crystalline Form 1 is further characterized by a powder X-ray diffraction pattern having four or more peaks at angles expressed in °2θ selected from the group consisting of 11.3°±0.2°, 12.4°±0.2°, 13.3°±0.2°, 16.5°±0.2°, 17.3°±0.2°, 19.3°±0.2°, 20.4°±0.2°, 21.2°±0.2°, 22.5°±0.2°, 23.2°±0.2°, 25.5°±0.2°, 26.4°±0.2°, 28.2°±0.2°, 29.5°±0.2°, 31.5°±0.2°, 32.9°+0.2°, 34.3°±0.2°, 35.5°±0.2°, and 38.8°±0.2°.

4. The crystalline Form 1 of claim 1, wherein the crystalline Form 1 is further characterized by a powder X-ray diffraction pattern having peaks at angles expressed in °2θ of 11.3°±0.2°, 12.4°±0.2°, and 13.3°±0.2°.

5. The crystalline Form 1 of claim 4, wherein the crystalline Form 1 is further characterized by a powder X-ray diffraction pattern having additional peaks at angles expressed in °2θ of 16.5°±0.2°, 17.3°±0.2°, 19.3°±0.2°, 20.4°±0.2°, and 29.5°±0.2°.

6. The crystalline Form 1 of claim 1, wherein the crystalline Form 1 is further characterized by a powder X-ray diffraction pattern as shown in FIG. 1A.

7. The crystalline Form 1 of claim 1, wherein the crystalline Form 1 is further characterized by an X-ray crystal structure as shown in FIG. 4.

8. The crystalline Form 1 of claim 1, wherein the crystalline Form 1 is further characterized by a differential scanning calorimetry (DSC) thermogram showing endotherms expressed in ° C. at 226.05° C.±2° C., 302.47° C.±2° C., and 310.13° C.±2° C.

9. The crystalline Form 1 of claim 1, wherein the crystalline Form 1 is further characterized by melt onsets expressed in ° C. at 221.51° C.±2° C., 299.53° C.±2° C., and 308.81° C.±2° C.

10. A pharmaceutical composition comprising a pharmaceutically acceptable excipient and the crystalline Form 1 of claim 1.

11. A method for treating heart failure with preserved ejection fraction (HFpEF) in a subject in need thereof, wherein the method comprises administering to the subject a pharmaceutically effective amount of the crystalline Form 1 of claim 1.

12. A method for treating hypertrophic cardiomyopathy (HCM) in a subject in need thereof, wherein the method comprises administering to the subject a pharmaceutically effective amount of the crystalline Form 1 of claim 1.

13. The method of claim 12, wherein the hypertrophic cardiomyopathy (HCM) is obstructive hypertrophic cardiomyopathy (oHCM).

14. The method of claim 12, wherein the hypertrophic cardiomyopathy (HCM) is non-obstructive hypertrophic cardiomyopathy (nHCM).

15. A method for treating left ventricular hypertrophy in a subject in need thereof, wherein the method comprises administering to the subject a pharmaceutically effective amount of the crystalline Form 1 of claim 1.

* * * * *